United States Patent
Cohen et al.

(10) Patent No.: US 9,234,041 B2
(45) Date of Patent: Jan. 12, 2016

(54) ANTIBODIES TO INSULIN-LIKE GROWTH FACTOR I RECEPTOR

(71) Applicants: Amgen Fremont Inc., Thousand Oaks, CA (US); Pfizer Inc., New York, NY (US)

(72) Inventors: Bruce D. Cohen, East Lyme, CT (US); Jean Beebe, Jr., Salem, CT (US); Penelope E. Miller, Mystic, CT (US); James D. Moyer, East Lyme, CT (US); Jose Ramon Corvalan, Foster City, CA (US); Michael Gallo, North Vancouver (CA)

(73) Assignees: Pfizer Inc., New York, NY (US); Amgen Fremont Inc., Thousand Oaks, CA (US)

( * ) Notice: Subject to any disclaimer, the term of this patent is extended or adjusted under 35 U.S.C. 154(b) by 0 days.

(21) Appl. No.: 14/135,026

(22) Filed: Dec. 19, 2013

(65) Prior Publication Data

US 2014/0120089 A1   May 1, 2014

Related U.S. Application Data

(60) Continuation of application No. 13/169,474, filed on Jun. 27, 2011, now Pat. No. 8,642,037, which is a continuation of application No. 12/756,417, filed on Apr. 8, 2010, now Pat. No. 7,982,024, which is a division of application No. 11/144,248, filed on Jun. 2, 2005, now Pat. No. 7,815,907, which is a continuation of application No. 10/038,591, filed on Jan. 4, 2002, now Pat. No. 7,037,498.

(60) Provisional application No. 60/259,927, filed on Jan. 5, 2001.

(51) Int. Cl.

| A61K 39/395 | (2006.01) |
|---|---|
| C07K 16/00 | (2006.01) |
| C07K 16/18 | (2006.01) |
| C07K 16/28 | (2006.01) |
| C07K 16/30 | (2006.01) |
| C07K 14/72 | (2006.01) |
| G01N 33/574 | (2006.01) |
| A61K 48/00 | (2006.01) |
| A61K 39/00 | (2006.01) |

(52) U.S. Cl.
CPC ....... *C07K 16/2863* (2013.01); *A61K 39/39541* (2013.01); *A61K 39/39558* (2013.01); *C07K 14/72* (2013.01); *C07K 16/30* (2013.01); *G01N 33/574* (2013.01); *G01N 33/57492* (2013.01); *A01K 2217/05* (2013.01); *A61K 48/00* (2013.01); *A61K 2039/505* (2013.01); *C07K 2317/21* (2013.01); *C07K 2317/73* (2013.01); *C07K 2317/92* (2013.01); *G01N 2333/65* (2013.01); *G01N 2333/71* (2013.01)

(58) Field of Classification Search
None
See application file for complete search history.

(56) References Cited

U.S. PATENT DOCUMENTS

| 4,399,216 A | 8/1983 | Axel et al. |
|---|---|---|
| 4,510,245 A | 4/1985 | Cousens et al. |
| 4,634,665 A | 1/1987 | Axel et al. |
| 4,740,461 A | 4/1988 | Kaufman |
| 4,912,040 A | 3/1990 | Kaufman et al. |
| 4,959,455 A | 9/1990 | Clark et al. |
| 4,968,615 A | 11/1990 | Koszinowski et al. |
| 5,151,510 A | 9/1992 | Stec et al. |
| 5,168,062 A | 12/1992 | Stinski |
| 5,179,017 A | 1/1993 | Axel et al. |
| 5,223,409 A | 6/1993 | Ladner et al. |
| 5,530,101 A | 6/1996 | Queen et al. |
| 5,545,806 A | 8/1996 | Lonberg et al. |
| 5,545,807 A | 8/1996 | Surani et al. |
| 5,585,089 A | 12/1996 | Queen et al. |

(Continued)

FOREIGN PATENT DOCUMENTS

| EP | 0 216 846 | 4/1987 |
|---|---|---|
| EP | 0 256 055 | 2/1988 |

(Continued)

OTHER PUBLICATIONS

U.S. Appl. No. 13/831,099, Boyle et al.

(Continued)

*Primary Examiner* — Christine J Saoud
*Assistant Examiner* — Jon M Lockard
(74) *Attorney, Agent, or Firm* — Knobbe, Martens, Olson & Bear, LLP

(57) ABSTRACT

The present invention relates to antibodies and antigen-binding portions thereof that specifically bind to insulin-like growth factor I receptor (IGF-IR), which is preferably human IGF-IR. The invention also relates to human anti-IGF-IR antibodies, including chimeric, bispecific, derivatized, single chain antibodies or portions of fusion proteins. The invention also relates to isolated heavy and light chain immunoglobulin molecules derived from anti-IGF-IR antibodies and nucleic acid molecules encoding such molecules. The present invention also relates to methods of making anti-IGF-IR antibodies, pharmaceutical compositions comprising these antibodies and methods of using the antibodies and compositions thereof for diagnosis and treatment. The invention also provides gene therapy methods using nucleic acid molecules encoding the heavy and/or light immunoglobulin molecules that comprise the human anti-IGF-IR antibodies. The invention also relates to gene therapy methods and transgenic animals comprising nucleic acid molecules of the present invention.

20 Claims, 25 Drawing Sheets

(56) References Cited

U.S. PATENT DOCUMENTS

| | | |
|---|---|---|
| 5,587,458 A | 12/1996 | King et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,625,825 A | 4/1997 | Rostoker et al. |
| 5,633,425 A | 5/1997 | Lonberg et al. |
| 5,643,763 A | 7/1997 | Dunn et al. |
| 5,661,016 A | 8/1997 | Lonberg et al. |
| 5,693,761 A | 12/1997 | Queen et al. |
| 5,693,792 A | 12/1997 | Torii et al. |
| 5,714,350 A | 2/1998 | Co et al. |
| 5,721,367 A | 2/1998 | Kay et al. |
| 5,741,957 A | 4/1998 | Deboer et al. |
| 5,747,498 A | 5/1998 | Schnur et al. |
| 5,750,172 A | 5/1998 | Meade et al. |
| 5,756,687 A | 5/1998 | Denman et al. |
| 5,770,429 A | 6/1998 | Lonberg et al. |
| 5,777,085 A | 7/1998 | Co et al. |
| 5,789,215 A | 8/1998 | Berns et al. |
| 5,789,650 A | 8/1998 | Lonberg et al. |
| 5,792,783 A | 8/1998 | Tang et al. |
| 5,814,318 A | 9/1998 | Lonberg et al. |
| 5,827,690 A | 10/1998 | Meade et al. |
| 5,834,504 A | 11/1998 | Tang et al. |
| 5,861,510 A | 1/1999 | Piscopio et al. |
| 5,863,949 A | 1/1999 | Robinson et al. |
| 5,869,045 A | 2/1999 | Hellstrom et al. |
| 5,877,305 A | 3/1999 | Huston et al. |
| 5,883,113 A | 3/1999 | Tang et al. |
| 5,886,020 A | 3/1999 | Tang et al. |
| 5,886,152 A | 3/1999 | Nakatani et al. |
| 5,916,771 A | 6/1999 | Hori et al. |
| 5,939,598 A | 8/1999 | Kucherlapati et al. |
| 5,985,615 A | 11/1999 | Jakobovits et al. |
| 5,994,619 A | 11/1999 | Stice et al. |
| 5,998,209 A | 12/1999 | Jokobovits et al. |
| 6,054,297 A | 4/2000 | Carter et al. |
| 6,075,181 A | 6/2000 | Kucherlapati et al. |
| 6,084,085 A | 7/2000 | Baserga et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,146,629 A | 11/2000 | Dagan et al. |
| 6,407,213 B1 | 6/2002 | Carter et al. |
| 6,657,103 B1 | 12/2003 | Kucherlapati et al. |
| 7,037,498 B2 | 5/2006 | Cohen et al. |
| 7,173,005 B2 | 2/2007 | Pillutla et al. |
| 7,329,745 B2 | 2/2008 | Fujita-Yamaguchi |
| 7,364,736 B2 | 4/2008 | Boyle et al. |
| 7,371,378 B2 | 5/2008 | Cohen et al. |
| 7,538,195 B2 | 5/2009 | Singh |
| 7,700,742 B2 | 4/2010 | Cohen et al. |
| 7,815,907 B2 | 10/2010 | Cohen et al. |
| 7,982,024 B2 | 7/2011 | Cohen et al. |
| 8,058,418 B2 | 11/2011 | Boyle et al. |
| 8,409,578 B2 | 4/2013 | Boyle et al. |
| 2003/0165502 A1 | 9/2003 | Fujita-Yamaguchi |
| 2008/0124339 A1 | 5/2008 | Pullen et al. |

FOREIGN PATENT DOCUMENTS

| | | |
|---|---|---|
| EP | 0 323 997 | 7/1989 |
| EP | 0 338 841 | 10/1989 |
| EP | 0 606 046 | 7/1994 |
| EP | 0 780 386 | 6/1997 |
| EP | 0 818 442 | 1/1998 |
| EP | 0 931 788 | 7/1999 |
| EP | 1 004 578 | 5/2000 |
| EP | 1 709 080 | 3/2011 |
| JP | 6500233 | 1/1994 |
| JP | 8140528 | 6/1996 |
| JP | 8509612 | 10/1996 |
| RU | 2114120 C1 | 6/1998 |
| WO | WO 90-05719 | 5/1990 |
| WO | WO 91-09967 | 7/1991 |
| WO | WO 91-10741 | 7/1991 |
| WO | WO 91-17271 | 11/1991 |
| WO | WO 92-01047 | 1/1992 |
| WO | WO 92-02190 | 2/1992 |
| WO | WO 92-03918 | 3/1992 |
| WO | WO 92-09690 | 6/1992 |
| WO | WO 92-15679 | 9/1992 |
| WO | WO 92-18154 | 10/1992 |
| WO | WO 92-18619 | 10/1992 |
| WO | WO 92-20791 | 11/1992 |
| WO | WO 93-01288 | 1/1993 |
| WO | WO 93-06213 | 4/1993 |
| WO | WO 94-02602 | 2/1994 |
| WO | WO 94-25585 | 11/1994 |
| WO | WO 95-19970 | 7/1995 |
| WO | WO 95-21613 | 8/1995 |
| WO | WO 96-27583 | 9/1996 |
| WO | WO 96-33172 | 10/1996 |
| WO | WO 96-33735 | 10/1996 |
| WO | WO 96-34096 | 10/1996 |
| WO | WO 97-13760 | 4/1997 |
| WO | WO 97-22596 | 6/1997 |
| WO | WO 97-32856 | 9/1997 |
| WO | WO 98-02434 | 1/1998 |
| WO | WO 98-02437 | 1/1998 |
| WO | WO 98-02438 | 1/1998 |
| WO | WO 98-03516 | 1/1998 |
| WO | WO 98-07697 | 2/1998 |
| WO | WO 98-14451 | 4/1998 |
| WO | WO 98-16654 | 4/1998 |
| WO | WO 98-24893 | 6/1998 |
| WO | WO 98-30566 | 7/1998 |
| WO | WO 98-33768 | 8/1998 |
| WO | WO 98-34915 | 8/1998 |
| WO | WO 98-34918 | 8/1998 |
| WO | WO 98-50356 | 11/1998 |
| WO | WO 98-50433 | 11/1998 |
| WO | WO 98-54093 | 12/1998 |
| WO | WO 99-07675 | 2/1999 |
| WO | WO 99-10349 | 3/1999 |
| WO | WO 99-16755 | 4/1999 |
| WO | WO 99-24440 | 5/1999 |
| WO | WO 99-29667 | 6/1999 |
| WO | WO 99-35132 | 7/1999 |
| WO | WO 99-35146 | 7/1999 |
| WO | WO 99-45031 | 9/1999 |
| WO | WO 99-52889 | 10/1999 |
| WO | WO 99-52910 | 10/1999 |
| WO | WO 99-53049 | 10/1999 |
| WO | WO 99-61422 | 12/1999 |
| WO | WO 99-62890 | 12/1999 |
| WO | WO 00-09560 | 2/2000 |
| WO | WO 00-37504 | 6/2000 |
| WO | WO 00-50067 | 8/2000 |
| WO | WO 00-56772 | 9/2000 |
| WO | WO 05-016970 | 2/2005 |

OTHER PUBLICATIONS

Abuzzahab et al., "IGF-I Receptor Mutations Resulting in Intrauterine and Postnatal Growth Retardation," *The New England Journal of Medicine*, 349:2211-2222 (2003).

Adams et al., "Structure and function of the type 1 insulin-like growth factor receptor," *CMLS*, 57:1050-1093 (2000).

Altschul et al., "Basic local alignment search tool," *Journal of Molecular Biology*, 215(1):403-410 (1990).

Altschul et al., "Gapped BLAST and PSI-BLAST: a new generation of protein database search programs," *Nucleic Acids Research*, 25(17):3389-402 (1997).

Arteaga et al., "Blockade of the type I somatomedin receptor inhibits growth of human breast cancer cells in athymic mice," *Journal of Clinical Investigation*, 84:1418-1423 (1989).

Arteaga et al., "Interference of the IGF system as a strategy to inhibit breast cancer growth," *Breast Cancer Research Treatment*, 22:101-106 (1992).

Barbas et al., "Assembly of combinatorial antibody libraries on phage surfaces: the gene III site," *PNAS*, 88:7978-7982 (1991).

(56) References Cited

OTHER PUBLICATIONS

Barkan, "New options for diagnosing and treating acromegaly," *Cleveland Clinic Journal of Medicine*, 65(7):343-349 (1998).
Baserga, "The contradictions of the insulin-like growth factor 1 receptor," *Oncogene*, 19:5574-5581 (2000).
Bayes-Genis et al., "The insulin-like growth factor axis. A review of atherosclerosis and restenosis," *Circulation Research*, 86(2):125-130 (2000).
Bendig, M. M., "Humanization of Rodent Monoclonal Antibodies by CDR Grafting," *Methods: A Companion to Methods in Enzymology* 8:83-93 (1995).
Berzofsky, J.A. et al, "Immunogenicity and Antigen Structure" (from Chapter 8), Paul, W.E., ed., *Fundamental Immunology, 3rd Edition*, p. 242 (1993).
Bird et al., "Single-chain antigen-binding proteins," *Science*, 242:423-426 (1988).
Bohula et al., "Targeting the type 1 insulin-like growth factor receptor as anti-cancer treatment," *Anticancer Drugs*, 14:669-682(2003).
Bosch-Barrera et al., "Insulin and insulin-like growth factor pathway, a new targeted therapy in oncology," An Sist Sanit Navar 32(3):413-421 (2009) (with English abstract).
Bowie et al., "A method to identify protein sequences that fold into a known three-dimensional structure," *Science*, 253:164-170 (1991).
Burfeind et al., "Antisense RNA to the type I insulin-like growth factor receptor suppresses tumor growth and prevents invasion by rat prostate cancer cells in vivo," *Proc. Natl. Acad. Sci.*, 93:7263-7268 (1996).
Butler et al., "Stimulation of tumor growth by recombinant human insulin-like growth factor-I (IGF-I) is dependent on the dose and the level of IGF-I receptor expression," *Cancer Research*, 58:3021-3027 (1998).
Caldas et al., "Humanization of the anti-CD18 antibody 6.7: an unexpected effect of a framework residue in binding to antigen," *Molecular Immunology*, 39(15):941-952 (2003).
Casset, F. et al., "A peptide mimetic of an anti-CD4 monoclonal antibody by rational design," *Biochemical and Biophysical Research Communications* 307:198-205 (2003).
Chien et al., "Significant structural and functional change of an antigen-binding site by a distant amino acid substitution: proposal of a structural mechanism," *Proc. Natl. Acad. Sci. USA*, 86(14):5532-5536 (1989).
Chothia et al., "Canonical structures for the hypervariable regions of immunoglobulins," *Journal of Molecular Biology*, 196:901-917 (1987).
Chothia et al., "Conformations of immunoglobulin hypervariable regions," *Nature*, 342:877-883 (1989).
Clackson et al., "Making antibody fragments using phage display libraries," *Nature*, 352:624-628 (1991).
Cohen et al., "Combination therapy enhances the inhibition of tumor growth with the fully human anti-type 1 insulin-like growth factor receptor monoclonal antibody CP-751,871," *Clinical Cancer Research*, 11:2063-2073 (2005).
Colman, P.M., "Effects of amino acid sequence changes on antibody-antigen interactions," *Research in Immunology* 145:33-36 (1994).
Cullen et al., "Glutathione S-transferase π amplification is associated with cisplatin resistance in head and neck squamous cell carcinoma cell lines and primary tumors," *Cancer Research*, 63: 8097-8102 (2003).
Cullen et al., "Insulin-like growth factor receptor expression and function in human breast cancer," *Cancer Research*, 50: 48-53 (1990).
D'Ambrosio et al., A soluble insulin-like growth factor I receptor that induces apoptosis of tumor cells in vivo and inhibits tumorigenesis, *Cancer Research*, 56:4013-4020 (1996).
Daniel et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity is Drastically Influenced by the Nature of the Protein Carrier," *Virology*, 202:540-549 (1994).

DiGiovanni et al., "Deregulated expression of insulin-like growth factor 1 in prostate epithelium leads to neoplasia in transgenic mice," *PNAS*, 97(7):3455-3460 (2000).
Drexhage et al., "Endocrine autoimmune diseases," *Netherlands Journal of Medicine*, 45:285-293 (1994).
Dricu et al., "Expression of the Insulin-Like Growth Factor 1 Receptor (IGF-1R) in Breast Cancer Cells: Evidence for a Regulatory Role of Dolichyl Phosphate in the Transition from an Intracellular to an Extracellular IGF-1 Pathway," *Glycobiology* 9(6):571-579 (1999).
Du Pasquier, "Evolution of the immune system," *Fundamental Immunology, Second Edition*, edited by William E. Paul, Raven Press Ltd., NY, 139-165 (1989).
Dunn et al., "A dominant negative mutant of the insulin-like growth factor-I receptor inhibits the adhesion, invasion, and metastasis of breast cancer," *Cancer Research*, 58:3353-3361 (1998).
Elgert, "Immunology: Understanding the Immune System," The Genetic Basis of Antibody Diversity (1996), p. 123, Wiley-Liss, Inc., New York, NY.
Elagib et al , "Immunoglobulin variable genes and epitope recognition of human monoclonal anti-Ro 52-kd in primary Sjögren's syndrome," Arthritis and Rheumatism 42(11):2471-2481 (1999).
European Medicines Agency, "Prolia: EPAR—Product Information," Nov. 21, 2012.
European Medicines Agency, "Xgeva: EPAR—Product Information," Sep. 11, 2012.
Evans et al., "Design of nonpeptidal ligands for a peptide receptor: cholecystokinin antagonists," Journal of Medicinal Chemistry, 30:1229-1239 (1987).
Fagerstam et al., "Detection of antigen-antibody interactions by surface plasmon resonance. Applications to epitope mapping," *Journal of Molecular Recognition*, 3:(5,6):208-214 (1990).
Fanger et al., "Production and use of anti-FcR bispecific antibodies," *Immunomethods*, 4:72-81 (1994).
Fauchere, "Elements for the rational drug design of peptides drugs," *Advances in Drug Research*, 15:29-69 (1986).
Foekens et al., "Prognostic value of receptors for insulin-like growth factor 1, somatostatin, and epidermal growth factor in human breast cancer," *Cancer Research*, 49:7002-7009 (1989).
Freed et al., "Insulin-like growth factor-I and its autocrine role in growth of MCF-7 human breast cancer cells in culture," *Journal of Molecular Endocrinology*, 3:183-189 (1989).
Fuchs et al., "Targeting recombinant antibodies to the surface of *Escherichia coli*: fusion to a peptidoglycan associated lipoprotein," *Biotechnology*, 9:1369-1372 (1991).
Furlanetto et al., "Effects of insulin-like growth factor receptor inhibition on human melanomas in culture and in athymic mice," *Cancer Research*, 53:2522-2526 (1993).
Galfre et al., "Preparation of monoclonal antibodies: strategies and procedures," *Methods in Enzymology*, 73:3-46 (1981).
Garrad et al., "$F_{AB}$ assembly and enrichment in a monovalent phage display system," *Biotechnology*, 9:1373-1377 (1991).
George et al., "Differential Effects of Anti-$\beta_2$-Glycoprotein I Antibodies on Endothelial Cells and on the Manifestations of Experimental Antiphospholipid Syndrome," *Circulation*, 97:900-906 (1998).
Geran et al., "Protocols for screening chemical agents and natural products against animal tumors and other biological systems," *Cancer Chemotherapy Reports*, 3(2):1-104 (1972).
Giusti et al., "Somatic diversification of S107 from an antiphosphocholine to an anti-DNA autoantibody is due to a single base change in its heavy chain variable region," *Proc. Natl. Acad. Sci. USA*, 84(9):2926-2930 (1987).
Goldring et al., "Cytokines and cell growth control," *Critical Reviews in Eukaryotic Gene Expression*, 1:31-326 (1991).
Gonnet et al., "Exhaustive matching of the entire protein sequence database," *Science*, 256:1443-1445 (1992).
Gram et al., "In vitro selection and affinity maturation of antibodies from a naive combinatorial immunoglobulin library," *PNAS*, 89:3576-3580 (1992).
Green et al., "Antigen-specific human monoclonal antibodies from mice engineered with human Ig heavy and light chain YACs," *Nature Genetics*, 7:13-21 (1994).

(56) References Cited

OTHER PUBLICATIONS

Green et al., "Regulation of B cell development by variable gene complexity in mice reconstituted with human immunoglobulin yeast artificial chromosomes," *Journal of Experimental Medicine*, 188(3):483-495 (1998).
Greenspan et al., "Defining epitopes: it's not as easy as it seems," *Nature Biotechnology*, 17:936-937 (1999).
Griffiths et al., "Human anti-self antibodies with high specificity from phage display libraries," *The EMBO Journal*, 12(2):725-734 (1993).
Grimberg et al., "Role of insulin-like growth factors and their binding proteins in growth control and carcinogenesis," *Journal of Cellular Physiology*, 183:1-9 (2000).
Groves et al., "Production of an ovine monoclonal antibody to testosterone by an interspecies fusion," *Hybridoma* 6(1):71-76 (1987).
Guo et al., "Characterization of insulinlike growth factor I receptors in human colon cancer," *Gastroenterology*, 102(4):1101-1108 (1992).
Gussow et al., "Humanization of Monoclonal Antibodies," *Methods in Enzymology*, 203:99-121 (1991).
Harrington et al., "c-Myc-induced apoptosis in fibroblasts is inhibited by specific cytokines," *The EMBO Journal*, 13(14):3286-3295 (1994).
Hawkins et al., "Selection of phage antibodies by binding affinity mimicking affinity maturation," *Journal of Molecular Biology*, 226:889-896 (1992).
Hay et al., "Bacteriophage cloning and *Escherichia coli* expression of a human IgM Fab," *Hum. Antibod. Hybridomas*, 3:81-85 (1992).
Hermanto et al., "Inhibition of Mitogen-activated Protein Kinase Kinase Selectivity Inhibits Cell Proliferation in Human Breast Cancer Cells Displaying Enhanced Insulin-like Growth Factor I-mediated Mitogen-activated Protein Kinase Activation," *Cell Growth & Differentiation*, 11:655-664 (2000).
Hockenbery et al., "Bcl-2 is an inner mitochondrial membrane protein that blocks programmed cell *death*," *Nature*, 348:334-336 (1990).
Holliger et al., "Diabodies: small bivalent and bispecific antibody fragments," *PNAS*, 90:6444-6448 (1993).
Holm et al., "Functional mapping and single chain construction of the anti-cytokeratin 8 monoclonal antibody TS1," *Molecular Immunology*, 44(6):1075-1084 (2007).
Hoogenboom et al., "Multi-subunit proteins on the surface of filamentous phage: methodologies for displaying antibody (Fab) heavy and light chains," *Nucleic Acids Research*, 19(15):4133-4137 (1991).
Huse et al., "Generation of a large combinatorial library of the immunoglobulin repertoire in phage lambda," *Science*, 246:1275-1281 (1989).
Huston et al., "Protein engineering of antibody binding sites: recovery of specific activity in an anti-digoxin single-chain Fv analogue produced in *Escherichia coli*," *PNAS*, 85:5879-5883 (1988).
Ill et al., "Design and construction of a hybrid immunoglobulin domain with properties of both heavy and light chain variable regions," *Protein Engineering*, 10(8): 949-957 (1997).
Jiang et al., "A Novel Peptide Isolated from a Phage Display Peptide Library with Trastuzumab Can Mimic Antigen Epitope of HER-2," *Journal of Biological Chemistry*, 280(6):4656-4662 (2005).
Jiang et al., "Induction of tumor suppression and glandular differentiation of A549 lung carcinoma cells by dominant-negative IGF-I receptor," *Oncogene*, 18:6071-6077 (1999).
Johnsson et al., "Comparison of methods for immobilization to carboxymethyl dextran sensor surfaces by analysis of the specific activity of monoclonal antibodies," *Journal of Molecular Recognition*, 8:125-131 (1995).
Johnsson et al, "Immobolization of proteins to a carboxymethyldextran-modified gold surface for biospecific interaction analysis in surface plasmon resonance sensors," *Analytical Biochemistry*, 198:268-277 (1991).
Jonsson et al., "Introducing a biosensor based technology for real-time biospecific interaction analysis," *Ann. Biologie Clinique.*, 51:19-26 (1993).
Jonsson et al., "Real-time biospecific interaction analysis using surface plasmon resonance and a sensor chip technology," *BioTechniques*, 11(5):620-627 (1991).
Kaiser et al., "Expression of insulin-like growth factor receptors I and II in normal human lung and in lung cancer," *Journal of Cancer Research and Clinical Oncology*, 119(11):665-668 (1993).
Kalebic et al., "In vivo treatment with antibody against IGF-I receptor suppresses growth of human rhabdomyosarcoma and down-regulates p34$^{cdc2}$," *Cancer Research*, 54:5531-5534 (1994).
Kaliman et al., "Antipeptide Antibody to the Insulin-Like Growth Factor-I Receptor Sequence 1232-1246 Inhibits the Receptor Kinase Activity," *The Journal of Biological Chemistry* 267(15):10645-10651 (1992).
Kato, "Role of tyrosine kinase activity in signal transduction by the insulin-like growth factor-I (IGF-I) receptor," *Journal of Biological Chemistry*, 268:2655-2661 (1993).
Kim et al., "Insulin receptor substrate 2 and Shc play different roles in insulin-like growth factor I signaling," *Journal of Biological Chemistry*, 273:34543-34550 (1998).
Lahm et al., "Blockade of the insulin-like growth-factor-I receptor inhibits growth of human colorectal cancer cells: evidence of a functional IGF-II-mediated autocrine loop," *International Journal of Cancer*, 58:452-459 (1994).
Lamm et al., "Impairment of survival factor function potentiates chemotherapy-induced apoptosis in tumor cells," *Cancer Research*, 58:801-807 (1998).
Lane, "A death in the life of p53," *Nature*, 362:786-787 (1993).
Laplanche et al., "Phosphorothiolate-modified oligodeoxyribonucleotides, III. NMR and UV spectroscopic studies of the $R_p$-$R_p$, $S_p$-$S_p$, and $R_p$-$S_p$ duplexes, [d(GG$_5$AATTCC)]$_2$, derived from diastereomeric O-ethyl phosphorothioates," *Nucleic Acids Research*, 14(22):9081-9093 (1986).
Laron, "Clinical use of somatomedin-1," *Pediatric Drugs*, 1(3):155-159 (1999).
Leroith et al., "Molecular and cellular aspects of the insulin-like growth factor I receptor," *Endocrine Reviews*, 16(2):143-163 (1995).
Li et al., "Mitogenicity and transforming activity of the insulin-like growth factor-I receptor with mutations in the tyrosine kinase domain," *Journal of Biological Chemistry*, 269:32558-32564 (1994).
Li et al., "Two new monoclonal antibodies against the α subunit of the human insulin-like growth factor-I receptor," *Biochemical and Biophysical Research Communications*, 196(1):92-98 (1993).
Li, S.-L. et al., "Single-chain Antibodies Against Human Insulin-like Growth Factor I Receptor: Expression, Purification and Effect on Tumor Growth," *Cancer Immunology and Immunotherapy*, 49:243-252 (2000).
Macaulay, "Insulin-like growth factors and cancer," *British Journal of Cancer*, 65:311-320 (1992).
Macauley et al., "Autocrine function for insulin-like growth factor I in human small cell lung cancer cell lines and fresh tumor cells," *Cancer Research*, 50:2511-2517 (1990).
MacCallum, R.M. et al., "Antibody-antigen Interactions: Contact Analysis and Binding Site Topography," *Journal of Molecular Biology* 262:732-745 (1996).
Mariuzza et al., "The Structural Basis of Antigen-Antibody Recognition," *Annu. Rev. Biophys. Biophys. Chem.*, 16:139-159 (1987).
Martin et al., "The affinity-selection of a minibody polypeptide inhibitor of human interleukin-6," *The EMBO Journal*, 13(22): 5303-5309 (1994).
McCafferty et al., "Phage antibodies: filamentous phage displaying antibody variable domains," *Nature*, 348:552-554 (1990).
McDonnell et al., "bcl-2-immunoglobulin transgenic mice demonstrate extended B cell survival and follicular lymphoproliferation," *Cell*, 57:79-88 (1989).
Mendez et al., "Functional transplant of megabase human immunoglobulin loci recapitulates human antibody response in mice," *Nature Genetics*, 15:146-156 (1997).
Moody et al., "Growth factor and peptide receptors in small cell lung cancer," *Life Sciences*, 52:1161-1173 (1993).

(56) References Cited

OTHER PUBLICATIONS

Moyer et al., "Induction of apoptosis and cell cycle arrest by CP-358,774, an inhibitor of epidermal growth factor receptor tyrosine kinase," *Cancer Research*, 57:4838-4848 (1997).
Nakanishi et al., "Insulin-like growth factor-I can mediate autocrine proliferation of human small cell lung cancer cell lines in vitro," *Journal of Clinical Investigation*, 82:354-359 (1988).
NCBI Entrez Protein Database, Search Results for "insulin-like growth factor I receptor," Aug. 26, 2008.
Paul, "Chapter B: Immunogenicity and Antigen Structure," *Fundamental Immunology*, (3d ed.) p. 242 (1993).
Paul, W.E., Ed., "Structure and Function of Immunoglobulins," *Fundamental Immunology, 3rd Edition*, 292-295 (1993).
Pearson, "Effective protein sequence comparison," *Methods in Enzymology*, 266:227-258 (1996).
Pearson, "Empirical statistical estimates for sequence similarity searches," *Journal of Molecular Biology*, 276:71-84 (1998).
Pearson, "Flexible sequence similarity searching with the FASTA3 program package," *Methods in Molecular Biology*, 132:185-219 (2000).
Pearson, "Rapid and sensitive sequence comparison with FASTP and FASTA," *Methods in Enzymolology*, 183:63-98 (1990).
Pearson, "Using the FASTA program to search protein and DNA sequence databases," *Methods in Molecular Biology*, 24:307-331 (1994).
Pietrzkowski et al., "Constitutive expression of insulin-like growth factor 1 and insulin-like growth factor 1 receptor abrogates all requirements for exogenous growth factors," *Cell Growth & Differentiation*, 3:199-205 (1992).
Pietrzkowski et al., "Roles of insullike growth factor 1 (IGF-1) and the IGF-1 receptor in epidermal growth factor-stimulated growth of 3T3 cells," *Molecular and Cellular Biology*, 12(9):3883-3889 (1992).
Poljak, "Production and structure of diabodies," *Structure*, 2:1121-1123 (1994).
Pollack et al, "Inhibition of epidermal growth factor receptor-associated tyrosine phosphorylation in human carcinomas with CP-358,774: Dynamics of receptor inhibition in situ and antitumor effects in athymic mice," *Journal of Pharmacology and Experimental Therapeutics*, 291(2):739-748 (1999).
Pollack et al., "Presence of somatomedin receptors on primary human breast and colon carcinomas," *Cancer Letters*, 38:223-230 (1987).
Prager et al., "Dominant negative inhibition of tumorigensis in vivo by human insulin-like growth factor I receptor mutant," *PNAS*, 91:2181-2185 (1994.
Remacle-Bonnet et al., "Expression of Type I, but not Type II insulin-like growth factor receptor on both undifferentiated and differentiated HT29 human colon carcinoma cell line," *Journal of Clinical Endocrinology and Metabolism*, 75(2):609-616 (1992).
Resnicoff et al., "Correlation between apoptosis, tumorigenesis, and levels of insulin-like growth factor I receptors," *Cancer Research*, 55:3739-3741 (1995).
Resnicoff et al., "Growth inhibition of human melanoma cells in nude mice by antisense strategies to the type 1 insulin-like growth factor receptor," *Cancer Research*, 54:4848-4850 (1994).
Resnicoff et al., "The insulin-like growth factor I receptor protects tumor cells from Apoptosis in vivo," *Cancer Research*, 55:2463-2469 (1995).
Rico et al., "Cuantificacíon del factor de crecimiento similar a la insulin (IGF-I) total en tejidos de rata," Biomedica 18(2):129-133 (1998) (with English abstract).
Riechmann et al., "Reshaping human antibodies for therapy," Nature 332:323-327 (1988).
Rizo et al., "Constrained peptides: models of bioactive peptides and protein substructures," *Annual Review of Biochemistry*, 61:387-418 (1992).
Rodriguez-Tarduchy et al., "Insulin-like growth factor-I inhibits apoptosis in Il-3-dependent hemopoietic cells," *Journal of Immunology*, 149(2):535-540 (1992).
Rosen et al., "Circulating IGF-I: new perspectives for a new century," *Trends in EndocrinologyMetabolism*,10(4):136-141 (1999).
Rubini et al., "Characterization of an antibody that can detect an activated IGF-I receptor in human cancers," *Experimental Cell Research* 251(1):22-32 (1999).
Rudikoff, S. et al., "Single amino acid substitution altering antigen-binding specificity," *Proc. Natl. Acad. Sci., USA* 79:1979-1983 (1982).
Sachdev et al., "A chimeric humanized single-chain antibody against the type I insulin-like growth factor (IGF) receptor renders breast cancer cells refractory to the mitogenic effects of IGF-I," *Cancer Research*, 63:627-635 (2003).
Sandberg-Nordqvist et al., "Characterization of insulin-like growth factor 1 in human primary brain tumors," *Cancer Research*, 53:2475-2478 (1993).
Sell et al., "Insulin-like growth factor 1 (IGF-1) and the IGF-1 receptor prevent etoposide-induced apoptosis," *Cancer Research*, 55:303-306 (1995).
Smith et al., "Regulation of vascular endothelial growth factor-dependent retinal neovascularization by insulin-like growth factor-1 receptor," *Nature Medicine*, 5(12): 1390-1395 (1999).
Soos, "A panel of monoclonal antibodies for the type I insulin-like growth factor receptor," Journal of Biological Chemistry, 267:12955-12963 (1992).
Stancovski et al., "Mechanistic aspects of the opposing effects of monoclonal antibodies to the ERBB2 receptor on tumor growth," *Proc. Natl. Acad. Sci. USA*, 88:8691-8695 (1991).
Stec et al., "Automated solid-phase synthesis, separation, and stereochemistry of phosphorothioate analogues of oligodeoxyribonucleotides," *Journal of the American Chemical Society*, 106(20):6077-6079 (1984).
Steele-Perkins et al., "Monoclonal antibody αIR-3 inhibits the Ability of Insulin-Like Growth Factor II to Stimulate a Signal From the Type 1 Receptor Without Inhibiting is Binding," *Biochemical and Biophysical Research Communications* 171(3):1244-1251 (1990).
Stein et al., "Physiochemical properties of phosphorothioate oligodeoxynucleotides," *Nucleic Acids Research*, 16(8):3209-3221 (1988).
Tappy et al., "Antibodies to insulin-like growth factor 1 receptors in diabetes and other disorders," *Diabetes*, 37:1708-1714 (1988).
Thompson et al., "Low prevalence of autoantibodies to the insulin-like growth factor I receptor in children with short stature," *Pediatric Research*, 32(4):455-459 (1988).
Thornton et al., "Prediction of progress at last," *Nature*, 354(14):105-106 (1991).
Traunecker et al., "Bispecific single chain molecules (Janusins) target cytotoxic lymphocytes on HIV infected cells," *The EMBO Journal*, 10(12):3655-3659 (1991).
Traunecker et al., "Janusin: new molecular design for bispecific reagents," *International Journal of Cancer*, 7:51-52 (1992).
Trojan et al., "Treatment and prevention of rat glioblastoma by immunogenic C6 cells expressing antisense insulin-like growth factor 1 RNA," *Science*, 259:94-97 (1993).
Uhlmann et al., "Antisense oligonucleotides: a new therapeutic principle," *Chemical Reviews*, 90(4):543-584 (1990).
Ullrich et al., "Insulin-like growth factor I receptor primary structure: comparison with insulin receptor suggests structural determinants that define functional specificity," *The EMBO Journal*, 5(10):2503-2512 (1986).
Ullrich et al., "Signal transduction by receptors with tyrosine kinase activity," *Cell*, 61:203-212 (1990).
United States Patent and Trademark Office, "Notice of Allowance and Fee(s) Due," U.S. Appl. No. 11/144,222, Jun. 24, 2009.
United States Patent and Trademark Office, "Notice of Allowability," U.S. Appl. No. 11/144,222, Jun. 24, 2009.
United States Patent and Trademark Office, "Notice of Allowance and Fee(s) Due," U.S. Appl. No. 11/144,248, Dec. 30, 2009.
United States Patent and Trademark Office, "Notice of Allowability," U.S. Appl. No. 11/144,248, Dec. 30, 2009.
United States Patent and Trademark Office, "Notice of Allowance and Fee(s) Due," U.S. Appl. No. 12/756,417, Mar. 4, 2011.
United States Patent and Trademark Office, "Notice of Allowability," U.S. Appl. No. 12/756,417, Mar. 4, 2011.

(56) References Cited

OTHER PUBLICATIONS

United States Patent and Trademark Office, "Notice of Allowance and Fee(s) Due," U.S. Appl. No. 13/169,474, Sep. 26, 2013.
United States Patent and Trademark Office, "Notice of Allowability," U.S. Appl. No. 13/169,474, Sep. 26, 2013.
Veber et al., "The design of metabolically-stable peptide analogs," *TINS*, 8(9):392-396 (1985).
Wang et al , "Inhibition of insulin-like growth factor-I receptor (IGF-IR) signaling and tumor cell growth by a fully human neutralizing anti-IGF-IR antibody," *Molecular Cancer Therapeutics*, 4(8):1214-1221 (2005).
Ward et al., "Binding activities of a repertoire of single immunoglobulin variable domains secreted from *Escherichia coli*," *Nature*, 341:544-546 (1989).
Weightman et al., "Autoantibodies to IGF-1 binding sites in thyroid associated ophthalmopathy," *Autoimmunity*, 16:251-257 (1993).
Williams, "Programmed cell death: apoptosis and oncogenesis," *Cell*, 65:1097-1098 (1991).
Wing et al., "Ex-vivo whole blood cultures for predicting cytokine-release syndrome: dependence on target antigen and antibody isotype," *Ther. Immunol.*, 2:183-190 (1995).
Winkler et al., "Changing the Antigen Binding Specificity by Single Point Mutations of an Anti-p24 (HIV-1) Antibody," *The Journal of Immunology*, 165:4505-4514 (2000).
Winter et al., "Antibody-Based Therapy," TiPS 14:139-143 (1993).
Winter et al., "Humanized antibodies," *Immunology Today*, 14(6):243-246 (1993).
Wraight et al., "Reversal of epidermal hyperproliferation in psoriasis by insulin-like growth factor I receptor antisense oligonucleotides," *Nature Biotechnology*, 18:521-526 (2000).
Wright et al., "Genetically engineered antibodies: progress and prospects," *Critical Reviews in Immunology*, 12:(3,4)125-168 (1992).
Wu et al., "In vivo effects of the human type I insulin-like growth factor receptor antibody A12 on androgen-dependent and androgen-independent xenograft human prostate tumors," *Clinical Cancer Research*, 11(8) 3065-3074 (2005).
Xiong et al., "Growth-Stimulatory Monoclonal Antibodies Against Human Insulin-Like Growth Factor I Receptor," *Proceedings of the National Academy of Sciences of the USA* 89:5356-5360 (1992).
Yee et al., "Analysis of insulin-like growth factor 1 gene expression in malignancy: evidence for a paracrine role in human breast cancer," *Molecular Endocrinology*, 3(3):509-517 (1989).
Yee et al., "Insulin-like growth factor II mRNA expression in human breast cancer," *Cancer Research*, 48:6691-6696 (1988).
Zia et al., "Monoclonal antibody αIR-3 inhibits non-small cell lung cancer growth in vitro and in vivo," *Journal of Cellular Biochemistry*, S24:269-275 (1996).
Zon et al., "Phosphorothioate oligonucleotides," *Oligonucleotides and Analogues: A Practical Approach*, 87-108 (F. Eckstein, Ed., Oxford University Press, Oxford England (1991).
Zon et al., "Phosphorothioate oligonucleotides: chemistry, purification, analysis, scale-up and future directions," *Anti-Cancer Drug Design*, 6:539-568 (1991).

| | | | | | | |
|---|---|---|---|---|---|---|
| 2.13.2K | GACATCCAGA | TGACCCAGTT | TCCATCCTCC | CTGTCTGCAT | CTGTAGGAGA | 50 |
| A30 | GACATCCAGA | TGACCCAGTC | TCCATCCTCC | CTGTCTGCAT | CTGTAGGAGA | 50 |
| 2.14.3K | ---------- | ---------- | ----TCCTCC | CTGTCTGCAT | CTGTAGGAGA | 26 |
| 2.12.1K | ---------- | ---------- | ---------- | -----TGCAT | CTGTAGGAGA | 15 |
| 4.9.2K | GACATCCAGA | TGACCCAGTC | TCCATCCTCC | CTGTCTGCAT | CTGTAGGAGA | 50 |
| Consensus | GACATCCAGA | TGACCCAGTY | TCCATCCTCC | CTGTCTGCAT | CTGTAGGAGA | 50 |

CDR1

| | | | | | | |
|---|---|---|---|---|---|---|
| 2.13.2K | CAGAGTCACC | ATCACTTGCC | GGGCAAGTCA | GGGCATTAGA | AATGATTTAG | 100 |
| A30 | CAGAGTCACC | ATCACTTGCC | GGGCAAGTCA | GGGCATTAGA | AATGATTTAG | 100 |
| 2.14.3K | CAGAGTCACC | TTCACTTGCC | GGGCAAGTCA | GGACATTAGA | CGTGATTTAG | 76 |
| 2.12.1K | CAGAGTCACC | TTCACTTGCC | GGGCAAGTCA | GGACATTAGA | CGTGATTTAG | 65 |
| 4.9.2K | CAGAGTCACC | ATCACTTGCC | GGGCAAGTCA | GGGCATTAGA | AGTGATTTAG | 100 |
| Consensus | CAGAGTCACC | WTCACTTGCC | GGGCAAGTCA | GGRCATTAGA | MRTGATTTAG | 100 |

| | | | | | | |
|---|---|---|---|---|---|---|
| 2.13.2K | GCTGGTATCA | GCAGAAACCA | GGGAAAGCCC | CTAAGCGCCT | GATCTATGCT | 150 |
| A30 | GCTGGTATCA | GCAGAAACCA | GGGAAAGCCC | CTAAGCGCCT | GATCTATGCT | 150 |
| 2.14.3K | GCTGGTATCA | GCAGAAACCA | GGGAAAGCTC | CTAAGCGCCT | GATCTATGCT | 126 |
| 2.12.1K | GCTGGTATCA | GCAGAAACCA | GGGAAAGCTC | CTAAGCGCCT | GATCTATGCT | 115 |
| 4.9.2K | GCTGGTTTCA | GCAGAAACCA | GGGAAAGCCC | CTAAGCGCCT | GATCTATGCT | 150 |
| Consensus | GCTGGTWTCA | GCAGAAACCA | GGGAAAGCYC | CTAAGCGCCT | GATCTATGCT | 150 |

CDR2

| | | | | | | |
|---|---|---|---|---|---|---|
| 2.13.2K | GCATCCCGTT | TGCACAGAGG | GGTCCCATCA | AGGTTCAGCG | GCAGTGGATC | 200 |
| A30 | GCATCCAGTT | TGCAAAGTGG | GGTCCCATCA | AGGTTCAGCG | GCAGTGGATC | 200 |
| 2.14.3K | GCATCCCGTT | TACAAAGTGG | GGTCCCATCA | AGGTTCAGCG | GCAGTGGATC | 176 |
| 2.12.1K | GCATCCCGTT | TACAAAGTGG | GGTCCCATCA | AGGTTCAGCG | GCAGTGGATC | 165 |
| 4.9.2K | GCATCCAAAT | TACACGTGG | GGTCCCATCA | AGGTTCAGCG | GCAGTGGATC | 200 |
| Consensus | GCATCCMRWT | TRCAMMGWGG | GGTCCCATCA | AGGTTCAGCG | GCAGTGGATC | 200 |

| | | | | | | |
|---|---|---|---|---|---|---|
| 2.13.2K | TGGGACAGAA | TTCACTCTCA | CAATCAGCAG | CCTGCAGCCT | GAAGATTTTG | 250 |
| A30 | TGGGACAGAA | TTCACTCTCA | CAATCAGCAG | CCTGCAGCCT | GAAGATTTTG | 250 |
| 2.14.3K | TGGGACAGAA | TTCACTCTCA | CAATCAGCAG | CCTGCAGCCT | GAAGATTTTG | 226 |
| 2.12.1K | TGGGACAGAA | TTCACTCTCA | CAATCAGCAG | CCTGCAGCCT | GAAGATTTTG | 215 |
| 4.9.2K | TGGGACAGAA | TTCACTCTCA | CAATCAGCCG | CCTGCAGCCT | GAAGATTTTG | 250 |
| Consensus | TGGGACAGAA | TTCACTCTCA | CAATCAGCMG | CCTGCAGCCT | GAAGATTTTG | 250 |

CDR3

| | | | | | | |
|---|---|---|---|---|---|---|
| 2.13.2K | CAACTTATTA | CTGTTTACAA | CATAATAGTT | ACCGGTGCAG | TTTTGGCCAG | 300 |
| A30 | CAACTTATTA | CTGTCTACAG | CATAATAGTT | ACC-TCCN- | ---------- | 288 |
| 2.14.3K | CAACTTATTA | CTGTCTACAG | CATAATAATT | ATCCTCGGAC | GTTCGCCAA | 276 |
| 2.12.1K | CAACTTATTA | CTGTCTACAG | CATAATAATT | ATCCTCGGAC | GTTCGGCCAA | 265 |
| 4.9.2K | CAACTTATTA | CTGTCTACAG | CATAATAGTT | ACCTCTCAC | TTTCGGCGGA | 300 |
| Consensus | CAACTTATTA | CTGTYTACAR | CATAATARTT | AYCKYBSNS | KTTYGGCSRR | 300 |

| | | | | | |
|---|---|---|---|---|---|
| 2.13.2K | GGGACCAAGC | TGGAGATCAA | AC---- | | 322 |
| A30 | ---------- | ---------- | ------ | | 288 |
| 2.14.3K | GGGACCGAGG | TGGAAATCAT | ACGAAC | | 302 |
| 2.12.1K | GGGACCGAGG | TGGAAATCAT | ACGAAC | | 291 |
| 4.9.2K | GGGACCAAGG | TGGAGATCAA | AC---- | | 322 |
| Consensus | GGGACCRAGS | TGGARATCAW | ACGAAC | | 326 |

FIG. 1A

```
4.17.3K     ---------- ---------- ---------- ---------- ----AGGAGA    7
O12         GACATCCAGA TGACCCAGTC TCCATCCTCC CTGTCTGCAT CTGTAGGAGA   50
Consensus   GACATCCAGA TGACCCAGTC TCCATCCTCC CTGTCTGCAT CTGYAGGAGA   50
                                                              CDR1
4.17.3K     CAGAGTCACC ATCACTTGCC GGGCAAGTCA GAGCATTAGT ACCTTTTTAA   57
O12         CAGAGTCACC ATCACTTGCC GGGCAAGTCA GAGCATTAGC AGCTATTTAA  100
Consensus   CAGAGTCACC ATCACTTGCC GGGCAAGTCA GAGCATTAGY ASCTWTTTAA  100

4.17.3K     ATTGGTATCA GCAGAAACCA GGGAAAGCCC CTAAACTCCT GATCCATGTT  107
O12         ATTGGTATCA GCAGAAACCA GGGAAAGCCC CTAAGCTCCT GATCTATGCT  150
Consensus   ATTGGTATCA GCAGAAACCA GGGAAAGCCC CTAARCTCCT GATCYATGYT  150
                CDR2
4.17.3K     GCATCCAGTT TACAAGGTGG GGTCCCATCA AGGTTCAGTG GCAGTGGATC  157
O12         GCATCCAGTT TGCAAAGTGG GGTCCCATCA AGGTTCAGTG GCAGTGGATC  200
Consensus   GCATCCAGTT TRCAARGTGG GGTCCCATCA AGGTTCAGTG GCAGTGGATC  200

4.17.3K     TGGGACAGAT TTCACTCTCA CCATCAGCAG TCTGCAACCT GAAGATTTTG  207
O12         TGGGACAGAT TTCACTCTCA CCATCAGCAG TCTGCAACCT GAAGATTTTG  250
Consensus   TGGGACAGAT TTCACTCTCA CCATCAGCAG TCTGCAACCT GAAGATTTTG  250
                                                       CDR3
4.17.3K     CAACTTACTA CTGTCAACAG AGTTACAATG CCCCACTCAC TTTCGGCGGA  257
O12         CAACTTACTA CTGTCAACAG AGTTACACTA CCCC-TCCH- ----------  288
Consensus   CAACTTACTA CTGTCAACAG AGTTACARTR CCCCAYYCHC TTTCGGCGGA  300

4.17.3K     GGGACCAAGG TGGAGATCAA AC                                 279
O12         ---------- ---------- --                                 288
Consensus   GGGACCAAGG TGGAGATCAA AC                                 322
```

FIG. 1B

```
                                                             CDR1
6.1.1K                                                  ──────────
A27       GAAATTGTGT TGACGCAGTC TCCAGGCACC CTGTCTTTGT CTCCAGGGGA    50
Consensus GAAATTGTGT TGACGCAGTC TCCAGGCACC CTGTCTTTGT CTCCAGGGGA    50

6.1.1K    -AGAGCCACC CTCTCCTGTA GGGCCAGTCA GAGTGTTCGC GGCAGGTACT    49
A27       AAGAGCCACC CTCTCCTGCA GGGCCAGTCA GAGTGTTAGC AGCAGCTACT   100
Consensus AAGAGCCACC CTCTCCTGYA GGGCCAGTCA GAGTGTTMGC RGCAGSTACT   100

6.1.1K    TAGCCTGGTA CCAGCAGAAA CCTGGCCAGG CTCCCAGGCT CCTCATCTAT    99
A27       TAGCCTGGTA CCAGCAGAAA CCTGGCCAGG CTCCCAGGCT CCTCATCTAT   150
Consensus TAGCCTGGTA CCAGCAGAAA CCTGGCCAGG CTCCCAGGCT CCTCATCTAT   150
               CDR2
          ──────────────────────
6.1.1K    GGTGCATCCA GCAGGGCCAC TGGCATCCCA GACAGGTTCA GTGGCAGTGG   149
A27       GGTGCATCCA GCAGGGCCAC TGGCATCCCA GACAGGTTCA GTGGCAGTGG   200
Consensus GGTGCATCCA GCAGGGCCAC TGGCATCCCA GACAGGTTCA GTGGCAGTGG   200

6.1.1K    GTCTGGGACA GACTTCACTC TCACCATCAG CAGACTGGAG CCTGAAGATT   199
A27       GTCTGGGACA GACTTCACTC TCACCATCAG CAGACTGGAG CCTGAAGATT   250
Consensus GTCTGGGACA GACTTCACTC TCACCATCAG CAGACTGGAG CCTGAAGATT   250
                                           CDR3
                                       ──────────────
6.1.1K    TTGCAGTGTT TTACTGTCAG CAGTATGGTA GTTCACCTCG NACGTTCGGC   249
A27       TTGCAGTGTA TTACTGTCAG CAGTATGGTA GCTCACCTCC ----------   290
Consensus TTGCAGTGTW TTACTGTCAG CAGTATGGTA GYTCACCTCS NACGTTCGGC   300

6.1.1K    CAAGGGACCA AGGTGGAAAT CAAAC                              274
A27       ---------- ---------- -----                              290
Consensus CAAGGGACCA AGGTGGAAAT CAAAC                              325
```

FIG. 1C

```
2.12.1H      ---------- ---------- ---GGGAGGC TTGGTCAAGC CTGGA-GGTC    26
DP35         CAGGTGCAGC TGGTGGAGTC TGGGGGAGGC TTGGTCAAGC CTGGAGGGTC    50
Consensus    CAGGTGCAGC TGGTGGAGTC TGGGGGAGGC TTGGTCAAGC CTGGAGGGTC    50
                                                              CDR1

2.12.1H      CCTGAGACTC TCCTGTGCAG CCTCTGGATT CACTTTCAGT GACTACTATA    76
DP35         CCTGAGACTC TCCTGTGCAG CCTCTGGATT CACCTTCAGT GACTACTACA   100
Consensus    CCTGAGACTC TCCTGTGCAG CCTCTGGATT CACYTTCAGT GACTACTAYA   100

2.12.1H      TGAGCTGGAT CCGCCAGGCT CCAGGGAAGG GGCTGGAATG GGTTTCATAC   126
DP35         TGAGCTGGAT CCGCCAGGCT CCAGGGAAGG GGCTGGAGTG GGTTTCATAC   150
Consensus    TGAGCTGGAT CCGCCAGGCT CCAGGGAAGG GGCTGGARTG GGTTTCATAC   150
                              CDR2

2.12.1H      ATTAGTAGTA GTGGTAGTAC CAGAGACTAC GCAGACTCTG TGAAGGGCCG   176
DP35         ATTAGTAGTA GTGGTAGTAC CATATACTAC GCAGACTCTG TGAAGGGCCG   200
Consensus    ATTAGTAGTA GTGGTAGTAC CAKAKACTAC GCAGACTCTG TGAAGGGCCG   200

2.12.1H      ATTCACCATC TCCAGGGACA ACGCCAAGAA CTCACTGTAT CTGCAAATGA   226
DP35         ATTCACCATC TCCAGGGACA ACGCCAAGAA CTCACTGTAT CTGCAAATGA   250
Consensus    ATTCACCATC TCCAGGGACA ACGCCAAGAA CTCACTGTAT CTGCAAATGA   250

2.12.1H      ACAGCCTGAG AGCCGAGGAC ACGGCCGTGT ATTACTGTGT GAGAGATGGA   276
DP35         ACAGCCTGAG AGCCGAGGAC ACGGCCGTGT ATTACTGTGC GAGAGA----   296
Consensus    ACAGCCTGAG AGCCGAGGAC ACGGCCGTGT ATTACTGTGY GAGAGATGGA   300
                                                       CDR3

2.12.1H      GTGGAAACTA CTTTTTACTA CTACTACTAC GGTATGGACG TCTGGGGCCA   326
DP35         ---------- ---------- ---------- ---------- ----------   296
Consensus    GTGGAAACTA CTTTTTACTA CTACTACTAC GGTATGGACG TCTGGGGCCA   350

2.12.1H      AGGGACCACG GTCACCGTCT CCTCAG                             352
DP35         ---------- ---------- ------                             296
Consensus    AGGGACCACG GTCACCGTCT CCTCAG                             376
```

FIG. 2A

```
PF2-2.14.3H.DNA  ---------- ----------  GGGCCCAGGA CTGGTGAAGC CTTCGGAGAC   30
VIV-4/4.35       CAGGTGCAGC TGCAGGAGTC  GGGCCCAGGA CTGGTGAAGC CTTCGGAGAC   50
Consensus        CAGGTGCAGC TGCAGGAGTC  GGGCCCAGGA CTGGTGAAGC CTTCGGAGAC   50
                                                                     CDR1

PF2-2.14.3H.DNA  CCTGTCCCTC ACCTGCACTG TCTCTGGTGG CTCCATCAGT AATTACTACT    80
VIV-4/4.35       CCTGTCCCTC ACCTGCACTG TCTCTGGTGG CTCCATCAGT AGTTACTACT   100
Consensus        CCTGTCCCTC ACCTGCACTG TCTCTGGTGG CTCCATCAGT ARTTACTACT   100
                 CDR1

PF2-2.14.3H.DNA  GGAGCTGGAT CCGGCAGCCC GCCGGGAAGG GACTGGAGTG GATTGGGCGT   130
VIV-4/4.35       GGAGCTGGAT CCGGCAGCCC GCCGGGAAGG GACTGGAGTG GATTGGGCGT   150
Consensus        GGAGCTGGAT CCGGCAGCCC GCCGGGAAGG GACTGGAGTG GATTGGGCGT   150
                       CDR2

PF2-2.14.3H.DNA  ATCTATACCA GTGGGAGCCC CAACTACAAC CCCTCCCTCA AGAGTCGAGT   180
VIV-4/4.35       ATCTATACCA GTGGGAGCAC CAACTACAAC CCCTCCCTCA AGAGTCGAGT   200
Consensus        ATCTATACCA GTGGGAGCMC CAACTACAAC CCCTCCCTCA AGAGTCGAGT   200

PF2-2.14.3H.DNA  CACCATGTCA GTAGACACGT CCAAGAACCA GTTCTCCCTG AAGCTGAACT   230
VIV-4/4.35       CACCATGTCA GTAGACACGT CCAAGAACCA GTTCTCCCTG AAGCTGAGCT   250
Consensus        CACCATGTCA GTAGACACGT CCAAGAACCA GTTCTCCCTG AAGCTGARCT   250

PF2-2.14.3H.DNA  CTGTGACCGC CGCGGACACG GCCGTGTATT ACTGTGCGGT AACGATTTTT   280
VIV-4/4.35       CTGTGACCGC CGCGGACACG GCCGTGTATT ACTGTGCG-- ----------   288
Consensus        CTGTGACCGC CGCGGACACG GCCGTGTATT ACTGTGCGGT AACGATTTTT   300
                         CDR3

PF2-2.14.3H.DNA  GGAGTGGTTA TTATCTTTGA CTACTGGGGC CAGGGAACCC TGGTCACCGT   330
VIV-4/4.35       ---------- ---------- ---------- -AGAGAB--- ----------   294
Consensus        GGAGTGGTTA TTATCTTTGA CTACTGGGGC CAGRGANCCC TGGTCACCGT   350

PF2-2.14.3H.DNA  CTCCTCAG                                                  338
VIV-4/4.35       --------                                                  294
Consensus        CTCCTCAG                                                  358
```

FIG. 2B

| | | |
|---|---|---|
| 6.1.1H   | GAGGTGCAGC TGTTGGAGTC TGGGGGAGGC TTGGTACAGC CTGGGGGGTC | 50 |
| 4.9.2H   | GAGGTGCAGC TGTTGGAGTC TGGGGGAGGC TTGGTACAGC CTGGGGGGTC | 50 |
| DP47     | GAGGTGCAGC TGTTGGAGTC TGGGGGAGGC TTGGTACAGC CTGGGGGGTC | 50 |
| 2.13.2H  | GAGGTGCAGC TGTTGGAGTC TGGGGGAGGC TTGGTACAGC CTGGGGGGTC | 50 |
| Consensus| GAGGTGCAGC TGTTGGAGTC TGGGGGAGGC TTGGTACAGC CTGGGGGGTC | 50 |

CDR1

| | | |
|---|---|---|
| 6.1.1H   | CCTGAGACTC TCCTGTCCAG CCTCTGGATT CACCTTTAGC AGCTATGCCA | 100 |
| 4.9.2H   | CCTGAGACTC TCCTGTGCAG CCTCTGGATT CACCTTTAGC AGCTATGCCA | 100 |
| DP47     | CCTGAGACTC TCCTGTGCAG CCTCTGGATT CACCTTTAGC AGCTATGCCA | 100 |
| 2.13.2H  | CCTGAGACTC TCCTGTACAG CCTCTGGATT CACCTTTAGC AGCTATGCCA | 100 |
| Consensus| CCTGAGACTC TCCTGTRCAG CCTCTGGATT CACCTTTAGC AGCTATGCCA | 100 |

CDR1                                                       CDR2

| | | |
|---|---|---|
| 6.1.1H   | TGAGCTGGGT CCGCCAGGCT CCAGGGAAGG GGCTGGAGTG GGTCTCAGCT | 150 |
| 4.9.2H   | TGAGCTGGGT CCGCCAGGCT CCAGGGAAGG GGCTGGAGTG GGTCTCAGCT | 150 |
| DP47     | TGAGCTGGGT CCGCCAGGCT CCAGGGAAGG GGCTGGAGTG GGTCTCAGCT | 150 |
| 2.13.2H  | TGAACTGGGT CCGCCAGGCT CCAGGGAAGG GGCTGGAGTG GGTCTCAGCT | 150 |
| Consensus| TGARCTGGGT CCGCCAGGCT CCAGGGAAGG GGCTGGAGTG GGTCTCAGST | 150 |

CDR2

| | | |
|---|---|---|
| 6.1.1H   | ATTACTGGGA GTGGTGGTAG TACATACTAC GCAGACTCCG TGAAGGGCCG | 200 |
| 4.9.2H   | ATTAGTGGTA GTGGTGGTAT CACATACTAC GCAGACTCCG TGAAGGGCCG | 200 |
| DP47     | ATTAGTGGTA GTGGTGGTAG CACATACTAC GCAGACTCCG TGAAGGGCCG | 200 |
| 2.13.2H  | ATTAGTGGTA GTGGTGGTAC CACATTCTAC GCAGACTCCG TGAAGGGCCG | 200 |
| Consensus| ATTASTGGKA GTGGTGGTAB YACATWCTAC GCAGACTCCG TGAAGGGCCG | 200 |

| | | |
|---|---|---|
| 6.1.1H   | GTTCACCATC TCCAGAGACA ATTCCAAGAA CACGCTGTAT CTGCAAATGA | 250 |
| 4.9.2H   | GTTCACCATC TCCAGAGACA ATTCCAAGAA CACGCTGTAT CTGCAAATGA | 250 |
| DP47     | GTTCACCATC TCCAGAGACA ATTCCAAGAA CACGCTGTAT CTGCAAATGA | 250 |
| 2.13.2H  | GTTCACCATC TCCAGAGACA ATTCCAGGAC CACGCTGTAT CTGCAAATGA | 250 |
| Consensus| GTTCACCATC TCCAGAGACA ATTCCARGAM CACGCTGTAT CTGCAAATGA | 250 |

CDR3

| | | |
|---|---|---|
| 6.1.1H   | ACAGCCTGAG AGCCGAGGAC ACGGCCGTAT ATTACTGTGC GAAAGATC-- | 298 |
| 4.9.2H   | ACAGCCTGAG AGCCGAGGAC ACGGCCGTAT ATTACTGTGC GAAAGATCTG | 300 |
| DP47     | ACAGCCTGAG AGCCGAGGAC ACGGCCGTAT ATTACTGTGC GAAAGA---- | 296 |
| 2.13.2H  | ACAGCCTGAG AGCCGAGGAC ACGGCCGTAT ATTACTGTGC GAAAGATCTT | 300 |
| Consensus| ACAGCCTGAG AGCCGAGGAC ACGGCCGTAT ATTACTGTGC GAAAGATCTK | 300 |

CDR3-for 4.9.2 and 2.13.2

| | | |
|---|---|---|
| 6.1.1H   | ---------- ---------- ---------- ---------- --------C- | 299 |
| 4.9.2H   | GGCTACGGTG ACTTTTACTA CTACTACTAC GGTATGGACG TCTGGGGCCA | 350 |
| DP47     | ---------- ---------- ---------- ---------- ---------- | 296 |
| 2.13.2H  | GGCTGGTCCG ACTCTTACTA CTACTACTAC GGTATGGACG TCTGGGGCCA | 350 |
| Consensus| GGCTRSKSYG ACTYTTACTA CTACTACTAC GGTATGGACG TCTGGGGCCA | 350 |

CDR3-for 6.1.1

| | | |
|---|---|---|
| 6.1.1H   | AGGGACTACG GTGATTATGA GTTGGTTCGA CCCCTGGGGC CAGGGAACCC | 349 |
| 4.9.2H   | AGGGACCAC- ---------- ---------- ---------- ---------- | 359 |
| DP47     | ---------- ---------- ---------- ---------- ---------- | 296 |
| 2.13.2H  | AGGGACCAC- ---------- ---------- ---------- ---------- | 359 |
| Consensus| AGGGACYACG GTGATTATGA GTTGGTTCGA CCCCTGGGGC CAGGGAACCC | 400 |

FIG. 2C-1

```
6.1.1H      TGGTCACCGT CTCCTCAG                                   367
4.9.2H      -GGTCACCGT CTCCTCAG                                   376
DP47        ---------- --------                                   296
2.13.2H     -GGTCACCGT CTCCTCAG                                   376
Consensus   TGGTCACCGT CTCCTCAG                                   418
```

FIG. 2C-2

```
4.17.3H     ---------- ---------- ---CCCAGGA CTGGTGAAGC CTTCGGAGAC  27
DP71        CAGGTGCAGC TGCAGGAGTC GGGCCCAGGA CTGGTGAAGC CTTCGGAGAC  50
Consensus   CAGGTGCAGC TGCAGGAGTC GGGCCCAGGA CTGGTGAAGC CTTCGGAGAC  50
                                            CDR1

4.17.3H     CCTGTCCCTC ACCTGCACTG TCTCTGGTGG CTCCATCAGT AGTTACTACT  77
DP71        CCTGTCCCTC ACCTGCACTG TCTCTGGTGG CTCCATCAGT AGTTACTACT 100
Consensus   CCTGTCCCTC ACCTGCACTG TCTCTGGTGG CTCCATCAGT AGTTACTACT 100
            CDR1

4.17.3H     GGAGTTGGAT CCGGCAGCCC CCAGGGAAGG GACTGGAGTG GATTGGGTAT 127
DP71        GGAGCTGGAT CCGGCAGCCC CCAGGGAAGG GACTGGAGTG GATTGGGTAT 150
Consensus   GGAGYTGGAT CCGGCAGCCC CCAGGGAAGG GACTGGAGTG GATTGGGTAT 150
                 CDR2

4.17.3H     ATCTATTACA GTGGGAGCAC CAACTACAAC CCCTCCCTCA AGAGTCGAGT 177
DP71        ATCTATTACA GTGGGAGCAC CAACTACAAC CCCTCCCTCA AGAGTCGAGT 200
Consensus   ATCTATTACA GTGGGAGCAC CAACTACAAC CCCTCCCTCA AGAGTCGAGT 200

4.17.3H     CACCATATCA GTAGACACGT CCAAGAACCA GTTCTCCCTG AAGCTGACTT 227
DP71        CACCATATCA GTAGACACGT CCAAGAACCA GTTCTCCCTG AAGCTGAGCT 250
Consensus   CACCATATCA GTAGACACGT CCAAGAACCA GTTCTCCCTG AAGCTGAGYT 250
                                                       CDR3

4.17.3H     CTGTGACCGC TGCGGACACG GCCGTGTATT ACTGTGCCAG GACGTATAGC 277
DP71        CTGTGACCGC TGCGGACACG GCCGTGTATT ACTGTGC--- GA--------  289
Consensus   CTGTGACCGC TGCGGACACG GCCGTGTATT ACTGTGCCAG GACGTATAGC 300

4.17.3H     AGTTCGTTCT ACTACTACGG TATGGACGTC TGGGGCCAAG GGACCACGGT 327
DP71        ---------- ---------- ---GA----- ---------- -GA-------  293
Consensus   AGTTCGTTCT ACTACTACGG TATGGACGTC TGGGGCCAAG GGACCACGGT 350

4.17.3H     CACCGTCTCC TCAG                                         341
DP71        ---------- ----                                         293
Consensus   CACCGTCTCC TCAG                                         364
```

FIG. 2D

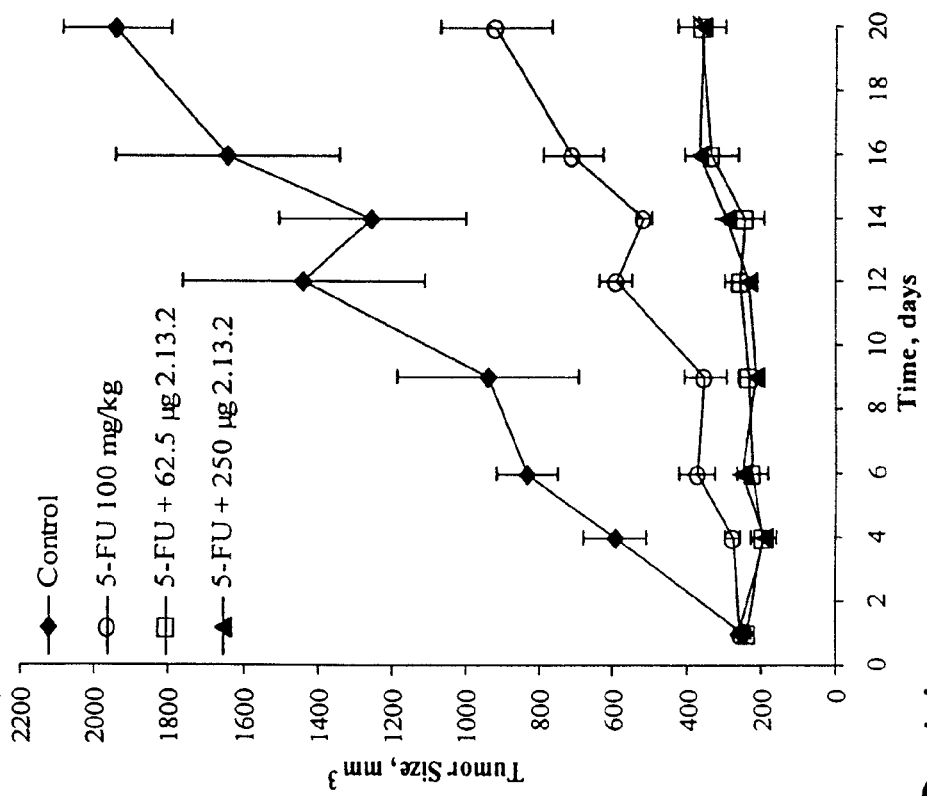
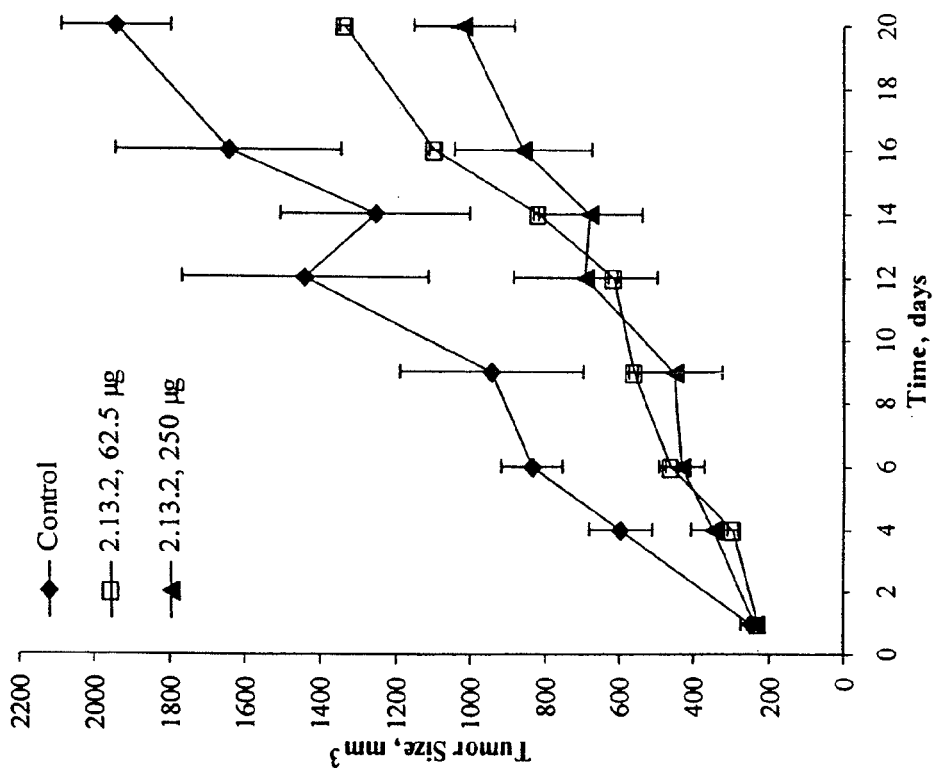
FIG. 11

| Clone | C domain mutations | FR mutation | CDR mutation | Change in Cys | Change in glycosylation |
|---|---|---|---|---|---|
| 2.13.2 Heavy | 0 | 3 | 8 | 0 | 0 |
| 2.13.2 Light | 0 | 1 | 4 | 1 (CDR3) | 0 |
| 2.12.2 Heavy | 0 | 2 | 8 | 0 | 0 |
| 2.12.2 Light | 0 | 3 | 5 | 0 | 0 |

FIG. 19A

```
PF2 2.13.2 Heavy chain (DP-47(3-23)/D6-19/JH6)
                                                                                                                      +                                                                                               ++
MEFGLSWLFL VAILKGVQCE VQLLESGGGL VQPGGSLRLS CTASGFTFSS YAMNWVRQAP GKGLEWVSAI SGSGGTTFYA DSVKGRFTIS RDNSRTTLYL
MEFGLSWLFL VAILKGVQCE VQLLESGGGL VQPGGSLRLS CAASGFTFSS YAMSWVRQAP GKGLEWVSAI SGSGGSTYYA DSVKGRFTIS RDNSKNTLYL
                                                    *   *                *                *  **
QMNSLRAEDT AVYYCAK--D LGWSDSYYYY YGMDVWGQGT TVTVSSASTK GPSVFPLAPC SRSTSESTAA LGCLVKDYFP EPVTVSWNSG ALTSGVHTFP
QMNSLRAEDT AVYYCAKGYS SGW--YYYYY YGMDVWGQGT TVTVSSASTK GPSVFPLAPC SRSTSESTAA LGCLVKDYFP EPVTVSWNSG ALTSGVHTFP
           * *  ***

AVLQSSGLYS LSSVVTVPSS NFGTQTYTCN VDHKPSNTKV DKTVERKCCV ECPPCPAPPV AGPSVFLFPP KPKDTLMISR TPEVTCVVVD VSHEDPEVQF
AVLQSSGLYS LSSVVTVPSS NFGIQTYTCN VDHKPSNTKV DKTVERKCCV ECPPCPAPPV AGPSVFLFPP KPKDTLMISR TPEVTCVVVD VSHEDPEVQF

NWYVDGVEVH NAKTKPREEQ FNSTFRVVSV LTVVHQDWLN GKEYKCKVSN KGLPAPIEKT ISKTKGQPRE PQVYTLPPSR EEMTKNQVSL TCLVKGFYPS
NWYVDGVEVH NAKTKPREEQ FNSTFRVVSV LTVVHQDWLN GKEYKCKVSN KGLPAPIEKT ISKTKGQPRE PQVYTLPPSR EEMTKNQVSL TCLVKGFYPS

DIAVEWESNG QPENNYKTTP PMLDSDGSFF LYSKLTVDKS RWQQGNVFSC SVMHEALHNH YTQKSLSLSP GK
DIAVEWESNG QPENNYKTTP PMLDSDGSFF LYSKLTVDKS RWQQGNVFSC SVMHEALHNH YTQKSLSLSP GK
```

```
MDMRVPAQLL GLLLLWFPGA RCDIQMTQFP SSLSASVGDR VTIITCRASQG IRNDLGWYQQ KPGKAPKRLI YAASRLHRGV PSRFSGSGSG TEFTLTISSL
MDMRVPAQLL GLLLLWFPGA RCDIQMTQSP SSLSASVGDR VTIITCRASQG IRNDLGWYQQ KPGKAPKRLI YAASSLQSGV PSRFSGSGSG TEFTLTISSL

QPEDFATYYC LQHNSYPCSF GQGTKLEIKR TVAAPSVFIF PPSDEQLKSG TASVVCLLNN FYPREAKVQW KVDNALQSGN SQESVTEQDS KDSTYSLSST
QPEDFATYYC LQHNSYPYTF GQGTKLEIKR TVAAPSVFIF PPSDEQLKSG TASVVCLLNN FYPREAKVQW KVDNALQSGN SQESVTEQDS KDSTYSLSST

LTLSKADYEK HKVYACEVTH QGLSSPVTKS FNRGEC
LTLSKADYEK HKVYACEVTH QGLSSPVTKS FNRGEC
```

FIG. 19C

PF2 2.12.1 Heavy chain (DP-35(3-11)/D3-3/JH6)

```
MEFGLSWVFL VAIIKGVQCQ AQLVESGGGL VKPGGSLRLS CAASGFTFSD YYMSWIRQAP GKGLEWVSYI SSSGSTRDYA DSVKGRFTIS RDNAKNSLYL
MEFGLSWVFL VAIIKGVQCQ VQLVESGGGL VKPGGSLRLS CAASGFTFSD YYMSWIRQAP GKGLEWVSYI SSSGSTIYYA DSVKGRFTIS RDNAKNSLYL

QMNSLRAEDT AVYYCVR--D GVETTF-YYY YYGMDVWGQG TTVTVSSAST KGPSVFPLAP CSRSTSESTA ALGCLVKDYF PEPVTVSWNS GALTSGVHTF
QMNSLRAEDT AVYYCARVLR FLEWLLYYYY YYGMDVWGQG TTVTVSSAST KGPSVFPLAP CSRSTSESTA ALGCLVKDYF PEPVTVSWNS GALTSGVHTF

PAVLQSSGLY SLSSVVTVPS SNFGTQTYTC NVDHKPSNTK VDKTVERKCC VECPPCPAPP VAGPSVFLFP PKPKDTLMIS RTPEVTCVVV DVSHEDPEVQ
PAVLQSSGLY SLSSVVTVPS SNFGTQTYTC NVDHKPSNTK VDKTVERKCC VECPPCPAPP VAGPSVFLFP PKPKDTLMIS RTPEVTCVVV DVSHEDPEVQ

FNWYVDGVEV HNAKTKPREE QFNSTFRVVS VLTVVHQDWL NGKEYKCKVS NKGLPAPIEK TISKTKGQPRE PQVYTLPPS REEMTKNQVS LTCLVKGFYP
FNWYVDGVEV HNAKTKPREE QFNSTFRVVS VLTVVHQDWL NGKEYKCKVS NKGLPAPIEK TISKTKGQPRE PQVYTLPPS REEMTKNQVS LTCLVKGFYP

SDIAVEWESN GQPENNYKTT PPMLDSDGSF FLYSKLTVDK SRWQQGNVFS CSVMHEALHN HYTQKSLSLSP GK
SDIAVEWESN GQPENNYKTT PPMLDSDGSF FLYSKLTVDK SRWQQGNVFS CSVMHEALHN HYTQKSLSLSP GK
```

FIG. 19D

PF2.12.1 Light chain (A30/Jk1)

```
MDMRVPAQLL GLLLLWFPGA RCDIQMTQSP SSLSASVGDR VTFTCRASQD IRRDLGWYQQ KPGKAPKRLI YAASRLQSGV PSRFSGSGSG TEFTLTISSL
MDMRVPAQLL GLLLLWFPGA RCDIQMTQSP SSLSASVGDR VTITCRASQG IRNDLGWYQQ KPGKAPKRLI YAASSLQSGV PSRFSGSGSG TEFTLTISSL
           *         *                 +     *  *

QPEDFATYYC LQHNNYPRTF GQGTEVEIIR TVAAPSVFIF PPSDEQLKSG TASVVCLLNN FYPREAKVQW KVDNALQSGN SQESVTEQDS KDSTYSLSST
QPEDFATYYC LQHNSYPWTF GQGTKVEIKR TVAAPSVFIF PPSDEQLKSG TASVVCLLNN FYPREAKVQW KVDNALQSGN SQESVTEQDS KDSTYSLSST
        +  *   *  *      *   *

LTLSKADYEK HKVYACEVTH QGLSSPVTKS FNRGEC
LTLSKADYEK HKVYACEVTH QGLSSPVTKS FNRGEC
```

FIG. 19E

```
                          SEQUENCE LISTING

<160> NUMBER OF SEQ ID NOS: 60

<210> SEQ ID NO 1
<211> LENGTH: 291
<212> TYPE: DNA
<213> ORGANISM: Homo sapiens

<400> SEQUENCE: 1
tgcatctgta ggagacagag tcaccttcac ttgccgggca agtcaggaca ttagacgtga      60
tttaggctgg tatcagcaga aaccagggaa agctcctaag cgcctgatct atgctgcatc     120
ccgtttacaa agtggggtcc catcaaggtt cagcggcagt ggatctggga cagaattcac     180
tctcacaatc agcagcctgc agcctgaaga ttttgcaact tattactgtc tacagcataa     240
taattatcct cggacgttcg gccaagggac cgaggtggaa atcatacgaa c              291

<210> SEQ ID NO 2
<211> LENGTH: 136
<212> TYPE: PRT
<213> ORGANISM: Homo sapiens

<400> SEQUENCE: 2

Ala Ser Val Gly Asp Arg Val Thr Phe Thr Cys Arg Ala Ser Gln Asp
  1               5                  10                  15

Ile Arg Arg Asp Leu Gly Trp Tyr Gln Gln Lys Pro Gly Lys Ala Pro
             20                  25                  30

Lys Arg Leu Ile Tyr Ala Ala Ser Arg Leu Gln Ser Gly Val Pro Ser
         35                  40                  45

Arg Phe Ser Gly Ser Gly Ser Gly Thr Glu Phe Thr Leu Thr Ile Ser
     50                  55                  60

Ser Leu Gln Pro Glu Asp Phe Ala Thr Tyr Tyr Cys Leu Gln His Asn
 65                  70                  75                  80
```

```
Asn Tyr Pro Arg Thr Phe Gly Gln Gly Thr Glu Val Glu Ile Ile Arg
                85                  90                  95

Thr Val Ala Ala Pro Ser Val Phe Ile Phe Pro Pro Ser Asp Glu Gln
            100                 105                 110

Leu Lys Ser Gly Thr Ala Ser Val Val Cys Leu Leu Asn Asn Phe Tyr
        115                 120                 125

Pro Arg Glu Ala Lys Val Gln Trp
    130                 135

<210> SEQ ID NO 3
<211> LENGTH: 352
<212> TYPE: DNA
<213> ORGANISM: Homo sapiens

<400> SEQUENCE: 3
gggaggcttg gtcaagcctg gaggtccctg agactctcct gtgcagcctc tggattcact     60
ttcagtgact actatatgag ctggatccgc caggctccag ggaaggggct ggaatgggtt    120
tcatacatta gtagtagtgg tagtaccaga gactacgcag actctgtgaa gggccgattc    180
accatctcca gggacaacgc caagaactca ctgtatctgc aaatgaacag cctgagagcc    240
gaggacacgg ccgtgtatta ctgtgtgaga gatggagtgg aaactacttt ttactactac    300
tactacggta tggacgtctg gggccaaggg accacggtca ccgtctcctc ag            352

<210> SEQ ID NO 4
<211> LENGTH: 174
<212> TYPE: PRT
<213> ORGANISM: Homo sapiens

<400> SEQUENCE: 4

Gly Arg Leu Gly Gln Ala Trp Arg Ser Leu Arg Leu Ser Cys Ala Ala
  1               5                  10                  15

Ser Gly Phe Thr Phe Ser Asp Tyr Tyr Met Ser Trp Ile Arg Gln Ala
             20                  25                  30

Pro Gly Lys Gly Leu Glu Trp Val Ser Tyr Ile Ser Ser Ser Gly Ser
         35                  40                  45

Thr Arg Asp Tyr Ala Asp Ser Val Lys Gly Arg Phe Thr Ile Ser Arg
     50                  55                  60

Asp Asn Ala Lys Asn Ser Leu Tyr Leu Gln Met Asn Ser Leu Arg Ala
 65                  70                  75                  80

Glu Asp Thr Ala Val Tyr Tyr Cys Val Arg Asp Gly Val Glu Thr Thr
                 85                  90                  95

Phe Tyr Tyr Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ser Cys Ala
                165                 170

<210> SEQ ID NO 5
<211> LENGTH: 322
<212> TYPE: DNA
<213> ORGANISM: Homo sapiens
```

<400> SEQUENCE: 5

```
gacatccaga tgacccagtt tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatcccgtt tgcacagagg ggtcccatca   180
aggttcagcg gcagtggatc tgggacagaa ttcactctca caatcagcag cctgcagcct   240
gaagattttg caacttatta ctgtttacaa cataatagtt acccgtgcag ttttggccag   300
gggaccaagc tggagatcaa ac                                            322
```

<210> SEQ ID NO 6
<211> LENGTH: 107
<212> TYPE: PRT
<213> ORGANISM: Homo sapiens

<400> SEQUENCE: 6

```
Asp Ile Gln Met Thr Gln Phe Pro Ser Ser Leu Ser Ala Ser Val Gly
 1               5                  10                  15
Asp Arg Val Thr Ile Thr Cys Arg Ala Ser Gln Gly Ile Arg Asn Asp
                20                  25                  30
Leu Gly Trp Tyr Gln Gln Lys Pro Gly Lys Ala Pro Lys Arg Leu Ile
            35                  40                  45
Tyr Ala Ala Ser Arg Leu His Arg Gly Val Pro Ser Arg Phe Ser Gly
        50                  55                  60
Ser Gly Ser Gly Thr Glu Phe Thr Leu Thr Ile Ser Ser Leu Gln Pro
    65                  70                  75                  80
Glu Asp Phe Ala Thr Tyr Tyr Cys Leu Gln His Asn Ser Tyr Pro Cys
                85                  90                  95
Ser Phe Gly Gln Gly Thr Lys Leu Glu Ile Lys
            100                 105
```

<210> SEQ ID NO 7
<211> LENGTH: 375
<212> TYPE: DNA
<213> ORGANISM: Homo sapiens

<400> SEQUENCE: 7

```
aggtgcagct gttggagtct ggggggaggct tggtacagcc tggggggtcc ctgagactct    60
cctgtacagc ctctggattc acctttagca gctatgccat gaactgggtc cgccaggctc   120
cagggaaggg gctggagtgg gtctcagcta ttagtggtag tggtggtacc acattctacg   180
cagactccgt gaagggccgg ttcaccatct ccagagacaa ttccaggacc acgctgtatc   240
tgcaaatgaa cagcctgaga gccgaggaca cggccgtata ttactgtgcg aaagatcttg   300
gctggtccga ctcttactac tactactacg gtatggacgt ctggggccaa gggaccacgg   360
tcaccgtctc ctcag                                                    375
```

<210> SEQ ID NO 8
<211> LENGTH: 124
<212> TYPE: PRT
<213> ORGANISM: Homo sapiens

<400> SEQUENCE: 8

```
Val Gln Leu Leu Glu Ser Gly Gly Gly Leu Val Gln Pro Gly Gly Ser
 1               5                  10                  15
Leu Arg Leu Ser Cys Thr Ala Ser Gly Phe Thr Phe Ser Ser Tyr Ala
                20                  25                  30
```

```
Met Asn Trp Val Arg Gln Ala Pro Gly Lys Gly Leu Glu Trp Val Ser
         35                  40                  45
Ala Ile Ser Gly Ser Gly Gly Thr Thr Phe Tyr Ala Asp Ser Val Lys
 50                  55                  60
Gly Arg Phe Thr Ile Ser Arg Asp Asn Ser Arg Thr Thr Leu Tyr Leu
 65                  70                  75                  80
Gln Met Asn Ser Leu Arg Ala Glu Asp Thr Ala Val Tyr Tyr Cys Ala
             85                  90                  95
Lys Asp Leu Gly Trp Ser Asp Ser Tyr Tyr Tyr Tyr Gly Met Asp
                100                 105                 110
Val Trp Gly Gln Gly Thr Thr Val Thr Val Ser Ser
        115                 120

<210> SEQ ID NO 9
<211> LENGTH: 302
<212> TYPE: DNA
<213> ORGANISM: Homo sapiens

<400> SEQUENCE: 9
tcctccctgt ctgcatctgt aggagacaga gtcaccttca cttgccgggc aagtcaggac      60
attagacgtg atttaggctg gtatcagcag aaaccaggga agctcctaa gcgcctgatc     120
tatgctgcat cccgtttaca aagtggggtc ccatcaaggt tcagcggcag tggatctggg     180
acagaattca ctctcacaat cagcagcctg agcctgaag attttgcaac ttattactgt     240
ctacagcata taattatcc tcggacgttc ggccaaggga ccgaggtgga atcatacga      300
ac                                                                   302

<210> SEQ ID NO 10
<211> LENGTH: 100
<212> TYPE: PRT
<213> ORGANISM: Homo sapiens

<400> SEQUENCE: 10

Ser Ser Leu Ser Ala Ser Val Gly Asp Arg Val Thr Phe Thr Cys Arg
 1               5                  10                  15
Ala Ser Gln Asp Ile Arg Arg Asp Leu Gly Trp Tyr Gln Gln Lys Pro
             20                  25                  30
Gly Lys Ala Pro Lys Arg Leu Ile Tyr Ala Ala Ser Arg Leu Gln Ser
         35                  40                  45
Gly Val Pro Ser Arg Phe Ser Gly Ser Gly Ser Gly Thr Glu Phe Thr
 50                  55                  60
Leu Thr Ile Ser Ser Leu Gln Pro Glu Asp Phe Ala Thr Tyr Tyr Cys
 65                  70                  75                  80
Leu Gln His Asn Asn Tyr Pro Arg Thr Phe Gly Gln Gly Thr Glu Val
             85                  90                  95
Glu Ile Ile Arg
        100

<210> SEQ ID NO 11
<211> LENGTH: 338
<212> TYPE: DNA
<213> ORGANISM: Homo sapiens

<400> SEQUENCE: 11
gggcccagga ctggtgaagc cttcggagac cctgtccctc acctgcactg tctctggtgg     60
ctccatcagt aattactact ggagctggat ccggcagccc gccgggaagg gactggagtg    120
```

```
gattgggcgt atctatacca gtgggagccc caactacaac ccctccctca agagtcgagt    180
caccatgtca gtagacacgt ccaagaacca gttctccctg aagctgaact ctgtgaccgc    240
cgcggacacg gccgtgtatt actgtgcggt aacgattttt ggagtggtta ttatctttga    300
ctactggggc cagggaaccc tggtcaccgt ctcctcag                            338
```

<210> SEQ ID NO 12
<211> LENGTH: 112
<212> TYPE: PRT
<213> ORGANISM: Homo sapiens

<400> SEQUENCE: 12

Gly Pro Gly Leu Val Lys Pro Ser Glu Thr Leu Ser Leu Thr Cys Thr
 1               5                  10                  15

Val Ser Gly Gly Ser Ile Ser Asn Tyr Tyr Trp Ser Trp Ile Arg Gln
                20                  25                  30

Pro Ala Gly Lys Gly Leu Glu Trp Ile Gly Arg Ile Tyr Thr Ser Gly
            35                  40                  45

Ser Pro Asn Tyr Asn Pro Ser Leu Lys Ser Arg Val Thr Met Ser Val
        50                  55                  60

Asp Thr Ser Lys Asn Gln Phe Ser Leu Lys Leu Asn Ser Val Thr Ala
65                  70                  75                  80

Ala Asp Thr Ala Val Tyr Tyr Cys Ala Val Thr Ile Phe Gly Val Val
                85                  90                  95

Ile Ile Phe Asp Tyr Trp Gly Gln Gly Thr Leu Val Thr Val Ser Ser
            100                 105                 110

<210> SEQ ID NO 13
<211> LENGTH: 322
<212> TYPE: DNA
<213> ORGANISM: Homo sapiens

<400> SEQUENCE: 13

```
gacatccaga tgacccagtc tccatcctcc ctgtctgcat ctgtaggaga cagagtcacc     60
atcacttgcc gggcaagtca gggcattaga agtgatttag ctggtttca gcagaaacca    120 gggaaagccc ctaagcgcct gatctatgct gcatccaaat tacaccgtgg ggtcccatca    180
aggttcagcg gcagtggatc tgggacagaa ttcactctca caatcagccg cctgcagcct    240
gaagattttg caacttatta ctgtctacag cataatagtt accctctcac tttcggcgga    300
gggaccaagg tggagatcaa ac                                             322
```

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Asp
                20                  25                  30

Leu Gly Trp Phe Gln Gln Lys Pro Gly Lys Ala Pro Lys Arg Leu Ile
            35                  40                  45

Tyr Ala Ala Ser Lys Leu His Arg Gly Val Pro Ser Arg Phe Ser Gly
        50                  55                  60

Ser Gly Ser Gly Thr Glu Phe Thr Leu Thr Ile Ser Arg Leu Gln Pro
65                  70                  75                  80

```
Glu Asp Phe Ala Thr Tyr Tyr Cys Leu Gln His Asn Ser Tyr Pro Leu
                85                  90                  95
Thr Phe Gly Gly Gly Thr Lys Val Glu Ile Lys
            100                 105
```

<210> SEQ ID NO 15
<211> LENGTH: 376
<212> TYPE: DNA
<213> ORGANISM: Homo sapiens

<400> SEQUENCE: 15

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtat cacatactac    180
gcagactccg tgaagggccg gttcaccatc tccagagaca attccaagaa cacgctgtat    240
ctgcaaatga acagcctgag agccgaggac acggccgtat attactgtgc gaaagatctg    300
ggctacggtg acttttacta ctactactac ggtatggacg tctggggcca agggaccacg    360
gtcaccgtct cctcag                                                    376
```

<210> SEQ ID NO 16
<211> LENGTH: 125
<212> TYPE: PRT
<213> ORGANISM: Homo sapiens

<400> SEQUENCE: 16

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ile Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Leu Gly Tyr Gly Asp Phe Tyr Tyr Tyr Tyr Tyr Gly Met
            100                 105                 110
Asp Val Trp Gly Gln Gly Thr Thr Val Thr Val Ser Ser
        115                 120                 125
```

<210> SEQ ID NO 17
<211> LENGTH: 279
<212> TYPE: DNA
<213> ORGANISM: Homo sapiens

<400> SEQUENCE: 17

```
caggagacag agtcaccatc acttgccggg caagtcagag cattagtacc tttttaaatt      60
ggtatcagca gaaaccaggg aaagccccta aactcctgat ccatgttgca tccagtttac    120
aaggtggggt cccatcaagg ttcagtggca gtggatctgg gacagatttc actctcacca    180
tcagcagtct gcaacctgaa gattttgcaa cttactactg tcaacagagt tacaatgccc    240
cactcacttt cggcggaggg accaaggtgg agatcaaac                          279
```

<210> SEQ ID NO 18
<211> LENGTH: 92
<212> TYPE: PRT
<213> ORGANISM: Homo sapiens

<400> SEQUENCE: 18

Gly Asp Arg Val Thr Ile Thr Cys Arg Ala Ser Gln Ser Ile Ser Thr
1               5                   10                  15

Phe Leu Asn Trp Tyr Gln Gln Lys Pro Gly Lys Ala Pro Lys Leu Leu
            20                  25                  30

Ile His Val Ala Ser Ser Leu Gln Gly Gly Val Pro Ser Arg Phe Ser
        35                  40                  45

Gly Ser Gly Ser Gly Thr Asp Phe Thr Leu Thr Ile Ser Ser Leu Gln
    50                  55                  60

Pro Glu Asp Phe Ala Thr Tyr Tyr Cys Gln Gln Ser Tyr Asn Ala Pro
65                  70                  75                  80

Leu Thr Phe Gly Gly Gly Thr Lys Val Glu Ile Lys
            85                  90

<210> SEQ ID NO 19
<211> LENGTH: 341
<212> TYPE: DNA
<213> ORGANISM: Homo sapiens

<400> SEQUENCE: 19
cccaggactg gtgaagcctt cggagaccct gtccctcacc tgcactgtct ctggtggctc     60
catcagtagt tactactgga gttggatccg gcagccccca gggaagggac tggagtggat    120
tgggtatatc tattacagtg ggagcaccaa ctacaacccc tccctcaaga gtcgagtcac    180
catatcagta gacacgtcca agaaccagtt ctccctgaag ctgagttctg tgaccgctgc    240
ggacacggcc gtgtattact gtgccaggac gtatagcagt tcgttctact actacggtat    300
ggacgtctgg ggccaaggga ccacggtcac cgtctcctca g                        341

<210> SEQ ID NO 20
<211> LENGTH: 113
<212> TYPE: PRT
<213> ORGANISM: Homo sapiens

<400> SEQUENCE: 20

Pro Gly Leu Val Lys Pro Ser Glu Thr Leu Ser Leu Thr Cys Thr Val
1               5                   10                  15

Ser Gly Gly Ser Ile Ser Ser Tyr Tyr Trp Ser Trp Ile Arg Gln Pro
            20                  25                  30

Pro Gly Lys Gly Leu Glu Trp Ile Gly Tyr Ile Tyr Tyr Ser Gly Ser
        35                  40                  45

Thr Asn Tyr Asn Pro Ser Leu Lys Ser Arg Val Thr Ile Ser Val Asp
    50                  55                  60

Thr Ser Lys Asn Gln Phe Ser Leu Lys Leu Ser Ser Val Thr Ala Ala
65                  70                  75                  80

Asp Thr Ala Val Tyr Tyr Cys Ala Arg Thr Tyr Ser Ser Ser Phe Tyr
            85                  90                  95

Tyr Tyr Gly Met Asp Val Trp Gly Gln Gly Thr Thr Val Thr Val Ser
            100                 105                 110

Ser

```
<210> SEQ ID NO 21
<211> LENGTH: 274
<212> TYPE: DNA
<213> ORGANISM: Homo sapiens
<220> FEATURE:
<221> NAME/KEY: modified_base
<222> LOCATION: (240)
<223> OTHER INFORMATION: a, c, t, g, other or unknown

<400> SEQUENCE: 21
agagccaccc tctcctgtag ggccagtcag agtgttcgcg gcaggtactt agcctggtac     60
cagcagaaac ctggccaggc tcccaggctc ctcatctatg gtgcatccag cagggccact    120
ggcatcccag acaggttcag tggcagtggg tctgggacag acttcactct caccatcagc    180
agactggagc ctgaagattt tgcagtgttt tactgtcagc agtatggtag ttcacctcgn    240
acgttcggcc aagggaccaa ggtggaaatc aaac                                274

<210> SEQ ID NO 22
<211> LENGTH: 91
<212> TYPE: PRT
<213> ORGANISM: Homo sapiens

<400> SEQUENCE: 22

Arg Ala Thr Leu Ser Cys Arg Ala Ser Gln Ser Val Arg Gly Arg Tyr
 1               5                  10                  15

Leu Ala Trp Tyr Gln Gln Lys Pro Gly Gln Ala Pro Arg Leu Leu Ile
                20                  25                  30

Tyr Gly Ala Ser Ser Arg Ala Thr Gly Ile Pro Asp Arg Phe Ser Gly
            35                  40                  45

Ser Gly Ser Gly Thr Asp Phe Thr Leu Thr Ile Ser Arg Leu Glu Pro
        50                  55                  60

Glu Asp Phe Ala Val Phe Tyr Cys Gln Gln Tyr Gly Ser Ser Pro Arg
 65                  70                  75                  80

Thr Phe Gly Gln Gly Thr Lys Val Glu Ile Lys
                85                  90

<210> SEQ ID NO 23
<211> LENGTH: 367
<212> TYPE: DNA
<213> ORGANISM: Homo sapiens

<400> SEQUENCE: 23
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg gtctcaggt attactggga gtggtggtag tacatactac    180
gcagactccg tgaagggccg gttcaccatc tccagagaca attccaagaa cacgctgtat    240
ctgcaaatga acagcctgag agccgaggac acggccgtat attactgtgc gaaagatcca    300
gggactacgg tgattatgag ttggttcgac ccctggggcc agggaaccct ggtcaccgtc    360
tcctcag                                                              367

<210> SEQ ID NO 24
<211> LENGTH: 122
<212> TYPE: PRT
<213> ORGANISM: Homo sapiens
```

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser
            115                 120

<210> SEQ ID NO 25
<211> LENGTH: 320
<212> TYPE: DNA
<213> ORGANISM: Homo sapiens

<400> SEQUENCE: 25

```
gaactgtggc tgcaccatct gtcttcatct tcccgccatc tgatgagcag ttgaaatctg    60
gaactgcctc tgttgtgtgc ctgctgaata acttctatcc cagagaggcc aaagtacagt   120
ggaaggtgga taacgccctc caatcgggta actcccagga gagtgtcaca gagcaggaca   180
gcaaggacag cacctacagc ctcagcagca ccctgacgct gagcaaagca gactacgaga   240
aacacaaagt ctacgcctgc gaagtcaccc atcagggcct gagctcgccc gtcacaaaga   300
gcttcaacag gggagagtgt                                               320
```

<210> SEQ ID NO 26
<211> LENGTH: 106
<212> TYPE: PRT
<213> ORGANISM: Homo sapiens

<400> SEQUENCE: 26

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 27
<211> LENGTH: 978
<212> TYPE: DNA
<213> ORGANISM: Homo sapiens

<400> SEQUENCE: 27

```
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccctga ggtcacgtgc      420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct cctctacag caagctcacc gtggacaaga gcaggtggca gcagggaac      900
gtcttctcat gctccgtgat gcatgaggct ctgcacaacc actacacgca gaagagcctc     960
tccctgtctc cgggtaaa                                                   978
```

<210> SEQ ID NO 28
<211> LENGTH: 326
<212> TYPE: PRT
<213> ORGANISM: Homo sapiens

<400> SEQUENCE: 28

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

```
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 29
<211> LENGTH: 296
<212> TYPE: DNA
<213> ORGANISM: Homo sapiens

<400> SEQUENCE: 29
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagggaca acgccaagaa ctcactgtat     240
ctgcaaatga acagcctgag agccgaggac acggccgtgt attactgtgc gagaga         296

<210> SEQ ID NO 30
<211> LENGTH: 98
<212> TYPE: PRT
<213> ORGANISM: Homo sapiens

<400> SEQUENCE: 30

Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Tyr Met Ser Trp Ile Arg Gln Ala Pro Gly Lys Gly Leu Glu Trp Val
        35                  40                  45
Ser Tyr Ile Ser Ser Ser Gly Ser Thr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg
```

<210> SEQ ID NO 31
<211> LENGTH: 296
<212> TYPE: DNA
<213> ORGANISM: Homo sapiens

<400> SEQUENCE: 31

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaga         296
```

<210> SEQ ID NO 32
<211> LENGTH: 98
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 33
<211> LENGTH: 296
<212> TYPE: DNA
<213> ORGANISM: Homo sapiens

<400> SEQUENCE: 33

```
caggtgcagc tgcaggagtc gggcccagga ctggtgaagc cttcggggac cctgtccctc      60
acctgcgctg tctctggtgg ctccatcagc agtagtaact ggtggagttg ggtccgccag     120
cccccaggga aggggctgga gtggattggg gaaatctatc atagtgggag caccaactac     180
aacccgtccc tcaagagtcg agtcaccata tcagtagaca agtccaagaa ccagttctcc     240
ctgaagctga gctctgtgac cgccgcggac acggccgtgt attactgtgc gagaga         296
```

<210> SEQ ID NO 34
<211> LENGTH: 98
<212> TYPE: PRT
<213> ORGANISM: Homo sapiens

<400> SEQUENCE: 34

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

```
Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg

<210> SEQ ID NO 35
<211> LENGTH: 293
<212> TYPE: DNA
<213> ORGANISM: Homo sapiens

<400> SEQUENCE: 35
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggtat atctattaca gtgggagcac caactacaac    180
ccctccctca agagtcgagt caccatatca gtagacacgt ccaagaacca gttctccctg    240
aagctgagct ctgtgaccgc tgcggacacg gccgtgtatt actgtgcgag aga           293

<210> SEQ ID NO 36
<211> LENGTH: 97
<212> TYPE: PRT
<213> ORGANISM: Homo sapiens

<400> SEQUENCE: 36

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg

<210> SEQ ID NO 37
<211> LENGTH: 290
<212> TYPE: DNA
<213> ORGANISM: Homo sapiens

<400> SEQUENCE: 37
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctcc                290
```

<210> SEQ ID NO 38
<211> LENGTH: 96
<212> TYPE: PRT
<213> ORGANISM: Homo sapiens

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 39
<211> LENGTH: 288
<212> TYPE: DNA
<213> ORGANISM: Homo sapiens
<220> FEATURE:
<221> NAME/KEY: modified_base
<222> LOCATION: (288)
<223> OTHER INFORMATION: a, c, t, g, other or unknown

<400> SEQUENCE: 39
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt accctccn                 288

<210> SEQ ID NO 40
<211> LENGTH: 96
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

<210> SEQ ID NO 41
<211> LENGTH: 288
<212> TYPE: DNA
<213> ORGANISM: Homo sapiens

<400> SEQUENCE: 41

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcch                288
```

<210> SEQ ID NO 42
<211> LENGTH: 96
<212> TYPE: PRT
<213> ORGANISM: Homo sapiens

<400> SEQUENCE: 42

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

<210> SEQ ID NO 43
<211> LENGTH: 293
<212> TYPE: DNA
<213> ORGANISM: Homo sapiens

<400> SEQUENCE: 43

```
caggtgcagc tgcaggagtc gggcccagga ctggtgaagc cttcggagac cctgtccctc    60
acctgcactg tctctggtgg ctccatcagt agttactact ggagctggat ccggcagccc   120
gccgggaagg gactggagtg gattgggcgt atctatacca gtgggagcac caactacaac   180
ccctccctca gagtcgagt caccatgtca gtagacacgt ccaagaacca gttctccctg   240
aagctgagct ctgtgaccgc cgcggacacg gccgtgtatt actgtgcgag aga           293
```

<210> SEQ ID NO 44
<211> LENGTH: 97
<212> TYPE: PRT
<213> ORGANISM: Homo sapiens

<400> SEQUENCE: 44

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
     50                  55                  60

Ser Arg Val Thr Met Ser Val Asp Thr Ser Lys Asn Gln Phe Ser Leu
 65                  70                  75                  80

```
Lys Leu Ser Ser Val Thr Ala Ala Asp Thr Ala Val Tyr Tyr Cys Ala
                85                  90                  95

Arg

<210> SEQ ID NO 45
<211> LENGTH: 470
<212> TYPE: PRT
<213> ORGANISM: Homo sapiens

<400> SEQUENCE: 45

Met Glu Phe Gly Leu Ser Trp Leu Phe Leu Val Ala Ile Leu Lys Gly
 1               5                  10                  15

Val Gln Cys Glu Val Gln Leu Leu Glu Ser Gly Gly Gly Leu Val Gln
                20                  25                  30

Pro Gly Gly Ser Leu Arg Leu Ser Cys Thr Ala Ser Gly Phe Thr Phe
            35                  40                  45

Ser Ser Tyr Ala Met Asn Trp Val Arg Gln Ala Pro Gly Lys Gly Leu
        50                  55                  60

Glu Trp Val Ser Ala Ile Ser Gly Ser Gly Gly Thr Thr Phe Tyr Ala
 65                  70                  75                  80

Asp Ser Val Lys Gly Arg Phe Thr Ile Ser Arg Asp Asn Ser Arg Thr
                85                  90                  95

Thr Leu Tyr Leu Gln Met Asn Ser Leu Arg Ala Glu Asp Thr Ala Val
                100                 105                 110

Tyr Tyr Cys Ala Lys Asp Leu Gly Trp Ser Asp Ser Tyr Tyr Tyr Tyr
            115                 120                 125

Tyr Gly Met Asp Val Trp Gly Gln Gly Thr Thr Val Thr Val Ser Ser
        130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350
```

```
Ala Pro Ile Glu Lys Thr Ile Ser Lys Thr Lys Gly Gln Pro Arg Glu
            355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 46
<211> LENGTH: 470
<212> TYPE: PRT
<213> ORGANISM: Homo sapiens

<400> SEQUENCE: 46

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Gly Tyr Ser Ser Gly Trp Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255
```

```
Pro Val Ala Gly Pro Ser Val Phe Phe Pro Lys Pro Lys Asp
                260                 265                 270

Thr Leu Met Ile Ser Arg Thr Pro Glu Val Thr Cys Val Val Asp
        275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335

Leu Asn Gly Lys Glu Tyr Lys Cys Lys Val Ser Asn Lys Gly Leu Pro
                340                 345                 350

Ala Pro Ile Glu Lys Thr Ile Ser Lys Thr Lys Gly Gln Pro Arg Glu
                355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 47
<211> LENGTH: 236
<212> TYPE: PRT
<213> ORGANISM: Homo sapiens

<400> SEQUENCE: 47

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Phe Pro Ser Ser
                20                  25                  30

Leu Ser Ala Ser Val Gly Asp Arg Val Thr Ile Thr Cys Arg Ala Ser
            35                  40                  45

Gln Gly Ile Arg Asn Asp Leu Gly Trp Tyr Gln Gln Lys Pro Gly Lys
        50                  55                  60

Ala Pro Lys Arg Leu Ile Tyr Ala Ala Ser Arg Leu His Arg Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
                100                 105                 110

His Asn Ser Tyr Pro Cys Ser Phe Gly Gln Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160
```

```
Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 48
<211> LENGTH: 236
<212> TYPE: PRT
<213> ORGANISM: Homo sapiens

<400> SEQUENCE: 48

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 49
<211> LENGTH: 470
<212> TYPE: PRT
<213> ORGANISM: Homo sapiens
```

<400> SEQUENCE: 49

```
Met Glu Phe Gly Leu Ser Trp Val Phe Leu Val Ala Ile Ile Lys Gly
 1               5                  10                  15

Val Gln Cys Gln Ala Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Asp Tyr Tyr Met Ser Trp Ile Arg Gln Ala Pro Gly Lys Gly Leu
     50                  55                  60

Glu Trp Val Ser Tyr Ile Ser Ser Ser Gly Ser Thr Arg Asp Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Thr Ala Val
            100                 105                 110

Tyr Tyr Cys Val Arg Asp Gly Val Glu Thr Thr Phe Tyr Tyr Tyr
            115                 120                 125

Tyr Gly Met Asp Val Trp Gly Gln Gly Thr Thr Val Thr Val Ser Ser
            130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

```
Thr Pro Pro Met Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
465             470

<210> SEQ ID NO 50
<211> LENGTH: 473
<212> TYPE: PRT
<213> ORGANISM: Homo sapiens

<400> SEQUENCE: 50

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Val Leu Arg Phe Leu Glu Trp Leu Leu Tyr Tyr
        115                 120                 125

Tyr Tyr Tyr Tyr Gly Met Asp Val Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320
```

-continued

```
Gln Phe Asn Ser Thr Phe Arg Val Val Ser Val Leu Thr Val Val His
                325                 330                 335

Gln Asp Trp Leu Asn Gly Lys Glu Tyr Lys Cys Lys Val Ser Asn Lys
            340                 345                 350

Gly Leu Pro Ala Pro Ile Glu Lys Thr Ile Ser Lys Thr Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 51
<211> LENGTH: 236
<212> TYPE: PRT
<213> ORGANISM: Homo sapiens

<400> SEQUENCE: 51

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Phe Thr Cys Arg Ala Ser
        35                  40                  45

Gln Asp Ile Arg Arg Asp Leu Gly Trp Tyr Gln Gln Lys Pro Gly Lys
    50                  55                  60

Ala Pro Lys Arg Leu Ile Tyr Ala Ala Ser Arg Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Asn Tyr Pro Arg Thr Phe Gly Gln Gly Thr Glu Val Glu Ile
        115                 120                 125

Ile Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205
```

```
Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 52
<211> LENGTH: 236
<212> TYPE: PRT
<213> ORGANISM: Homo sapiens

<400> SEQUENCE: 52

Met Asp Met Arg Val Pro Ala Gln Leu Leu Gly Leu Leu Leu Leu Trp
  1               5                  10                  15

Phe Pro Gly Ala Arg Cys Asp Ile Gln Met Thr Gln Ser Pro Ser Ser
                 20                  25                  30

Leu Ser Ala Ser Val Gly Asp Arg Val Thr Ile Thr Cys Arg Ala Ser
             35                  40                  45

Gln Gly Ile Arg Asn Asp Leu Gly Trp Tyr Gln Gln Lys Pro Gly Lys
         50                  55                  60

Ala Pro Lys Arg Leu Ile Tyr Ala Ala Ser Ser Leu Gln Ser Gly Val
 65                  70                  75                  80

Pro Ser Arg Phe Ser Gly Ser Gly Ser Gly Thr Glu Phe Thr Leu Thr
                 85                  90                  95

Ile Ser Ser Leu Gln Pro Glu Asp Phe Ala Thr Tyr Tyr Cys Leu Gln
            100                 105                 110

His Asn Ser Tyr Pro Trp Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 53
<211> LENGTH: 326
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: modified_base
<222> LOCATION: (289)
<223> OTHER INFORMATION: a, c, t, g, other or unknown

<400> SEQUENCE: 53
gacatccaga tgacccagty tccatcctcc ctgtctgcat ctgtaggaga cagagtcacc      60
wtcacttgcc gggcaagtca ggrcattaga mrtgatttag ctggtwtca gcagaaacca     120 gggaaagcyc ctaagcgcct gatctatgct gcatccmrwt trcammgwgg ggtcccatca    180
```

```
aggttcagcg gcagtggatc tgggacagaa ttcactctca caatcagcmg cctgcagcct      240
gaagattttg caacttatta ctgtytacar cataatartt ayccykybsns kttyggcsrr     300 gggaccrags tggaratcaw acgaac                                           326
```

<210> SEQ ID NO 54
<211> LENGTH: 322
<212> TYPE: DNA
<213> ORGANISM: Artificial Sequence
<220> FEATURE:
<223> OTHER INFORMATION: Description of Artificial Sequence: Consensus
      sequence

<400> SEQUENCE: 54

```
gacatccaga tgacccagtc tccatcctcc ctgtctgcat ctgyaggaga cagagtcacc       60
atcacttgcc gggcaagtca gagcattagy asctwtttaa attggtatca gcagaaacca     120
gggaaagccc ctaarctcct gatcyatgyt gcatccagtt trcaargtgg ggtcccatca     180
aggttcagtg gcagtggatc tgggacagat ttcactctca ccatcagcag tctgcaacct     240
gaagattttg caacttacta ctgtcaacag agttacartr ccccayychc tttcggcgga     300
gggaccaagg tggagatcaa ac                                              322
```

<210> SEQ ID NO 55
<211> LENGTH: 325
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: modified_base
<222> LOCATION: (291)
<223> OTHER INFORMATION: a, c, t, g, other or unknown

<400> SEQUENCE: 55

```
gaaattgtgt tgacgcagtc tccaggcacc ctgtctttgt ctccagggga aagagccacc       60
ctctcctgya gggccagtca gagtgttmgc rgcagstact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgtw ttactgtcag cagtatggta gytcacctcs nacgttcggc     300
caagggacca aggtggaaat caaac                                           325
```

<210> SEQ ID NO 56
<211> LENGTH: 376
<212> TYPE: DNA
<213> ORGANISM: Artificial Sequence
<220> FEATURE:
<223> OTHER INFORMATION: Description of Artificial Sequence: Consensus
      sequence

<400> SEQUENCE: 56

```
caggtgcagc tggtggagtc tgggggaggc ttggtcaagc ctggagggtc cctgagactc       60
tcctgtgcag cctctggatt cacyttcagt gactactaya tgagctggat ccgccaggct     120
ccagggaagg ggctggartg ggtttcatac attagtagta gtggtagtac cakakactac     180
gcagactctg tgaagggccc attcaccatc tccagggaca cgccaagaa ctcactgtat      240 ctgcaaatga acagcctgag agccgaggac acggccgtgt attactgtgy gagagatgga     300
```

```
gtggaaacta cttttactcc ctactactac ggtatggacg tctggggcca agggaccacg    360
gtcaccgtct cctcag                                                    376

<210> SEQ ID NO 57
<211> LENGTH: 358
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: modified_base
<222> LOCATION: (337)
<223> OTHER INFORMATION: a, c, t, g, other or unknown

<400> SEQUENCE: 57
caggtgcagc tgcaggagtc gggcccagga ctggtgaagc cttcggagac cctgtccctc    60
acctgcactg tctctggtgg ctccatcagt arttactact ggagctggat ccggcagccc   120
gccgggaagg gactggagtg gattgggcgt atctatacca gtgggagcmc caactacaac   180
ccctccctca agagtcgagt caccatgtca gtagacacgt ccaagaacca gttctccctg   240
aagctgarct ctgtgaccgc cgcggacacg gccgtgtatt actgtgcggt aacgattttt   300
ggagtggtta ttatctttga ctactggggc cagrgancc tggtcaccgt ctcctcag      358

<210> SEQ ID NO 58
<211> LENGTH: 418
<212> TYPE: DNA
<213> ORGANISM: Artificial Sequence
<220> FEATURE:
<223> OTHER INFORMATION: Description of Artificial Sequence: Consensus
      sequence

<400> SEQUENCE: 58
caggtgcagc tgttggagtc tgggggaggc ttggtacagc ctgggggtc cctgagactc    60 tcctgtrcag cctctggatt cacctttagc agctatgcca tgarctgggt ccgccaggct   120
ccagggaagg ggctggagtg gtctcagst attastggka gtggtggtab yacatwctac    180
gcagactccg tgaagggccc gttcaccatc tccagagaca attccargam cacgctgtat   240
ctgcaaatga acagcctgag agccgaggac acggccgtat attactgtgc gaaagatctk   300
ggctrsksyg actyttacta ctactactac ggtatggacg tctggggcca agggacyacg   360
gtgattatga gttggttcga ccctgggc cagggaaccc tggtcaccgt ctcctcag      418

<210> SEQ ID NO 59
<211> LENGTH: 364
<212> TYPE: DNA
<213> ORGANISM: Artificial Sequence
<220> FEATURE:
<223> OTHER INFORMATION: Description of Artificial Sequence: Consensus
      sequence

<400> SEQUENCE: 59
caggtgcagc tgcaggagtc gggcccagga ctggtgaagc cttcggagac cctgtccctc    60
acctgcactg tctctggtgg ctccatcagt agttactact ggagytggat ccggcagccc   120
ccagggaagg gactggagtg gattgggtat atctattaca gtgggagcac caactacaac   180
ccctccctca agagtcgact caccatatca gtagacacgt ccaagaacca gttctccctg   240
aagctgagyt ctgtgaccgc tgcggacacg gccgtgtatt actgtgccag gacgtatagc   300
```

-continued

```
agttcgttct actactacgg tatggacgtc tggggccaag ggaccacggt caccgtctcc    360
tcag                                                                 364
```

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Gly-Ser
      Linker

<400> SEQUENCE: 60

```
Gly Gly Gly Gly Ser Gly Gly Gly Gly Ser Gly Gly Gly Gly Ser
 1               5                  10                  15
```

ANTIBODIES TO INSULIN-LIKE GROWTH FACTOR I RECEPTOR

The present application is a continuation application of U.S. patent application Ser. No. 13/169,474, filed Jun. 27, 2011 and issued as U.S. Pat. No. 8,642,037 on Feb. 4, 2014, which is a continuation application of U.S. patent application Ser. No. 12/756,417, filed Apr. 8, 2010 and issued as U.S. Pat. No. 7,982,024 on Jul. 19, 2011, which is a divisional application of U.S. patent application Ser. No. 11/144,248, filed Jun. 2, 2005 and issued as U.S. Pat. No. 7,815,907 on Oct. 19, 2010, which is a continuation application of U.S. patent application Ser. No. 10/038,591, filed Jan. 4, 2002 and issued as U.S. Pat. No. 7,037,498 on May 2, 2006, which claims the benefit of U.S. Provisional Application No. 60/259,927, filed Jan. 5, 2001. The disclosures, including the claims, of all the aforementioned priority applications are incorporated by reference in their entirety herein.

BACKGROUND OF THE INVENTION

Insulin-like growth factor (IGF-I) is a 7.5-kD polypeptide that circulates in plasma in high concentrations and is detectable in most tissues. IGF-I stimulates cell differentiation and cell proliferation, and is required by most mammalian cell types for sustained proliferation. These cell types include, among others, human diploid fibroblasts, epithelial cells, smooth muscle cells, T lymphocytes, neural cells, myeloid cells, chondrocytes, osteoblasts and bone marrow stem cells. For a review of the wide variety of cell types for which IGF-I/IGF-I receptor interaction mediates cell proliferation, see Goldring et al., Eukar. Gene Express., 1:31-326 (1991).

The first step in the transduction pathway leading to IGF-I-stimulated cellular proliferation or differentiation is binding of IGF-I or IGF-II (or insulin at supraphysiological concentrations) to the IGF-I receptor. The IGF-I receptor is composed of two types of subunits: an alpha subunit (a 130-135 kD protein that is entirely extracellular and functions in ligand binding) and a beta subunit (a 95-kD transmembrane protein, with transmembrane and cytoplasmic domains). The IGF-IR belongs to the family of tyrosine kinase growth factor receptors (Ullrich et al., Cell 61: 203-212, 1990), and is structurally similar to the insulin receptor (Ullrich et al., EMBO J. 5: 2503-2512, 1986). The IGF-IR is initially synthesized as a single chain proreceptor polypeptide which is processed by glycosylation, proteolytic cleavage, and covalent bonding to assemble into a mature 460-kD heterotetramer comprising two alpha-subunits and two beta-subunits. The beta subunit(s) possesses ligand-activated tyrosine kinase activity. This activity is implicated in the signaling pathways mediating ligand action which involve autophosphorylation of the beta-subunit and phosphorylation of IGF-IR substrates.

In vivo, serum levels of IGF-I are dependent upon the presence of pituitary growth hormone (GH). Although the liver is a major site of GH-dependent IGF-I synthesis, recent work indicates that the majority of normal tissues also produce IGF-I. A variety of neoplastic tissues may also produce IGF-I. Thus IGF-I may act as a regulator of normal and abnormal cellular proliferation via autocrine or paracrine, as well as endocrine mechanisms. IGF-I and IGF-II bind to IGF binding proteins (IGFBPs) in vivo. The availability of free IGF for interaction with the IGF-IR is modulated by the IGFBPs. For a review of IGFBPs and IGF-I, see Grimberg et al., J. Cell. Physiol. 183: 1-9, 2000.

There is considerable evidence for a role for IGF-I and/or IGF-IR in the maintenance of tumor cells in vitro and in vivo. IGF-IR levels are elevated in tumors of lung (Kaiser et al., J. Cancer Res. Clin Oncol. 119: 665-668, 1993; Moody et al., Life Sciences 52: 1161-1173, 1993; Macauley et al., Cancer Res., 50: 2511-2517, 1990), breast (Pollak et al., Cancer Lett. 38: 223-230, 1987; Foekens et al., Cancer Res. 49: 7002-7009, 1989; Cullen et al., Cancer Res. 49: 7002-7009, 1990; Arteaga et al., J. Clin. Invest. 84: 1418-1423, 1989), prostate and colon (Remaole-Bennet et al., J. Clin. Endocrinol. Metab. 75: 609-616, 1992; Guo et al., Gastroenterol. 102: 1101-1108, 1992). Deregulated expression of IGF-I in prostate epithelium leads to neoplasia in transgenic mice (DiGiovanni et al., Proc. Natl. Acad. Sci. USA 97: 3455-60, 2000). In addition, IGF-I appears to be an autocrine stimulator of human gliomas (Sandberg-Nordqvist et al., Cancer Res. 53: 2475-2478, 1993), while IGF-I stimulated the growth of fibrosarcomas that overexpressed IGF-IR (Butler et al., Cancer Res. 58: 3021-27, 1998). Further, individuals with "high normal" levels of IGF-I have an increased risk of common cancers compared to individuals with IGF-I levels in the "low normal" range (Rosen et al., Trends Endocrinol. Metab. 10: 136-41, 1999). Many of these tumor cell types respond to IGF-I with a proliferative signal in culture (Nakanishi et al., J. Clin. Invest. 82: 354-359, 1988; Freed et al., J. Mol. Endocrinol. 3: 509-514, 1989) and autocrine or paracrine loops for proliferation in vivo have been postulated (LeRoith et al., Endocrine Revs. 16: 143-163, 1995; Yee et al., Mol. Endocrinol. 3: 509-514, 1989). For a review of the role IGF-I/IGF-I receptor interaction plays in the growth of a variety of human tumors, see Macaulay, Br. J. Cancer, 65: 311-320, 1992.

Increased IGF-I levels are also correlated with several non-cancerous pathological states, including acromegaly and gigantism (Barkan, Cleveland Clin. J. Med. 65: 343, 347-349, 1998), while abnormal IGF-I/IGF-I receptor function has been implicated in psoriasis (Wraight et al., Nat. Biotech. 18: 521-526, 2000), atherosclerosis and smooth muscle restenosis of blood vessels following angioplasty (Bayes-Genis et al., Circ. Res. 86: 125-130, 2000). Increased IGF-I levels also can be a problem in diabetes or in complications thereof, such as microvascular proliferation (Smith et al., Nat. Med. 5: 1390-1395, 1999). Decreased IGF-I levels, which occur, inter alia, in cases when GH serum levels are decreased or when there is an insensitivity or resistance to GH, is associated with such disorders as small stature (Laron, Paediatr. Drugs 1: 155-159, 1999), neuropathy, decrease in muscle mass and osteoporosis (Rosen et al., Trends Endocrinol. Metab. 10: 136-141, 1999).

Using antisense expression vectors or antisense oligonucleotides to the IGF-IR RNA, it has been shown that interference with IGF-IR leads to inhibition of IGF-1-mediated or IGF-II-mediated cell growth (see, e.g., Wraight et al., Nat. Biotech. 18: 521-526, 2000). The antisense strategy was successful in inhibiting cellular proliferation in several normal cell types and in human tumor cell lines. Growth can also be inhibited using peptide analogues of IGF-I (Pietrzkowski et al., Cell Growth & Diff. 3: 199-205, 1992; and Pietrzkowski et al., Mol. Cell. Biol., 12: 3883-3889, 1992), or a vector expressing an antisense RNA to the IGF-I RNA (Trojan et al., Science 259: 94-97, 1992). In addition, antibodies to IGF-IR (Arteaga et al., Breast Canc. Res. Treatm., 22: 101-106, 1992; and Kalebic et al., Cancer Res. 54: 5531-5534, 1994), and dominant negative mutants of IGF-IR (Prager et al., Proc. Natl. Acad. Sci. U.S.A. 91: 2181-2185, 1994; Li et al., J. Biol. Chem., 269: 32558-32564, 1994 and Jiang et al., Oncogene 18: 6071-77, 1999), can reverse the transformed phenotype, inhibit tumorigenesis, and induce loss of the metastatic phenotype.

IGF-I is also important in the regulation of apoptosis. Apoptosis, which is programmed cell death, is involved in a wide variety of developmental processes, including immune and nervous system maturation. In addition to its role in development, apoptosis also has been implicated as an important cellular safeguard against tumorigenesis (Williams, Cell 65: 1097-1098, 1991; Lane, Nature 362: 786-787, 1993). Suppression of the apoptotic program, by a variety of genetic lesions, may contribute to the development and progression of malignancies.

IGF-I protects from apoptosis induced by cytokine withdrawal in IL-3-dependent hemopoietic cells (Rodriguez-Tarduchy, G. et al., J. Immunol. 149: 535-540, 1992), and from serum withdrawal in Rat-1/mycER cells (Harrington, E., et al., EMBO J. 13: 3286-3295, 1994). The anti-apoptotic function of IGF-I is important in the post-commitment stage of the cell cycle and also in cells blocked in cell cycle progression by etoposide or thymidine. The demonstration that c-myc driven fibroblasts are dependent on IGF-I for their survival suggests that there is an important role for the IGF-IR in the maintenance of tumor cells by specifically inhibiting apoptosis, a role distinct from the proliferative effects of IGF-I or IGF-IR. This would be similar to a role thought to be played by other anti-apoptotic genes such as bcl-2 in promoting tumor survival (McDonnell et al., Cell 57: 79-88, 1989; Hockenberry et al., Nature 348: 334-336, 1990).

The protective effects of IGF-I on apoptosis are dependent upon having IGF-IR present on cells to interact with IGF-I (Resnicoff et al., Cancer Res. 55: 3739-3741, 1995). Support for an anti-apoptotic function of IGF-IR in the maintenance of tumor cells was also provided by a study using antisense oligonucleotides to the IGF-IR that identified a quantitative relationship between IGF-IR levels, the extent of apoptosis and the tumorigenic potential of a rat syngeneic tumor (Rescinoff et al., Cancer Res. 55: 3739-3741, 1995). An overexpressed IGF-IR has been found to protect tumor cells in vitro from etoposide-induced apoptosis (Sell et al., Cancer Res. 55: 303-306, 1995) and, even more dramatically, that a decrease in IGF-IR levels below wild type levels caused massive apoptosis of tumor cells in vivo (Resnicoff et al., Cancer Res. 55: 2463-2469, 1995).

Potential strategies for inducing apoptosis or for inhibiting cell proliferation associated with increased IGF-I, increased IGF-II and/or increased IGF-IR receptor levels include suppressing IGF-I levels or IGF-II levels or preventing the binding of IGF-I to the IGF-IR. For example, the long acting somatostatin analogue octreotide has been employed to reduce IGF synthesis and/or secretion. Soluble IGF-IR has been used to induce apoptosis in tumor cells in vivo and inhibit tumorigenesis in an experimental animal system (D'Ambrosio et al., Cancer Res. 56: 4013-20, 1996). In addition, IGF-IR antisense oligonucleotides, peptide analogues of IGF-I, and antibodies to IGF-IR have been used to decrease IGF-I or IGF-IR expression (see supra). However, none of these compounds has been suitable for long-term administration to human patients. In addition, although IGF-I has been administered to patients for treatment of short stature, osteoporosis, decreased muscle mass, neuropathy or diabetes, the binding of IGF-I to IGFBPs has often made treatment with IGF-I difficult or ineffective.

Accordingly, in view of the roles that IGF-I and IGF-IR have in such disorders as cancer and other proliferative disorders when IGF-I and/or IGF-IR are overexpressed, and the roles that too little IGF-I and IGF-IR have in disorders such as short stature and frailty when either IGF-I and/or IGF-IR are underexpressed, it would be desirable to generate antibodies to IGF-IR that could be used to either inhibit or stimulate IGF-IR. Although anti-IGF-IR antibodies have been reported to have been found in certain patients with autoimmune diseases, none of these antibodies has been purified and none has been shown to be suitable for inhibiting IGF-I activity for diagnostic or clinical procedures. See, e.g., Thompson et al., Pediat. Res. 32: 455-459, 1988; Tappy et al., Diabetes 37: 1708-1714, 1988; Weightman et al., Autoimmunity 16:251-257, 1993; Drexhage et al., Nether. J. of Med. 45:285-293, 1994. Thus, it would be desirable to obtain high-affinity human anti-IGF-IR antibodies that could be used to treat diseases in humans.

BRIEF DESCRIPTION OF THE DRAWINGS

FIGS. 1A-1C show alignments of the nucleotide sequences of the light chain variable regions from six human anti-IGF-IR antibodies to each other and to germline sequences. FIG. 1A shows the alignment of the nucleotide sequences of the variable region of the light chain (VL) of antibodies 2.12.1 (SEQ ID NO: 1) 2.13.2 (SEQ ID NO: 5), 2.1-4.3 (SEQ ID NO: 9) and 4.9.2 (SEQ ID NO: 13) to each other and to the germline Vκ A30 sequence (SEQ ID NO: 39). FIG. 1B shows the alignment of the nucleotide sequence of VL of antibody 4.17.3 (SEQ ID NO: 17) to the germline Vκ 012 sequence (SEQ ID NO: 41). FIG. 1C shows the alignment of the nucleotide sequence of VL of antibody 6.1.1 (SEQ ID NO: 21) to the germline Vκ A27 sequence (SEQ ID NO: 37). The alignments also show the CDR regions of the VL from each antibody. The consensus sequences for FIGS. 1A-1C are shown in SEQ ID NOS: 53-55, respectively.

FIGS. 2A-2D show alignments of the nucleotide sequences of the heavy chain variable regions from six human anti-IGF-IR antibodies to each other and to germline sequences. FIG. 2A shows the alignment of the nucleotide sequence of the VH of antibody 2.12.1 (SEQ ID NO: 3) to the germline VH DP-35 sequence (SEQ ID NO: 29). FIG. 2B shows the alignment of the nucleotide sequence of the VH of antibody 2.14.3 (SEQ ID NO: 11) to the germline VIV-4/4.35 sequence (SEQ ID NO: 43). FIGS. 2C-1 and 2C-2 show the alignments of the nucleotide sequences of the VH of antibodies 2.13.2 (SEQ ID NO: 7), 4.9.2 (SEQ ID NO: 15) and 6.1.1 (SEQ ID NO: 23) to each other and to the germline VH DP-47 sequence (SEQ ID NO: 31). FIG. 2D shows the alignment of the nucleotide sequence of the VH of antibody 4.17.3 (SEQ ID NO: 19) to the germline VH DP-71 sequence (SEQ ID NO: 35). The alignment also shows the CDR regions of the antibodies. The consensus sequences for FIGS. 2A-2D are shown in SEQ ID NOS: 56-59, respectively.

FIG. 11 shows that anti-IGF-IR antibody 2.13.2 inhibits Colo 205 tumor growth in vivo alone or in combination with 5-deoxyuridine (5-FU).

FIG. 19A shows the number of mutations in different regions of the heavy and light chains of 2.13.2 and 2.12.1 compared to the germline sequences.

FIGS. 19B-E show alignments of the amino acid sequences from the heavy and light chains of antibodies 2.13.2 and 2.12.1 with the germline sequences from which they are derived. FIG. 19B shows an alignment of the amino acid sequence of the heavy chain of antibody 2.13.2 (SEQ ID NO: 45) with that of germline sequence DP-47(3-23)/D6-19/JH6 (SEQ ID NO: 46). FIG. 19C shows an alignment of the amino acid sequence of the light chain of antibody 2.13.2 (SEQ ID NO: 47) with that of germline sequence A30/Jk2 (SEQ ID NO: 48). FIG. 19D shows an alignment of the amino acid sequence of the heavy chain of antibody 2.12.1 (SEQ ID NO: 49) with that of germline sequence DP-35(3-11)/D3-3/JH6 (SEQ ID NO: 50). FIG. 19E shows an alignment of the amino acid sequence of the light chain of antibody 2.12.1 (SEQ ID NO: 51) with that of germline sequence A30/Jk1 (SEQ ID NO: 52). For FIGS. 19B-E, the signal sequences are in italic, the CDRs are underlined, the variable domains are bold, the framework (FR) mutations are highlighted with a plus sign ("+") above the amino acid residue and CDR mutations are highlighted with an asterisk above the amino acid residue.

SUMMARY OF THE INVENTION

Figure 3:
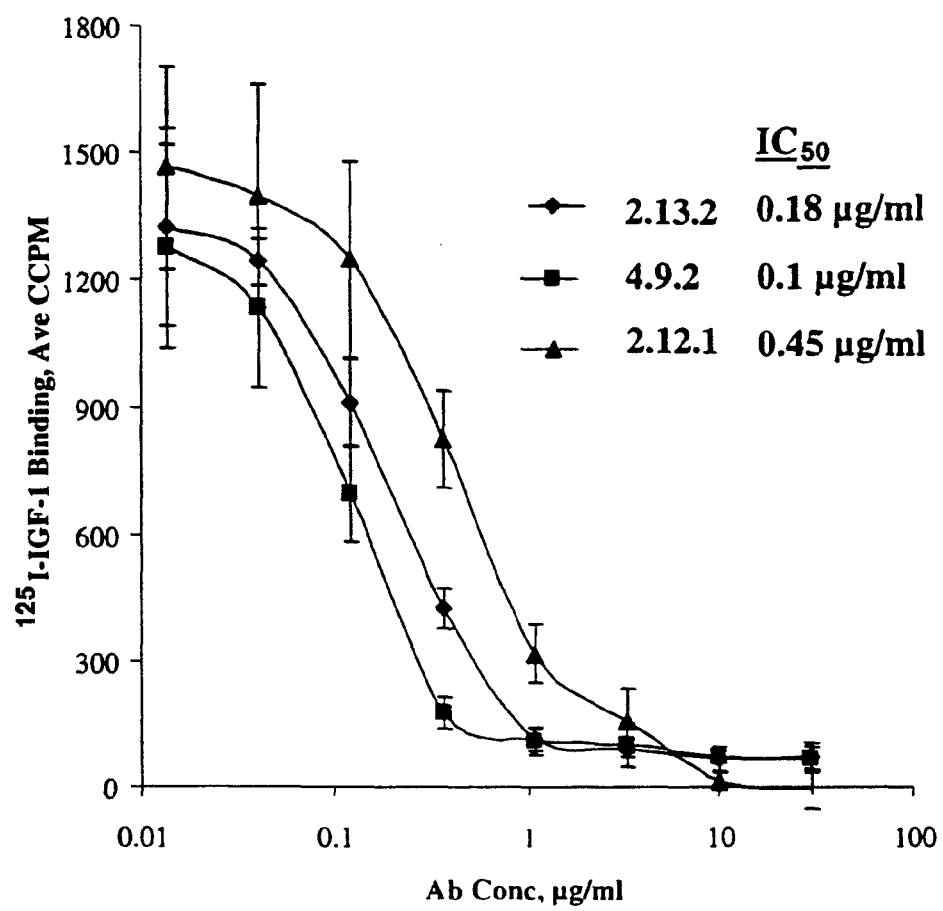
FIG. 3 shows that anti-IGF-IR antibodies 2.13.2, 4.9.2 and 2.12.1 inhibit IGF-I binding to 3T3-IGF-IR cells.

The present invention provides an isolated antibody or antigen-binding portion thereof that binds IGF-IR, preferably one that binds to primate and human IGF-IR, and more preferably one that is a human antibody. The invention provides an anti-IGF-IR antibody that inhibits the binding of IGF-I or IGF-II to IGF-IR, and also provides an anti-IGF-IR antibody that activates IGF-IR.

The invention provides a pharmaceutical composition comprising the antibody and a pharmaceutically acceptable carrier. The pharmaceutical composition may further comprise another component, such as an anti-tumor agent or an imaging reagent.

Diagnostic and therapeutic methods are also provided by the invention. Diagnostic methods include a method for diagnosing the presence or location of an IGF-IR-expressing tissue using an anti-IGF-IR antibody. A therapeutic method comprises administering the antibody to a subject in need thereof, preferably in conjunction with administration of another therapeutic agent.

The invention provides an isolated cell line, such as a hybridoma, that produces an anti-IGF-IR antibody.

The invention also provides nucleic acid molecules encoding the heavy and/or light chain or antigen-binding portions thereof of an anti-IGF-IR antibody.

The invention provides vectors and host cells comprising the nucleic acid molecules, as well as methods of recombinantly producing the polypeptides encoded by the nucleic acid molecules.

Non-human transgenic animals that express the heavy and/or light chain or antigen-binding portions thereof of an anti-IGF-IR antibody are also provided. The invention also provides a method for treating a subject in need thereof with an effective amount of a nucleic acid molecule encoding the heavy and/or light chain or antigen-binding portions thereof of an anti-IGF-IR antibody.

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2d ed., Cold Spring Harbor Laboratory Press, Cold Spring Harbor, N.Y. (1989) and Ausubel et al., *Current Protocols in Molecular Biology,* Greene Publishing Associates (1992), and Harlow and Lane *Antibodies: A Laboratory Manual* Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. Fragments typically are at least 5, 6, 8 or 10 amino acids long, preferably at least 14 amino acids long, more preferably at least 20 amino acids long, usually at least 50 amino acids long, even more preferably at least 70, 80, 90, 100, 150 or 200 amino acids long.

The term "polypeptide analog" as used herein refers to a polypeptide that is comprised of a segment of at least 25 amino acids that has substantial identity to a portion of an amino acid sequence and that has at least one of the following properties: (1) specific binding to IGF-IR under suitable binding conditions, (2) ability to block IGF-I or IGF-II binding to IGF-IR, or (3) ability to reduce IGF-IR cell surface expression or tyrosine phosphorylation in vitro or in vivo. Typically, polypeptide analogs comprise a conservative amino acid substitution (or insertion or deletion) with respect to the naturally-occurring sequence. Analogs typically are at least 20 amino acids long, preferably at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W.H. Freeman and Company, New York (1984)); *Introduction to Protein Structure* (C. Branden and J. Tooze, eds., Garland Publishing, New York, N.Y. (1991)); and Thornton et al. *Nature* 354:105 (1991), which are each incorporated herein by reference.

Non-peptide analogs are commonly used in the pharmaceutical industry as drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: $-CH_2NH-$, $-CH_2S-$, $-CH_2-CH_2-$, $-CH=CH-$(cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as κ and λ light chains. Heavy chains are classified as μ, Δ, γ, α, or ε, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

As used herein, an antibody that is referred to as, e.g., 2.12.1, 2.13.2, 2.14.3, 4.9.2, 4.17.3 and 6.1.1, is an antibody that is derived from the hybridoma of the same name. For example, antibody 2.12.1 is derived from hybridoma 2.12.1.

An Fab fragment is a monovalent fragment consisting of the VL, VH, CL and CH I domains; a F(ab')$_2$ fragment is a bivalent fragment comprising two Fab fragments linked by a disulfide bridge at the hinge region; a Fd fragment consists of the VH and CH I domains; an Fv fragment consists of the VL and VH domains of a single arm of an antibody; and a dAb fragment (Ward et al., *Nature* 341:544-546, 1989) consists of a VH domain.

A single-chain antibody (scFv) is an antibody in which a VL and VH regions are paired to form a monovalent molecules via a synthetic linker that enables them to be made as a single protein chain (Bird et al., *Science* 242:423-426, 1988 and Huston et al., *Proc. Natl. Acad. Sci. USA* 85:5879-5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., *Proc. Natl. Acad. Sci. USA* 90:6444-6448, 1993, and Poljak, R. J., et al., *Structure* 2:1121-1123, 1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. Examples of isolated antibodies include an anti-IGF-IR antibody that has been affinity purified using IGF-IR is an isolated antibody, an anti-IGF-IR antibody that has been synthesized by a hybridoma or other cell line in vitro, and a human anti-IGF-IR antibody derived from a transgenic mouse.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In a preferred embodiment, one or more of the CDRs are derived from a human anti-IGF-IR antibody. In a more preferred embodiment, all of the CDRs are derived from a human anti-IGF-IR antibody. In another preferred embodiment, the CDRs from more than one human anti-IGF-IR antibodies are mixed and matched in a chimeric antibody. For instance, a chimeric antibody may comprise a CDR1 from the light chain of a first human anti-IGF-IR antibody may be combined with CDR2 and CDR3 from the light chain of a second human anti-IGF-IR antibody, and the CDRs from the heavy chain may be derived from a third anti-IGF-IR antibody. Further, the framework regions may be derived from one of the same anti-IGF-IR antibodies, from one or more different antibodies, such as a human antibody, or from a humanized antibody.

A "neutralizing antibody" or "an inhibitory antibody" is an antibody that inhibits the binding of IGF-IR to IGF-I when an excess of the anti-IGF-IR antibody reduces the amount of IGF-I bound to IGF-IR by at least about 20%. In a preferred embodiment, the antibody reduces the amount of IGF-I bound to IGF-IR by at least 40%, more preferably 60%, even more preferably 80%, or even more preferably 85%. The binding reduction may be measured by any means known to one of ordinary skill in the art, for example, as measured in an in vitro competitive binding assay. An example of measuring the reduction in binding of IGF-I to IGF-IR is presented below in Example IV.

An "activating antibody" is an antibody that activates IGF-IR by at least about 20% when added to a cell, tissue or organism expressing IGF-IR. In a preferred embodiment, the antibody activates IGF-IR activity by at least 40%, more preferably 60%, even more preferably 80%, or even more preferably 85%. In a more preferred embodiment, the activating antibody is added in the presence of IGF-I or IGF-II. In another preferred embodiment, the activity of the activating antibody is measured by determining the amount of tyrosine autophosphorylation of IGF-IR.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991).

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$K_{off}$" refers to the off rate constant for dissociation of an antibody from the antibody/antigen complex.

The term "$K_d$" refers to the dissociation constant of a particular antibody-antigen interaction.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM, preferably ≤100 nM and most preferably ≤10 nM.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoranilidate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. An example of "high stringency" or "highly stringent" conditions is a method of incubating a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 μg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleic acid sequences refers to the residues in two sequences which are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183: 63-98 (1990); Pearson, *Methods Mol. Biol.* 132: 185-219 (2000); Pearson, *Methods Enzymol.* 266: 227-258 (1996); Pearson, *J. Mol. Biol.* 276: 71-84 (1998); herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleic acid sequence encompasses its complement unless otherwise specified. Thus, a reference to a nucleic acid molecule having a particular sequence should be understood to encompass its complementary strand, with its complementary sequence.

In the molecular biology art, researchers use the terms "percent sequence identity", "percent sequence similarity" and "percent sequence homology" interchangeably. In this application, these terms shall have the same meaning with respect to nucleic acid sequences only.

The term "substantial similarity" or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights, share at least 75% or 80% sequence identity, preferably at least 90% or 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, Methods Mol. Biol. 24: 307-31 (1994), herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., Science 256: 1443-45 (1992), herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (1990); Pearson (2000). Another preferred algorithm when comparing a sequence of the invention to a database containing a large number of sequences from different organisms is the computer program BLAST, especially blastp or tblastn, using default parameters. See, e.g., Altschul et al., J. Mol. Biol. 215: 403-410 (1990); Altschul et al., Nucleic Acids Res. 25:3389-402 (1997); herein incorporated by reference.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "agent" is used herein to denote a chemical compound, a mixture of chemical compounds, a biological macromolecule, or an extract made from biological materials. The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia Inhibition of metastasis is frequently a property of antineoplastic agents.

The term patient includes human and veterinary subjects.

Human Anti-IGF-IR Antibodies and Characterization Thereof

Human antibodies avoid certain of the problems associated with antibodies that possess mouse or rat variable and/or constant regions. The presence of such mouse or rat derived sequences can lead to the rapid clearance of the antibodies or can lead to the generation of an immune response against the antibody by a patient. Therefore, in one embodiment, the invention provides humanized anti-IGF-IR antibodies. In a preferred embodiment, the invention provides fully human anti-IGF-IR antibodies by introducing human immunoglobulin genes into a rodent so that the rodent produces fully human antibodies. More preferred are fully human anti-human IGF-IR antibodies. Fully human anti-IGF-IR antibodies are expected to minimize the immunogenic and allergic responses intrinsic to mouse or mouse-derivatized monoclonal antibodies (Mabs) and thus to increase the efficacy and safety of the administered antibodies. The use of fully human antibodies can be expected to provide a substantial advantage in the treatment of chronic and recurring human diseases, such as inflammation and cancer, which may require repeated antibody administrations. In another embodiment, the invention provides an anti-IGF-IR antibody that does not bind complement.

In a preferred embodiment, the anti-IGF-IR antibody is 2.12.1, 2.13.2, 2.14.3, 3.1.1, 4.9.2, 4.17.3 or 6.1.1. In another preferred embodiment, the anti-IGF-IR antibody comprises a light chain comprising an amino acid sequence selected from SEQ ID NO: 2, 6, 10, 14, 18 or 22, or one or more CDRs from these amino acid sequences. In another preferred embodiment, the anti-IGF-IR antibody comprises a heavy chain comprising an amino acid sequence selected from SEQ ID NO: 4, 8, 12, 16, 20 or 24 or one or more CDRs from these amino acid sequences.

Class and Subclass of Anti-IGF-IR Antibodies

The antibody may be an IgG, an IgM, an IgE, an IgA or an IgD molecule. In a preferred embodiment, the antibody is an IgG and is an IgG1, IgG2, IgG3 or IgG4 subtype. In a more preferred embodiment, the anti-IGF-IR antibody is subclass IgG2. In another preferred embodiment, the anti-IGF-IR antibody is the same class and subclass as antibody 2.12.1, 2.13.2, 2.14.3, 3.1.1, 4.9.2, 4.17.3 or 6.1.1, which is IgG2.

The class and subclass of anti-IGF-IR antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

Species and Molecule Selectivity

In another aspect of the invention, the anti-IGF-IR antibody demonstrates both species and molecule selectivity. In one embodiment, the anti-IGF-IR antibody binds to human, cynomologous or rhesus IGF-IR. In a preferred embodiment, the anti-IGF-IR antibody does not bind to mouse, rat, guinea pig, dog or rabbit IGF-IR. In another preferred embodiment, the anti-IGF-IR antibody does not bind to a New World monkey species such as a marmoset. Following the teachings of the specification, one may determine the species selectivity for the anti-IGF-IR antibody using methods well known in the art. For instance, one may determine species selectivity using Western blot, FACS, ELISA or RIA. In a preferred embodiment, one may determine the species selectivity using Western blot.

In another embodiment, the anti-IGF-IR antibody has a selectivity for IGF-IR that is at least 50 times greater than its selectivity for insulin receptor. In a preferred embodiment, the selectivity of the anti-IGF-IR antibody is more than 100 times greater than its selectivity for insulin receptor. In an even more preferred embodiment, the anti-IGF-IR antibody does not exhibit any appreciable specific binding to any other protein other than IGF-IR. One may determine the selectivity of the anti-IGF-IR antibody for IGR-IR using methods well known in the art following the teachings of the specification. For instance, one may determine the selectivity using Western blot, FACS, ELISA or RIA. In a preferred embodiment, one may determine the molecular selectivity using Western blot.

Binding Affinity of Anti-IGF-IR to IGF-IR

In another aspect of the invention, the anti-IGF-IR antibodies bind to IGF-IR with high affinity. In one embodiment, the anti-IGF-IR antibody binds to IGF-IR with a $K_d$ of $1 \times 10^{-8}$ M or less. In a more preferred embodiment, the antibody binds to IGF-IR with a $K_d$ or $1 \times 10^{-9}$ M or less. In an even more preferred embodiment, the antibody binds to IGF-IR with a $K_d$ or $5 \times 10^{-10}$ M or less. In another preferred embodiment, the antibody binds to IGF-IR with a $K_d$ or $1 \times 10^{-10}$ M or less. In another preferred embodiment, the antibody binds to IGF-IR with substantially the same $K_d$ as an antibody selected from 2.12.1, 2.13.2, 2.14.3, 3.1.1, 4.9.2, 4.17.3 or 6.1.1. In another preferred embodiment, the antibody binds to IGF-IR with substantially the same $K_d$ as an antibody that comprises one or more CDRs from an antibody selected from 2.12.1, 2.13.2, 2.14.3, 3.1.1, 4.9.2, 4.17.3 or 6.1.1. In still another preferred embodiment, the antibody binds to IGF-IR with substantially the same $K_d$ as an antibody that comprises one of the amino acid sequences selected from SEQ ID NOS: 2, 4, 6, 8, 10, 12, 14, 16, 18, 20, 22 or 24. In another preferred embodiment, the antibody binds to IGF-IR with substantially the same $K_d$ as an antibody that comprises one or more CDRs from an antibody that comprises one of the amino acid sequences selected from SEQ ID NOS: 2, 4, 6, 8, 10, 12, 14, 16, 18, 20, 22 or 24.

In another aspect of the invention, the anti-IGF-IR antibody has a low dissociation rate. In one embodiment, the anti-IGF-IR antibody has an $K_{off}$ of $1 \times 10^{-4}$ s$^{-1}$ or lower. In a preferred embodiment, the $K_{off}$ is $5 \times 10^{-5}$ s$^{-1}$ or lower. In another preferred embodiment, the $K_{off}$ is substantially the same as an antibody selected from 2.12.1, 2.13.2, 2.14.3, 3.1.1, 4.9.2, 4.17.3 or 6.1.1. In another preferred embodiment, the antibody binds to IGF-IR with substantially the same $K_{off}$ as an antibody that comprises one or more CDRs from an antibody selected from 2.12.1, 2.13.2, 2.14.3, 3.1.1, 4.9.2, 4.17.3 or 6.1.1. In still another preferred embodiment, the antibody binds to IGF-IR with substantially the same $K_{off}$ as an antibody that comprises one of the amino acid sequences selected from SEQ ID NOS: 2, 4, 6, 8, 10, 12, 14, 16, 18, 20, 22 or 24. In another preferred embodiment, the antibody binds to IGF-IR with substantially the same $K_{off}$ as an antibody that comprises one or more CDRs from an antibody that comprises one of the amino acid sequences selected from SEQ ID NOS: 2, 4, 6, 8, 10, 12, 14, 16, 18, 20, 22.

The binding affinity and dissociation rate of an anti-IGF-IR antibody to IGF-IR may be determined by any method known in the art. In one embodiment, the binding affinity can be measured by competitive ELISAs, RIAs or surface plasmon resonance, such as BIAcore. The dissociation rate can also be measured by surface plasmon resonance. In a more preferred embodiment, the binding affinity and dissociation rate is measured by surface plasmon resonance. In an even more preferred embodiment, the binding affinity and dissociation rate is measured using a BIAcore. An example of determining binding affinity and dissociation rate is described below in Example II.

Half-Life of Anti-IGF-IR Antibodies

According to another object of the invention, the anti-IGF-IR antibody has a half-life of at least one day in vitro or in vivo. In a preferred embodiment, the antibody or portion thereof has a half-life of at least three days. In a more preferred embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life, as discussed below. In another preferred embodiment, the antibody may contain point mutations to increase serum half life, such as described WO 00/09560, published Feb. 24, 2000.

The antibody half-life may be measured by any means known to one having ordinary skill in the art. For instance, the antibody half life may be measured by Western blot, ELISA or RIA over an appropriate period of time. The antibody half-life may be measured in any appropriate animals, e.g., a monkey, such as a cynomologous monkey, a primate or a human.

Identification of IGF-IR Epitopes Recognized by Anti-IGF-IR Antibody

The invention also provides an anti-IGF-IR antibody that binds the same antigen or epitope as a human anti-IGF-IR antibody. Further, the invention provides an anti-IGF-IR antibody that cross-competes with a human anti-IGF-IR antibody. In a preferred embodiment, the human anti-IGF-IR antibody is 2.12.1, 2.13.2, 2.14.3, 3.1.1, 4.9.2, 4.17.3 or 6.1.1. In another preferred embodiment, the human anti-IGF-IR comprises one or more CDRs from an antibody selected from 2.12.1, 2.13.2, 2.14.3, 3.1.1, 4.9.2, 4.17.3 or 6.1.1. In still another preferred embodiment, the human anti-IGF-IR comprises one of the amino acid sequences selected from SEQ ID NOS: 2, 4, 6, 8, 10, 12, 14, 16, 18, 20, 22 or 24. In another preferred embodiment, the human anti-IGF-IR comprises one or more CDRs from an antibody that comprises one of the amino acid sequences selected from SEQ ID NOS: 2, 4, 6, 8, 10, 12, 14, 16, 18, 20, 22 or 24. In a highly preferred embodiment, the anti-IGF-IR antibody is another human antibody.

One may determine whether an anti-IGF-IR antibody binds to the same antigen using a variety of methods known in the art. For instance, one may determine whether a test anti-IGF-IR antibody binds to the same antigen by using an anti-IGF-IR antibody to capture an antigen that is known to bind to the anti-IGF-IR antibody, such as IGF-IR, eluting the antigen from the antibody, and then determining whether the test antibody will bind to the eluted antigen. One may determine whether an antibody binds to the same epitope as an anti-IGF-IR antibody by binding the anti-IGF-IR antibody to IGF-IR under saturating conditions, and then measuring the ability of the test antibody to bind to IGF-IR. If the test antibody is able to bind to the IGF-IR at the same time as the anti-IGF-IR antibody, then the test antibody binds to a different epitope as the anti-IGF-IR antibody. However, if the test antibody is not able to bind to the IGF-IR at the same time, then the test antibody binds to the same epitope as the human anti-IGF-IR antibody. This experiment may be performed using ELISA, RIA or surface plasmon resonance. In a preferred embodiment, the experiment is performed using surface plasmon resonance. In a more preferred embodiment, BIAcore is used.

One may also determine whether an anti-IGF-IR antibody cross-competes with an anti-IGF-IR antibody. In a preferred embodiment, one may determine whether an anti-IGF-IR antibody cross-competes with another by using the same method that is used to measure whether the anti-IGF-IR antibody is able to bind to the same epitope as another anti-IGF-IR antibody.

Light and Heavy Chain Usage

The invention also provides an anti-IGF-IR antibody that comprises variable sequences encoded by a human κ gene. In a preferred embodiment, the variable sequences are encoded by either the Vκ A27, A30 or O12 gene family. In a preferred embodiment, the variable sequences are encoded by a human Vκ A30 gene family. In a more preferred embodiment, the light chain comprises no more than ten amino acid substitutions from the germline Vκ A27, A30 or O12, preferably no more than six amino acid substitutions, and more preferably no more than three amino acid substitutions. In a preferred embodiment, the amino acid substitutions are conservative substitutions.

SEQ ID NOS: 2, 6, 10, 14, 18 and 22 provide the amino acid sequences of the variable regions of six anti-IGF-IR κ light chains. SEQ ID NOS: 38, 40 and 42 provide the amino acid sequences of the three germline κ light chains from which the six anti-IGF-IR κ light chains are derived. FIGS. 1A-1C show the alignments of the nucleotide sequences of the variable regions of the light chains of the six anti-IGF-IR antibodies to each other and to the germline sequences from which they are derived. Following the teachings of this specification, one of ordinary skill in the art could determine the encoded amino acid sequence of the six anti-IGF-IR κ light chains and the germline κ light chains and determine the differences between the germline sequences and the antibody sequences.

In a preferred embodiment, the VL of the anti-IGF-IR antibody contains the same amino acid substitutions, relative to the germline amino acid sequence, as any one or more of the VL of antibodies 2.12.1, 2.13.2, 2.14.3, 3.1.1, 4.9.2, 4.17.3 or 6.1.1. For example, the VL of the anti-IGF-IR antibody may contain one or more amino acid substitutions that are the same as those present in antibody 2.13.2, another amino acid substitution that is the same as that present in antibody 2.14.3, and another amino acid substitution that is the same as antibody 4.9.2. In this manner, one can mix and match different features of antibody binding in order to alter, e.g., the affinity of the antibody for IGF-IR or its dissociation rate from the antigen. In another embodiment, the amino acid substitutions are made in the same position as those found in any one or more of the VL of antibodies 2.12.1, 2.13.2, 2.14.3, 3.1.1, 4.9.2, 4.17.3 or 6.1.1, but conservative amino acid substitutions are made rather than using the same amino acid. For example, if the amino acid substitution compared to the germline in one of the antibodies 2.12.1, 2.13.2, 2.14.3, 3.1.1, 4.9.2, 4.17.3 or 6.1.1 is glutamate, one may conservatively substitute aspartate. Similarly, if the amino acid substitution is serine, one may conservatively substitute threonine.

In another preferred embodiment, the light chain comprises an amino acid sequence that is the same as the amino acid sequence of the VL of 2.12.1, 2.13.2, 2.14.3, 3.1.1, 4.9.2, 4.17.3 or 6.1.1. In another highly preferred embodiment, the light chain comprises amino acid sequences that are the same as the CDR regions of the light chain of 2.12.1, 2.13.2, 2.14.3, 3.1.1, 4.9.2, 4.17.3 or 6.1.1. In another preferred embodiment, the light chain comprises an amino acid sequence from at least one CDR region of the light chain of 2.12.1, 2.13.2, 2.14.3, 3.1.1, 4.9.2, 4.17.3 or 6.1.1. In another preferred embodiment, the light chain comprises amino acid sequences from CDRs from different light chains. In a more preferred embodiment, the CDRs from different light chains are obtained from 2.12.1, 2.13.2, 2.14.3, 3.1.1, 4.9.2, 4.17.3 or 6.1.1. In another preferred embodiment, the light chain comprises an amino acid sequence selected from SEQ ID NOS: 2, 6, 10, 14, 18 or 22. In another embodiment, the light chain comprises an amino acid sequence encoded by a nucleic acid sequence selected from SEQ ID NOS: 1, 5, 9, 13, 17 or 21, or a nucleic acid sequence that encodes an amino acid sequence having 1-10 amino acid insertions, deletions or substitutions therefrom. Preferably, the amino acid substitutions are conservative amino acid substitutions. In another embodiment, the antibody or portion thereof comprises a lambda light chain.

The present invention also provides an anti-IGF-IR antibody or portion thereof comprises a human heavy chain or a sequence derived from a human heavy chain. In one embodiment, the heavy chain amino acid sequence is derived from a human $V_H$ DP-35, DP-47, DP-70, DP-71 or VIV-4/4.35 gene family. In a preferred embodiment, the heavy chain amino acid sequence is derived from a human $V_H$ DP-47 gene family. In a more preferred embodiment, the heavy chain comprises no more than eight amino acid changes from germline $V_H$ DP-35, DP-47, DP-70, DP-71 or VIV-4/4.35, more preferably no more than six amino acid changes, and even more preferably no more than three amino acid changes.

SEQ ID NOS: 4, 8, 12, 16, 20 and 24 provide the amino acid sequences of the variable regions of six anti-IGF-IR heavy chains. SEQ ID NOS: 30, 32, 34, 36 and 44 provide the amino acid sequences and SEQ ID NOS: 29, 31, 33, 35 and 43 provide the nucleotide sequences of the germline heavy chains DP-35, DP-47, DP-70, DP-71 and VIV-4, respectively. FIGS. 2A-2D show the alignments of the amino acid sequences of the variable region of the six anti-IGF-IR antibodies to their corresponding germline sequences. Following the teachings of this specification, one of ordinary skill in the art could determine the encoded amino acid sequence of the six anti-IGF-IR heavy chains and the germline heavy chains and determine the differences between the germline sequences and the antibody sequences.

In a preferred embodiment, the VH of the anti-IGF-IR antibody contains the same amino acid substitutions, relative to the germline amino acid sequence, as any one or more of the VH of antibodies 2.12.1, 2.13.2, 2.14.3, 3.1.1, 4.9.2, 4.17.3 or 6.1.1. Similar to what was discussed above, the VH of the anti-IGF-IR antibody may contain one or more amino acid substitutions that are the same as those present in antibody 2.13.2, another amino acid substitution that is the same as that present in antibody 2.14.3, and another amino acid substitution that is the same as antibody 4.9.2. In this manner, one can mix and match different features of antibody binding in order to alter, e.g., the affinity of the antibody for IGF-IR or its dissociation rate from the antigen. In another embodiment, the amino acid substitutions are made in the same position as those found in any one or more of the VH of antibodies 2.12.1, 2.13.2, 2.14.3, 3.1.1, 4.17.3., 4.9.2 or 6.1.1, but conservative amino acid substitutions are made rather than using the same amino acid.

In another preferred embodiment, the heavy chain comprises an amino acid sequence that is the same as the amino acid sequence of the VH of 2.12.1, 2.13.2, 2.14.3, 3.1.1, 4.9.2, 4.17.3 or 6.1.1. In another highly preferred embodiment, the heavy chain comprises amino acid sequences that are the same as the CDR regions of the heavy chain of 2.12.1, 2.13.2, 2.14.3, 3.1.1, 4.9.2, 4.17.3 or 6.1.1. In another preferred embodiment, the heavy chain comprises an amino acid sequence from at least one CDR region of the heavy chain of 2.12.1, 2.13.2, 2.14.3, 3.1.1, 4.9.2, 4.17.3 or 6.1.1. In another preferred embodiment, the heavy chain comprises amino acid sequences from CDRs from different heavy chains. In a more preferred embodiment, the CDRs from different heavy chains are obtained from 2.12.1, 2.13.2, 2.14.3, 3.1.1, 4.9.2, 4.17.3 or 6.1.1. In another preferred embodiment, the heavy chain comprises an amino acid sequence selected from SEQ ID NOS: 4, 8, 12, 16, 20 or 24. In another embodiment, the heavy chain comprises an amino acid sequence encoded by a nucleic acid sequence selected from SEQ ID NOS: 3, 7, 11, 15, 19 or 23, or a nucleic acid sequence that encodes an amino acid sequence having 1-10 amino acid insertions, deletions or substitutions therefrom. In another embodiment, the substitutions are conservative amino acid substitutions.

Inhibition of IGF-IR Activity by Anti-IGF-IR Antibody

Inhibition of IGF-I Binding to IGF-IR

In another embodiment, the invention provides an anti-IGF-IR antibody that inhibits the binding of IGF-I to IGF-IR or the binding of IGF-II to IGF-IR. In a preferred embodiment, the IGF-IR is human. In another preferred embodiment, the anti-IGF-IR antibody is a human antibody. In another embodiment, the antibody or portion thereof inhibits binding between IGF-IR and IGF-I with an $IC_{50}$ of no more than 100 nM. In a preferred embodiment, the $IC_{50}$ is no more than 10 nM. In a more preferred embodiment, the $IC_{50}$ is no more than 5 nM. The $IC_{50}$ can be measured by any method known in the art. Typically, an $IC_{50}$ can be measured by ELISA or RIA. In a preferred embodiment, the $IC_{50}$ is measured by RIA.

In another embodiment, the invention provides an anti-IGF-IR antibody that prevents activation of the IGF-IR in the presence of IGF-I. In a preferred embodiment, the anti-IGF-IR antibody inhibits IGF-IR-induced tyrosine phosphorylation that occurs upon occupancy of the receptor. In another preferred embodiment, the anti-IGF-IR antibody inhibits downstream cellular events from occurring. For instance, the anti-IGF-IR can inhibit tyrosine phosphorylation of Shc and insulin receptor substrate (IRS) 1 and 2, all of which are normally phosphorylated when cells are treated with IGF-I (Kim et al., J. Biol. Chem. 273: 34543-34550, 1998). One can determine whether an anti-IGF-IR antibody can prevent activation of IGF-IR in the presence of IGF-1 by determining the levels of autophosphorylation for IGF-IR, Shc, IRS-1 or IRS-2 by Western blot or immunoprecipitation. In a preferred embodiment, one would determine the levels of autophosphorylation of IGF-IR by Western blot. See, e.g., Example VII.

In another aspect of the invention, the antibody causes the downregulation of IGF-IR from a cell treated with the antibody. In one embodiment, the IGF-IR is internalized into the cytoplasm of the cell. After the anti-IGF-IR antibody binds to IGF-IR, the antibody is internalized, as shown by confocal microscopy. Without wishing to be bound to any theory, it is believed that the antibody-IGF-IR complex is internalized into a lysosome and degraded. One may measure the downregulation of IGF-IR by any method known in the art including immunoprecipitation, confocal microscopy or Western blot. See, e.g., Example VII. In a preferred embodiment, the antibody is selected 2.12.1, 2.13.2, 2.14.3, 3.1.1, 4.9.2, or 6.1.1, or comprises a heavy chain, light chain or antigen-binding region thereof.

Activation of IGF-IR by Anti-IGF-IR Antibody

Another aspect of the present invention involves activating anti-IGF-IR antibodies. An activating antibody differs from an inhibiting antibody because it amplifies or substitutes for the effects of IGF-I on IGF-IR. In one embodiment, the activating antibody is able to bind to IGF-IR and cause it to be activated in the absence of IGF-I. This type of activating antibody is essentially a mimic of IGF-I. In another embodiment, the activating antibody amplifies the effect of IGF-I on IGF-IR. This type of antibody does not activate IGF-IR by itself, but rather increases the activation of IGF-IR in the presence of IGF-I. A mimic anti-IGF-IR antibody may be easily distinguished from an amplifying anti-IGF-IR antibody by treating cells in vitro with an antibody in the presence or absence of low levels of IGF-I. If the antibody is able to cause IGF-IR activation in the absence of IGF-I, e.g., it increases IGF-IR tyrosine phosphorylation, then the antibody is a mimic antibody. If the antibody cannot cause IGF-IR activation in the absence of IGF-I but is able to amplify the amount of IGF-IR activation, then the antibody is an amplifying antibody. In a preferred embodiment, the activating antibody is 4.17.3. In another preferred embodiment, the antibody comprises one or more CDRs from 4.17.3. In another preferred embodiment, the antibody is derived from either or both of the germline sequences O12 (light chain) and/or D71 (heavy chain).

Inhibition of IGF-IR Tyrosine Phosphorylation, IGF-IR Levels and Tumor Cell Growth In Vivo by Anti-IGF-IR Antibodies Another embodiment of the invention provides an anti-IGF-IR antibody that inhibits IGF-IR tyrosine phosphorylation and receptor levels in vivo. In one embodiment, administration of anti-IGF-IR antibody to an animal causes a reduction in IGF-IR phosphotyrosine signal in IGF-IR-expressing tumors. In a preferred embodiment, the anti-IGF-IR antibody causes a reduction in phosphotyrosine signal by at least 20%. In a more preferred embodiment, the anti-IGF-IR antibody causes a decrease in phosphotyrosine signal by at least 60%, more preferably 50%. In an even more preferred embodiment, the antibody causes a decrease in phosphotyrosine signal of at least 40%, more preferably 30%, even more preferably 20%. In a preferred embodiment, the antibody is administered approximately 24 hours before the levels of tyrosine phosphorylation are measured. The levels of tyrosine phosphorylation may be measured by any method known in the art, such as those described infra. See, e.g., Example III and FIG. 5. In a preferred embodiment, the antibody is selected from 2.12.1, 2.13.2, 2.14.3, 3.1.1, 4.9.2, or 6.1.1, or comprises a heavy chain, light chain or antigen-binding portion thereof.

In another embodiment, administration of anti-IGF-IR antibody to an animal causes a reduction in IGF-IR levels in IGF-IR-expressing tumors. In a preferred embodiment, the anti-IGF-IR antibody causes a reduction in receptor levels by at least 20% compared to an untreated animal. In a more preferred embodiment, the anti-IGF-IR antibody causes a decrease in receptor levels to at least 60%, more preferably 50% of the receptor levels in an untreated animal. In an even more preferred embodiment, the antibody causes a decrease in receptor levels to at least 40%, more preferably 30%. In a preferred embodiment, the antibody is administered approximately 24 hours before the IGF-IR levels are measured. The IGF-IR levels may be measured by any method known in the art, such as those described infra. See, e.g., Example VIII and FIG. 6. In a preferred embodiment, the antibody is selected from 2.12.1, 2.13.2, 2.14.3, 3.1.1, 4.9.2, or 6.1.1, or comprises a heavy chain, light chain or antigen-binding portion thereof.

In another embodiment, an anti-IGF-IR antibody inhibits tumor cell growth in vivo. The tumor cell may be derived from any cell type including, without limitation, epidermal, epithelial, endothelial, leukemia, sarcoma, multiple myeloma or mesodermal cells. Examples of tumor cells include A549 (non-small cell lung carcinoma) cells, MCF-7 cells, Colo 205 cells, 3T3/IGF-IR cells and A431 cells. In a preferred embodiment, the antibody inhibits tumor cell growth as compared to the growth of the tumor in an untreated animal. In a more preferred embodiment, the antibody inhibits tumor cell growth by 50%. In an even more preferred embodiment, the antibody inhibits tumor cell growth by 60%, 65%, 70% or 75%. In one embodiment, the inhibition of tumor cell growth is measured at least 7 days after the animals have started treatment with the antibody. In a more preferred embodiment, the inhibition of tumor cell growth is measured at least 14 days after the animals have started treatment with the antibody. In another preferred embodiment, another antineoplastic agent is administered to the animal with the anti-IGF-IR antibody. In a preferred embodiment, the antineoplastic agent is able to further inhibit tumor cell growth. In an even more preferred embodiment, the antineoplastic agent is adriamycin, taxol, tamoxifen, 5-fluorodeoxyuridine (5-FU) or CP-358,774. In a preferred embodiment, the co-administration of an antineoplastic agent and the anti-IGF-IR antibody inhibits tumor cell growth by at least 50%, more preferably 60%, 65%, 70% or 75%, more preferably 80%, 85% or 90% after a period of 22-24 days. See, e.g., FIG. 7 and Example IX. In a preferred embodiment, the antibody is selected from 2.12.1, 2.13.2, 2.14.3, 3.1.1, 4.9.2, or 6.1.1, or comprises a heavy chain, light chain or antigen-binding portion thereof.

Induction of Apoptosis by Anti-IGF-IR Antibodies

Another aspect of the invention provides an anti-IGF-IR antibody that induces cell death. In one embodiment, the antibody causes apoptosis. The antibody may induce apoptosis either in vivo or in vitro. In general, tumor cells are more sensitive to apoptosis than normal cells, such that administration of an anti-IGF-IR antibody causes apoptosis of a tumor cell preferentially to that of a normal cell. In another embodiment, the administration of an anti-IGF-IR antibody decreases levels of an enzyme, akt, which is involved in the phosphatidyl inositol (PI) kinase pathway. The PI kinase pathway, in turn, is involved in the cell proliferation and prevention of apoptosis. Thus, inhibition of akt can cause apoptosis. In a more preferred embodiment, the antibody is administered in vivo to cause apoptosis of an IGF-IR-expressing cell. In a preferred embodiment, the antibody is selected from 2.12.1, 2.13.2, 2.14.3, 3.1.1, 4.9.2, or 6.1.1, or comprises a heavy chain, light chain or antigen-binding portion thereof.

Methods of Producing Antibodies and Antibody-Producing Cell Lines

Immunization

In one embodiment of the instant invention, human antibodies are produced by immunizing a non-human animal comprising some or all of the human immunoglobulin locus with an IGF-IR antigen. In a preferred embodiment, the non-human animal is a XENOMOUSE™, which is an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE™ produces an adult-like human repertoire of fully human antibodies, and generates antigen-specific human Mabs. A second generation XENOMOUSE™ contains approximately 80% of the human antibody repertoire through introduction of megabase sized, germline configuration YAC fragments of the human heavy chain loci and κ light chain loci. See Mendez et al. *Nature Genetics* 15:146-156 (1997), Green and Jakobovits *J. Exp. Med.* 188:483-495 (1998), the disclosures of which are hereby incorporated by reference.

The invention also provides a method for making anti-IGF-IR antibodies from non-human, non-mouse animals by immunizing non-human transgenic animals that comprise human immunoglobulin loci. One may produce such animals using the methods described immediately above. The methods disclosed in these patents may modified as described in U.S. Pat. No. 5,994,619. In a preferred embodiment, the non-human animals may be rats, sheep, pigs, goats, cattle or horses.

In another embodiment, the non-human animal comprising human immunoglobulin gene loci are animals that have a "minilocus" of human immunoglobulins. In the minilocus approach, an exogenous Ig locus is mimicked through the inclusion of individual genes from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described, inter alia, in U.S. Pat. Nos. 5,545,807, 5,545,806, 5,625,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

An advantage of the minilocus approach is the rapidity with which constructs including portions of the Ig locus can be generated and introduced into animals. However, a potential disadvantage of the minilocus approach is that there may not be sufficient immunoglobulin diversity to support full B-cell development, such that there may be lower antibody production.

In order to produce a human anti-IGF-IR antibody, a non-human animal comprising some or all of the human immunoglobulin loci is immunized with an IGF-IR antigen and the antibody or the antibody-producing cell is isolated from the animal. The IGF-IR antigen may be isolated and/or purified IGF-IR and is preferably a human IGF-IR. In another embodiment, the IGF-IR antigen is a fragment of IGF-IR, preferably the extracellular domain of IGF-IR. In another embodiment, the IGF-IR antigen is a fragment that comprises at least one epitope of IGF-IR. In another embodiment, the IGF-IR antigen is a cell that expresses IGF-IR on its cell surface, preferably a cell that overexpresses IGF-IR on its cell surface.

Immunization of animals may be done by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane and U.S. Pat. No. 5,994,619. In a preferred embodiment, the IGF-IR antigen is administered with a adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Example I provides an protocol for immunizing a XENOMOUSE™ with full-length human IGF-IR in phosphate-buffered saline.

Production of Antibodies and Antibody-Producing Cell Lines

After immunization of an animal with an IGF-IR antigen, antibodies and/or antibody-producing cells may be obtained from the animal. An anti-IGF-IR antibody-containing serum is obtained from the animal by bleeding or sacrificing the animal. The serum may be used as it is obtained from the animal, an immunoglobulin fraction may be obtained from the serum, or the anti-IGF-IR antibodies may be purified from the serum. Serum or immunoglobulins obtained in this manner are polyclonal, which are disadvantageous because the amount of antibodies that can be obtained is limited and the polyclonal antibody has a heterogeneous array of properties.

In another embodiment, antibody-producing immortalized hybridomas may be prepared from the immunized animal. After immunization, the animal is sacrificed and the splenic B cells are fused to immortalized myeloma cells as is well-known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using IGF-IR, a portion thereof, or a cell expressing IGF-IR. In a preferred embodiment, the initial screening is performed using an enzyme-linked immunoassay (ELISA) or a radioimmunoassay (RIA), preferably an ELISA. An example of ELISA screening is provided in WO 00/37504, herein incorporated by reference.

In another embodiment, antibody-producing cells may be prepared from a human who has an autoimmune disorder and who expresses anti-IGF-IR antibodies. Cells expressing the anti-IGF-IR antibodies may be isolated by isolating white blood cells and subjecting them to fluorescence-activated cell sorting (FACS) or by panning on plates coated with IGF-IR or a portion thereof. These cells may be fused with a human non-secretory myeloma to produce human hybridomas expressing human anti-IGF-IR antibodies. In general, this is a less preferred embodiment because it is likely that the anti-IGF-IR antibodies will have a low affinity for IGF-IR.

Anti-IGF-IR antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

Preferably, the immunized animal is a non-human animal that expresses human immunoglobulin genes and the splenic B cells are fused to a myeloma derived from the same species as the non-human animal. More preferably, the immunized animal is a XENOMOUSE™ and the myeloma cell line is a non-secretory mouse myeloma, such as the myeloma cell line is NSO-bcl2. See, e.g., Example I.

In one aspect, the invention provides hybridomas are produced that produce human anti-IGF-IR antibodies. In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-IGF-IR antibody.

Nucleic Acids, Vectors, Host Cells and Recombinant Methods of Making Antibodies

Nucleic Acids

Nucleic acid molecules encoding anti-IGF-IR antibodies of the invention are provided. In one embodiment, the nucleic acid molecule encodes a heavy and/or light chain of an anti-IGF-IR immunoglobulin. In a preferred embodiment, a single nucleic acid molecule encodes a heavy chain of an anti-IGF-IR immunoglobulin and another nucleic acid molecule encodes the light chain of an anti-IGF-IR immunoglobulin. In a more preferred embodiment, the encoded immunoglobulin is a human immunoglobulin, preferably a human IgG. The encoded light chain may be a λ chain or a κ chain, preferably a κ chain.

The nucleic acid molecule encoding the variable region of the light chain may be derived from the A30, A27 or O12 Vκ gene. In a preferred embodiment, the light chain is derived from the A30 Vκ gene. In another preferred embodiment, the nucleic acid molecule encoding the light chain comprises the joining region derived from Jκ1, Jκ2 or Jκ4. In an even more preferred embodiment, the nucleic acid molecule encoding the light chain contains no more than ten amino acid changes from the germline A30 Vκ gene, preferably no more than six amino acid changes, and even more preferably no more than three amino acid changes.

The invention provides a nucleic acid molecule that encodes a variable region of the light chain (VL) containing at least three amino acid changes compared to the germline sequence, wherein the amino acid changes are identical to the amino acid changes from the germline sequence from the VL of one of the antibodies 2.12.1, 2.13.2, 2.14.3, 3.1.1, 4.9.2, 4.17.3 or 6.1.1. The invention also provides a nucleic acid molecule comprising a nucleic acid sequence that encodes the amino acid sequence of the variable region of the light chain of 2.12.1, 2.13.2, 2.14.3, 3.1.1, 4.9.2, 4.17.3 or 6.1.1. The invention also provides a nucleic acid molecule comprising a nucleic acid sequence that encodes the amino acid sequence of one or more of the CDRs of any one of the light chains of 2.12.1, 2.13.2, 2.14.3, 3.1.1, 4.9.2, 4.17.3 or 6.1.1. In a preferred embodiment, the nucleic acid molecule comprises a nucleic acid sequence that encodes the amino acid sequence of all of the CDRs of any one of the light chains of 2.12.1, 2.13.2, 2.14.3, 3.1.1, 4.9.2, 4.17.3 or 6.1.1. In another embodiment, the nucleic acid molecule comprises a nucleic acid sequence that encodes the amino acid sequence of one of SEQ ID NOS: 2, 6, 10, 14, 18 or 22 or comprises a nucleic acid sequence of one of SEQ ID NOS: 1, 5, 9, 13, 17 or 21. In another preferred embodiment, the nucleic acid molecule comprises a nucleic acid sequence that encodes the amino acid sequence of one or more of the CDRs of any one of SEQ ID NOS: 2, 6, 10, 14, 18 or 22 or comprises a nucleic acid sequence of one or more of the CDRs of any one of SEQ ID NOS: 1, 5, 9, 13, 17 or 21. In a more preferred embodiment, the nucleic acid molecule comprises a nucleic acid sequence that encodes the amino acid sequence of all of the CDRs of any one of SEQ ID NOS: 2, 6, 10, 14, 18 or 22 or comprises a nucleic acid sequence of all the CDRs of any one of SEQ ID NOS: 1, 5, 9, 13, 17 or 21.

The invention also provides a nucleic acid molecules that encodes an amino acid sequence of a VL that has an amino acid sequence that is at least 70%, 75%, 80%, 85%, 90%, 95%, 96%, 97%, 98% or 99% identical to a VL described above, particularly to a VL that comprises an amino acid sequence of one of SEQ ID NOS: 2, 6, 10, 14, 18 or 22. The invention also provides a nucleic acid sequence that is at least 70%, 75%, 80%, 85%, 90%, 95%, 96%, 97%, 98% or 99% identical to a nucleic acid sequence of one of SEQ ID NOS: 1, 5, 9, 13, 17 or 21. In another embodiment, the invention provides a nucleic acid molecule encoding a VL that hybridizes under highly stringent conditions to a nucleic acid molecule encoding a VL as described above, particularly a nucleic acid molecule that comprises a nucleic acid sequence encoding an amino acid sequence of SEQ ID NOS: 2, 6, 10, 14, 18 or 22. The invention also provides a nucleic acid sequence encoding an VL that hybridizes under highly stringent conditions to a nucleic acid molecule comprising a nucleic acid sequence of one of SEQ ID NOS: 1, 5, 9, 13, 17 or 21.

The invention also provides a nucleic acid molecule encoding the variable region of the heavy chain (VH) is derived from the DP-35, DP-47, DP-71 or VIV-4/4.35 VH gene, preferably the DP-35 VH gene. In another preferred embodiment, the nucleic acid molecule encoding the VH comprises the joining region derived from JH6 or JH5, more preferably JH6. In another preferred embodiment, the D segment is derived from 3-3, 6-19 or 4-17. In an even more preferred embodiment, the nucleic acid molecule encoding the VH contains no more than ten amino acid changes from the germline DP-47 gene, preferably no more than six amino acid changes, and even more preferably no more than three amino acid changes. In a highly preferred embodiment, the nucleic acid molecule encoding the VH contains at least one amino acid change compared to the germline sequence, wherein the amino acid change is identical to the amino acid change from the germline sequence from the heavy chain of one of the antibodies 2.12.1, 2.13.2, 2.14.3, 3.1.1, 4.9.2, 4.17.3 or 6.1.1. In an even more preferred embodiment, the VH contains at least three amino acid changes compared to the germline sequences, wherein the changes are identical to those changes from the germline sequence from the VH of one of the antibodies 2.12.1, 2.13.2, 2.14.3, 3.1.1, 4.9.2, 4.17.3 or 6.1.1.

In one embodiment, the nucleic acid molecule comprises a nucleic acid sequence that encodes the amino acid sequence of the VH of 2.12.1, 2.13.2, 2.14.3, 3.1.1, 4.9.2, 4.17.3 or 6.1.1. In another embodiment, the nucleic acid molecule comprises a nucleic acid sequence that encodes the amino acid sequence of one or more of the CDRs of the heavy chain of 2.12.1, 2.13.2, 2.14.3, 3.1.1, 4.9.2, 4.17.3 or 6.1.1. In a preferred embodiment, the nucleic acid molecule comprises a nucleic acid sequence that encodes the amino acid sequences of all of the CDRs of the heavy chain of 2.12.1, 2.13.2, 2.14.3, 3.1.1, 4.9.2, 4.17.3 or 6.1.1. In another preferred embodiment, the nucleic acid molecule comprises a nucleic acid sequence that encodes the amino acid sequence of one of SEQ ID NOS: 4, 8, 12, 16, 20 or 24 or that comprises a nucleic acid sequence of one of SEQ ID NOS: 3, 7, 11, 15, 19 or 23. In another preferred embodiment, the nucleic acid molecule comprises a nucleic acid sequence that encodes the amino acid sequence of one or more of the CDRs of any one of SEQ ID NOS: 4, 8, 12, 16, 20 or 24 or comprises a nucleic acid sequence of one or more of the CDRs of any one of SEQ ID NOS: 3, 7, 11, 15, 19 or 23. In a preferred embodiment, the nucleic acid molecule comprises a nucleic acid sequence that encodes the amino acid sequences of all of the CDRs of any one of SEQ ID NOS: 4, 8, 12, 16, 20 or 24 or comprises a nucleic acid sequence of all of the CDRs of any one of SEQ ID NOS: 3, 7, 11, 15, 19 or 23.

In another embodiment, the nucleic acid molecule encodes an amino acid sequence of a VH that is at least 70%, 75%, 80%, 85%, 90%, 95%, 96%, 97%, 98% or 99% identical to one of the amino acid sequences encoding a VH as described immediately above, particularly to a VH that comprises an amino acid sequence of one of SEQ ID NOS: 4, 8, 12, 16, 20 or 24. The invention also provides a nucleic acid sequence that is at least 70%, 75%, 80%, 85%, 90%, 95%, 96%, 97%, 98% or 99% identical to a nucleic acid sequence of one of SEQ ID NOS: 3, 7, 11, 15, 19 or 23. In another embodiment, the nucleic acid molecule encoding a VH is one that hybridizes under highly stringent conditions to a nucleic acid sequence encoding a VH as described above, particularly to a VH that comprises an amino acid sequence of one of SEQ ID NOS: 4, 8, 12, 16, 20 or 24. The invention also provides a nucleic acid sequence encoding a VH that hybridizes under highly stringent conditions to a nucleic acid molecule comprising a nucleic acid sequence of one of SEQ ID NOS: 3, 7, 11, 15, 19 or 23.

The nucleic acid molecule encoding either or both of the entire heavy and light chains of an anti-IGF-IR antibody or the variable regions thereof may be obtained from any source that produces an anti-IGF-IR antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In one embodiment of the invention, the nucleic acid molecules may be obtained from a hybridoma that expresses an anti-IGF-IR antibody, as described above, preferably a hybridoma that has as one of its fusion partners a transgenic animal cell that expresses human immunoglobulin genes, such as a XENOMOUSE™, non-human mouse transgenic animal or a non-human, non-mouse transgenic animal. In another embodiment, the hybridoma is derived from a non-human, non-transgenic animal, which may be used, e.g., for humanized antibodies.

A nucleic acid molecule encoding the entire heavy chain of an anti-IGF-IR antibody may be constructed by fusing a nucleic acid molecule encoding the variable domain of a heavy chain or an antigen-binding domain thereof with a constant domain of a heavy chain. Similarly, a nucleic acid molecule encoding the light chain of an anti-IGF-IR antibody may be constructed by fusing a nucleic acid molecule encoding the variable domain of a light chain or an antigen-binding domain thereof with a constant domain of a light chain. The nucleic acid molecules encoding the VH and VL chain may be converted to full-length antibody genes by inserting them into expression vectors already encoding heavy chain constant and light chain constant regions, respectively, such that the VH segment is operatively linked to the heavy chain constant region (CH) segment(s) within the vector and the VL segment is operatively linked to the light chain constant region (CL) segment within the vector. Alternatively, the nucleic acid molecules encoding the VH or VL chains are converted into full-length antibody genes by linking, e.g., ligating, the nucleic acid molecule encoding a VH chain to a nucleic acid molecule encoding a CH chain using standard molecular biological techniques. The same may be achieved using nucleic acid molecules encoding VL and CL chains. The sequences of human heavy and light chain constant region genes are known in the art. See, e.g., Kabat et al., *Sequences of Proteins of Immunological Interest*, 5th Ed., NIH Publ. No. 91-3242, 1991. Nucleic acid molecules encoding the full-length heavy and/or light chains may then be expressed from a cell into which they have been introduced and the anti-IGF-IR antibody isolated.

In a preferred embodiment, the nucleic acid encoding the variable region of the heavy chain encodes the amino acid sequence of SEQ ID NOS: 4, 8, 12, 16, 20 or 24, and the nucleic acid molecule encoding the variable region of the light chains encodes the amino acid sequence of SEQ ID NOS: 2, 6, 10, 14, 18 or 22. SEQ ID NO: 28 depicts the amino acid sequence and SEQ ID NO: 27 depicts the nucleic acid sequence encoding the constant region of the heavy chain of the anti-IGF-IR antibodies 2.12.1, 2.13.2, 2.14.3, 3.1.1, 4.9.2, 4.17.3 and 6.1.1. SEQ ID NO: 26 depicts the amino acid sequence and SEQ ID NO: 25 depicts the nucleic acid sequence encoding the constant region of the light chain of the anti-IGF-IR antibodies 2.12.1, 2.13.2, 2.14.3, 3.1.1, 4.9.2, 4.17.3 and 6.1.1. Thus, in a preferred embodiment, the nucleic acid molecule encoding the constant domain of the heavy chain encodes SEQ ID NO: 28, and the nucleic acid molecule encoding the constant domain of the light chain encodes SEQ ID NO: 26. In a more preferred embodiment, the nucleic acid molecule encoding the constant domain of the heavy chain has the nucleic acid sequence of SEQ ID NO: 27, and the nucleic acid molecule encoding the constant domain has the nucleic acid sequence of SEQ ID NO: 25.

In another embodiment, a nucleic acid molecule encoding either the heavy chain of an anti-IGF-IR antibody or an antigen-binding domain thereof, or the light chain of an anti-IGF-IR antibody or an antigen-binding domain thereof may be isolated from a non-human, non-mouse animal that expresses human immunoglobulin genes and has been immunized with an IGF-IR antigen. In other embodiment, the nucleic acid molecule may be isolated from an anti-IGF-IR antibody-producing cell derived from a non-transgenic animal or from a human patient who produces anti-IGF-IR antibodies. Methods of isolating mRNA from the anti-IGF-IR antibody-producing cells may be isolated by standard techniques, cloned and/or amplified using PCR and library construction techniques, and screened using standard protocols to obtain nucleic acid molecules encoding anti-IGF-IR heavy and light chains.

The nucleic acid molecules may be used to recombinantly express large quantities of anti-IGF-IR antibodies, as described below. The nucleic acid molecules may also be used to produce chimeric antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, the nucleic acid molecules of the invention may be used as probes or PCR primers for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable domains of anti-IGF-IR antibodies. In a preferred embodiment, the nucleic acid molecules are oligonucleotides. In a more preferred embodiment, the oligonucleotides are from highly variable regions of the heavy and light chains of the antibody of interest. In an even more preferred embodiment, the oligonucleotides encode all or a part of one or more of the CDRs.

Vectors

The invention provides vectors comprising the nucleic acid molecules of the invention that encode the heavy chain or the antigen-binding portion thereof. The invention also provides vectors comprising the nucleic acid molecules of the invention that encode the light chain or antigen-binding portion thereof. The invention also provides vectors comprising nucleic acid molecules encoding fusion proteins, modified antibodies, antibody fragments, and probes thereof.

To express the antibodies, or antibody portions of the invention, DNAs encoding partial or full-length light and heavy chains, obtained as described above, are inserted into expression vectors such that the genes are operatively linked to transcriptional and translational control sequences. Expression vectors include plasmids, retroviruses, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

Non-Hybridoma Host Cells and Methods of Recombinantly Producing Protein

Nucleic acid molecules encoding the heavy chain or an antigen-binding portion thereof and/or the light chain or an antigen-binding portion thereof of an anti-IGF-IR antibody, and vectors comprising these nucleic acid molecules, can be used for transformation of a suitable mammalian host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference).

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic Animals

The invention also provides transgenic non-human animals comprising one or more nucleic acid molecules of the invention that may be used to produce antibodies of the invention. Antibodies can be produced in and recovered from tissue or bodily fluids, such as milk, blood or urine, of goats, cows, horses, pigs, rats, mice, rabbits, hamsters or other mammals. See, e.g., U.S. Pat. Nos. 5,827,690, 5,756,687, 5,750,172, and 5,741,957. As described above, non-human transgenic animals that comprise human immunoglobulin loci can be produced by immunizing with IGF-IR or a portion thereof.

In another embodiment, non-human transgenic animals are produced by introducing one or more nucleic acid molecules of the invention into the animal by standard transgenic techniques. See Hogan, supra. The transgenic cells used for making the transgenic animal can be embryonic stem cells or somatic cells. The transgenic non-human organisms can be chimeric, nonchimeric heterozygotes, and nonchimeric homozygotes. See, e.g., Hogan et al., *Manipulating the Mouse Embryo: A Laboratory Manual* 2ed., Cold Spring Harbor Press (1999); Jackson et al., *Mose Genetics and Transgenics: A Practical Approach*, Oxford University Press (2000); and Pinkert, *Transgenic Animal Technology: A Laboratory Handbook*, Academic Press (1999). In another embodiment, the transgenic non-human organisms may have a targeted disruption and replacement that encodes a heavy chain and/or a light chain of interest. In a preferred embodiment, the transgenic animals comprise and express nucleic acid molecules encoding heavy and light chains that bind specifically to IGF-IR, preferably human IGF-IR. In another embodiment, the transgenic animals comprise nucleic acid molecules encoding a modified antibody such as a single-chain antibody, a chimeric antibody or a humanized antibody. The anti-IGF-IR antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-IGF-IR antibody or antigen-binding portion thereof comprising the steps of synthesizing a library of human antibodies on phage, screening the library with a IGF-IR or a portion thereof, isolating phage that bind IGF-IR, and obtaining the antibody from the phage. One method to prepare the library of antibodies comprises the steps of immunizing a non-human host animal comprising a human immunoglobulin locus with IGF-IR or an antigenic portion thereof to create an immune response, extracting cells from the host animal the cells that are responsible for production of antibodies; isolating RNA from the extracted cells, reverse transcribing the RNA to produce cDNA, amplifying the cDNA using a primer, and inserting the cDNA into phage display vector such that antibodies are expressed on the phage. Recombinant anti-IGF-IR antibodies of the invention may be obtained in this way.

Recombinant anti-IGF-IR human antibodies of the invention in addition to the anti-IGF-IR antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum. Antibod. Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc Acid Res 19:4133-4137; and Barbas et al. (1991) Proc. Natl. Acad. Sci. USA 88:7978-7982.

In a preferred embodiment, to isolate human anti-IGF-IR antibodies with the desired characteristics, a human anti-IGF-IR antibody as described herein is first used to select human heavy and light chain sequences having similar binding activity toward IGF-IR, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., Nature (1990) 348:552-554; and Griffiths et al., (1993) EMBO J 12:725-734. The scFv antibody libraries preferably are screened using human IGF-IR as the antigen.

Once initial human VL and VH segments are selected, "mix and match" experiments, in which different pairs of the initially selected VL and VH segments are screened for IGF-IR binding, are performed to select preferred VL/VH pair combinations. Additionally, to further improve the quality of the antibody, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to IGF-IR.

Following screening and isolation of an anti-IGF-IR antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Class Switching

Another aspect of the instant invention is to provide a mechanism by which the class of an anti-IGF-IR antibody may be switched with another. In one aspect of the invention, a nucleic acid molecule encoding VL or VH is isolated using methods well-known in the art such that it does not include any nucleic acid sequences encoding CL or CH. The nucleic acid molecule encoding VL or VH are then operatively linked to a nucleic acid sequence encoding a CL or CH from a different class of immunoglobulin molecule. This may be achieved using a vector or nucleic acid molecule that comprises a CL or CH chain, as described above. For example, an anti-IGF-IR antibody that was originally IgM may be class switched to an IgG. Further, the class switching may be used to convert one IgG subclass to another, e.g., from IgG1 to IgG2. A preferred method for producing an antibody of the invention comprising a desired isotypes comprises the steps of isolating a nucleic acid encoding the heavy chain of an anti-IGF-IR antibody and a nucleic acid encoding the light chain of an anti-IGF-IR antibody, obtaining the variable region of the heavy chain, ligating the variable region of the heavy chain with the constant domain of a heavy chain of the desired isotype, expressing the light chain and the ligated heavy chain in a cell, and collecting the anti-IGF-IR antibody with the desired isotype.

Antibody Derivatives

One may use the nucleic acid molecules described above to generate antibody derivatives using techniques and methods known to one of ordinary skill in the art.

Humanized Antibodies

As was discussed above in connection with human antibody generation, there are advantages to producing antibodies with reduced immunogenicity. This can be accomplished to some extent using techniques of humanization and display techniques using appropriate libraries. It will be appreciated that murine antibodies or antibodies from other species can be humanized or primatized using techniques well known in the art. See e.g., Winter and Harris *Immunol Today* 14:43-46 (1993) and Wright et al. *Grit. Reviews in Immunol.* 12125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714, 350, and 5,777,085). In a preferred embodiment, the anti-IGF-IR antibody can be humanized by substituting the CH1, CH2, CH3, hinge domains, and/or the framework domain with the corresponding human sequence while maintaining all of the CDRS of the heavy chain, the light chain or both the heavy and light chains.

Mutated Antibodies

In another embodiment, the nucleic acid molecules, vectors and host cells may be used to make mutated anti-IGF-IR antibodies. The antibodies may be mutated in the variable domains of the heavy and/or light chains to alter a binding property of the antibody. For example, a mutation may be made in one or more of the CDR regions to increase or decrease the $K_d$ of the antibody for IGF-IR, to increase or decrease $K_{off}$, or to alter the binding specificity of the antibody. Techniques in site-directed mutagenesis are well-known in the art. See, e.g., Sambrook et al. and Ausubel et al., supra. In a preferred embodiment, mutations are made at an amino acid residue that is known to be changed compared to germline in a variable region of an anti-IGF-IR antibody. In a more preferred embodiment, one or more mutations are made at an amino acid residue that is known to be changed compared to the germline in a variable region or CDR region of one of the anti-IGF-IR antibodies 2.12.1, 2.13.2, 2.14.3, 3.1.1, 4.9.2, 4.17.3 or 6.1.1. In another embodiment, one or more mutations are made at an amino acid residue that is known to be changed compared to the germline in a variable region or CDR region whose amino acid sequence is presented in SEQ ID NOS: 2, 4, 6, 8, 10, 12, 14, 16, 18, 20, 22 or 24, or whose nucleic acid sequence is presented in SEQ ID NOS: 1, 3, 5, 7, 9, 11, 13, 15, 17, 19, 21 or 23. In another embodiment, the nucleic acid molecules are mutated in one or more of the framework regions. A mutation may be made in a framework region or constant domain to increase the half-life of the anti-IGF-IR antibody. See, e.g., WO 00/09560, published Feb. 24, 2000, herein incorporated by reference. In one embodiment, there may be one, three or five point mutations and no more than ten point mutations. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

In one embodiment, there are no greater than ten amino acid changes in either the VH or VL regions of the mutated anti-IGF-IR antibody compared to the anti-IGF-IR antibody prior to mutation. In a more preferred embodiment, there is no more than five amino acid changes in either the VH or VL regions of the mutated anti-IGF-IR antibody, more preferably no more than three amino acid changes. In another embodiment, there are no more than fifteen amino acid changes in the constant domains, more preferably, no more than ten amino acid changes, even more preferably, no more than five amino acid changes.

Modified Antibodies

In another embodiment, a fusion antibody or immunoadhesin may be made which comprises all or a portion of an anti-IGF-IR antibody linked to another polypeptide. In a preferred embodiment, only the variable regions of the anti-IGF-IR antibody are linked to the polypeptide. In another preferred embodiment, the VH domain of an anti-IGF-IR antibody are linked to a first polypeptide, while the VL domain of an anti-IGF-IR antibody are linked to a second polypeptide that associates with the first polypeptide in a manner in which the VH and VL domains can interact with one another to form an antibody binding site. In another preferred embodiment, the VH domain is separated from the VL domain by a linker such that the VH and VL domains can interact with one another (see below under Single Chain Antibodies). The VH-linker-VL antibody is then linked to the polypeptide of interest. The fusion antibody is useful to directing a polypeptide to an IGF-IR-expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the VH- and VL-encoding DNA fragments are operatively linked to another fragment encoding a flexible linker, e.g., encoding the amino acid sequence (Gly$_4$-Ser)$_3$ (SEQ ID NO: 60), such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554). The single chain antibody may be monovalent, if only a single VH and VL are used, bivalent, if two VH and VL are used, or polyvalent, if more than two VH and VL are used.

In another embodiment, other modified antibodies may be prepared using anti-IGF-IR-encoding nucleic acid molecules. For instance, "Kappa bodies" (Ill et al., *Protein Eng* 10: 949-57 (1997)), "Minibodies" (Martin et al., *EMBO J.* 13: 5303-9 (1994)), "Diabodies" (Holliger et al., PNAS USA 90: 6444-6448 (1993)), or "Janusins" (Traunecker et al., *EMBO J* 10: 3655-3659 (1991) and Traunecker et al. "Janusin: new molecular design for bispecific reagents" *Int J Cancer Suppl* 7:51-52 (1992)) may be prepared using standard molecular biological techniques following the teachings of the specification.

In another aspect, chimeric and bispecific antibodies can be generated. A chimeric antibody may be made that comprises CDRs and framework regions from different antibodies. In a preferred embodiment, the CDRs of the chimeric antibody comprises all of the CDRs of the variable region of a light chain or heavy chain of an anti-IGF-IR antibody, while the framework regions are derived from one or more different antibodies. In a more preferred embodiment, the CDRs of the chimeric antibody comprise all of the CDRs of the variable regions of the light chain and the heavy chain of an anti-IGF-IR antibody. The framework regions may be from another species and may, in a preferred embodiment, be humanized. Alternatively, the framework regions may be from another human antibody.

A bispecific antibody can be generated that binds specifically to IGF-IR through one binding domain and to a second molecule through a second binding domain. The bispecific antibody can be produced through recombinant molecular biological techniques, or may be physically conjugated together. In addition, a single chain antibody containing more than one VH and VL may be generated that binds specifically to IGF-IR and to another molecule. Such bispecific antibodies can be generated using techniques that are well known for example, in connection with (i) and (ii) see e.g., Fanger et al. *Immunol Methods* 4: 72-81 (1994) and Wright and Harris, supra. and in connection with (iii) see e.g., Traunecker et al. *Int. J. Cancer (Suppl.)* 7: 51-52 (1992). In a preferred embodiment, the bispecific antibody binds to IGF-IR and to another molecule expressed at high level on cancer or tumor cells. In a more preferred embodiment, the other molecule is erbB2 receptor, VEGF, CD20 or EGF-R.

In a embodiment, the modified antibodies described above are prepared using one or more of the variable regions or one or more CDR regions from one of the antibodies selected from 2.12.1, 2.13.2, 2.14.3, 3.1.1, 4.9.2, 4.17.3 or 6.1.1. In another embodiment, the modified antibodies are prepared using one or more of the variable regions or one or more CDR regions whose amino acid sequence is presented in SEQ ID NOS: 2, 4, 6, 8, 10, 12, 14, 16, 18, 20, 22 or 24, or whose nucleic acid sequence is presented in SEQ ID NOS: 1, 3, 5, 7, 9, 11, 13, 15, 17, 19, 21 or 23.

Derivatized and Labeled Antibodies

An antibody or antibody portion of the invention can be derivatized or linked to another molecule (e.g., another peptide or protein). In general, the antibodies or portion thereof is derivatized such that the IGF-IR binding is not affected adversely by the derivatization or labeling. Accordingly, the antibodies and antibody portions of the invention are intended to include both intact and modified forms of the human anti-IGF-IR antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antibody portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody may also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labeled with biotin, and detected through indirect measurement of avidin or streptavidin binding. An antibody may be labeled with a magnetic agent, such as gadolinium. An antibody may also be labeled with a predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-IGF-IR antibody may also be labeled with a radiolabeled amino acid. The radiolabel may be used for both diagnostic and therapeutic purposes. For instance, the radiolabel may be used to detect IGF-IR-expressing tumors by x-ray or other diagnostic techniques. Further, the radiolabel may be used therapeutically as a toxin for cancerous cells or tumors. Examples of labels for polypeptides include, but are not limited to, the following radioisotopes or radionuclides—$^{3}H$, $^{14}C$, $^{15}N$, $^{35}S$, $^{90}Y$, $^{99}Tc$, $^{111}In$, $^{125}I$, $^{131}I$.

An anti-IGF-IR antibody may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

Pharmaceutical Compositions and Kits

The invention also relates to a pharmaceutical composition for the treatment of a hyperproliferative disorder in a mammal which comprises a therapeutically effective amount of a compound of the invention and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, esophageal, gynecological or thyroid cancer. In another embodiment, said pharmaceutical composition relates to noncancerous hyperproliferative disorders such as, without limitation, restenosis after angioplasty and psoriasis. In another embodiment, the invention relates to pharmaceutical compositions for the treatment of a mammal that requires activation of IGF-IR, wherein the pharmaceutical composition comprises a therapeutically effective amount of an activating antibody of the invention and a pharmaceutically acceptable carrier. Pharmaceutical compositions comprising activating antibodies may be used to treat animals that lack sufficient IGF-I or IGF-II, or may be used to treat osteoporosis, frailty or disorders in which the mammal secretes too little active growth hormone or is unable to respond to growth hormone.

The anti-IGF-IR antibodies of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-IGF-IR antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is intraperitoneal, subcutaneous, intramuscular, intravenous or infusion. As will be appreciated by the skilled artisan, the route and/or mode of administration will vary depending upon the desired results. In one embodiment, the antibodies of the present invention can be administered as a single dose or may be administered as multiple doses.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. In certain embodiments, the anti-IGF-IR of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an anti-IGF-IR of the invention is coformulated with and/or coadministered with one or more additional therapeutic agents, such as a chemotherapeutic agent, an antineoplastic agent or an anti-tumor agent. For example, an anti-IGF-IR antibody may be coformulated and/or coadministered with one or more additional therapeutic agents. These agents include, without limitation, antibodies that bind other targets (e.g., antibodies that bind one or more growth factors or cytokines, their cell surface receptors or IGF-I), IGF-I binding proteins, antineoplastic agents, chemotherapeutic agents, anti-tumor agents, antisense oligonucleotides against IGF-IR or IGF-I, peptide analogues that block IGF-IR activation, soluble IGF-IR, and/or one or more chemical agents that inhibit IGF-I production or activity, which are known in the art, e.g., octreotide. For a pharmaceutical composition comprising an activating antibody, the anti-IGF-IR antibody may be formulated with a factor that increases cell proliferation or prevents apoptosis. Such factors include growth factors such as IGF-I, and/or analogues of IGF-I that activate IGF-IR. Such combination therapies may require lower dosages of the anti-IGF-IR antibody as well as the co-administered agents, thus avoiding possible toxicities or complications associated with the various monotherapies. In one embodiment, the antibody and one or more additional therapeutic agent.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. Pharmaceutical composition comprising the antibody or comprising a combination therapy comprising the antibody and one or more additional therapeutic agents may be formulated for single or multiple doses. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals. A particularly useful formulation is 5 mg/ml anti-IGF-IR antibody in a buffer of 20 mM sodium citrate, pH 5.5, 140 mM NaCl, and 0.2 mg/ml polysorbate 80.

An exemplary, non-limiting range for a therapeutically or prophylactically effective amount of an antibody or antibody portion of the invention is 0.1-100 mg/kg, more preferably 0.5-50 mg/kg, more preferably 1-20 mg/kg, and even more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. In one embodiment, the therapeutically or prophylactically effective amount of an antibody or antigen-binding portion thereof is administered along with one or more additional therapeutic agents.

In another aspect, the invention relates to administration of an anti-IGF-IR antibody for the treatment of cancer in a dose of less than 300 mg per month.

Another aspect of the present invention provides kits comprising the anti-IGF-IR antibodies and the pharmaceutical compositions comprising these antibodies. A kit may include, in addition to the antibody or pharmaceutical composition, diagnostic or therapeutic agents. A kit may also include instructions for use in a diagnostic or therapeutic method. In a preferred embodiment, the kit includes the antibody or a pharmaceutical composition thereof and a diagnostic agent that can be used in a method described below. In another preferred embodiment, the kit includes the antibody or a pharmaceutical composition thereof and one or more therapeutic agents, such as an additional antineoplastic agent, anti-tumor agent or chemotherapeutic agent, that can be used in a method described below.

This invention also relates to pharmaceutical compositions for inhibiting abnormal cell growth in a mammal which comprise an amount of a compound of the invention in combination with an amount of a chemotherapeutic agent, wherein the amounts of the compound, salt, solvate, or prodrug, and of the chemotherapeutic agent are together effective in inhibiting abnormal cell growth. Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, RS 13-0830, and the compounds recited in the following list: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-icyclo[3.2.1]octane-3-carboxylic acid hydroxyamide; 3-endo-3-[4-(4-fluoro-phenoxy)-benzenesulfonylamino]-8-oxa-icyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

A compound of the invention can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747, 498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183, 805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)). These and other EGF-R-inhibiting agents can be used in the present invention.

VEGF inhibitors, for example SU-5416 and SU-6668 (Sugen Inc.), SH-268 (Schering), and NX-1838 (NeXstar) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886, 020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc.); anti-VEGF monoclonal antibody of Genentech, Inc.; and angiozyme, a synthetic ribozyme from Ribozyme and Chiron. These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc.) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

Anti-survival agents include anti-IGF-IR antibodies and anti-integrin agents, such as anti-integrin antibodies.

Diagnostic Methods of Use

The anti-IGF-IR antibodies may be used to detect IGF-IR in a biological sample in vitro or in vivo. The anti-IGF-IR antibodies may be used in a conventional immunoassay, including, without limitation, an ELISA, an RIA, FACS, tissue immunohistochemistry, Western blot or immunoprecipitation. The anti-IGF-IR antibodies of the invention may be used to detect IGF-IR from humans. In another embodiment, the anti-IGF-IR antibodies may be used to detect IGF-IR from Old World primates such as cynomologous and rhesus monkeys, chimpanzees and apes. The invention provides a method for detecting anti-IGF-IR in a biological sample comprising contacting a biological sample with an anti-IGF-IR antibody of the invention and detecting the bound antibody bound to anti-IGF-IR, to detect the IGF-IR in the biological sample. In one embodiment, the anti-IGF-IR antibody is directly labeled with a detectable label. In another embodiment, the anti-IGF-IR antibody (the first antibody) is unlabeled and a second antibody or other molecule that can bind the anti-IGF-IR antibody is labeled. As is well known to one of skill in the art, a second antibody is chosen that is able to specifically bind the specific species and class of the first antibody. For example, if the anti-IGF-IR antibody is a human IgG, then the secondary antibody may be an anti-human-IgG. Other molecules that can bind to antibodies include, without limitation, Protein A and Protein G, both of which are available commercially, e.g., from Pierce Chemical Co.

Suitable labels for the antibody or secondary have been disclosed supra, and include various enzymes, prosthetic groups, fluorescent materials, luminescent materials, magnetic agents and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; an example of a magnetic agent includes gadolinium; and examples of suitable radioactive material include $^{125}$I, $^{131}$I, $^{35}$S or $^{3}$H.

In an alternative embodiment, IGF-IR can be assayed in a biological sample by a competition immunoassay utilizing IGF-IR standards labeled with a detectable substance and an unlabeled anti-IGF-IR antibody. In this assay, the biological sample, the labeled IGF-IR standards and the anti-IGF-IR antibody are combined and the amount of labeled IGF-IR standard bound to the unlabeled antibody is determined. The amount of IGF-IR in the biological sample is inversely proportional to the amount of labeled IGF-IR standard bound to the anti-IGF-IR antibody.

One may use the immunoassays disclosed above for a number of purposes. In one embodiment, the anti-IGF-IR antibodies may be used to detect IGF-IR in cells in cell culture. In a preferred embodiment, the anti-IGF-IR antibodies may be used to determine the level of tyrosine phosphorylation, tyrosine autophosphorylation of IGF-IR, and/or the amount of IGF-IR on the cell surface after treatment of the cells with various compounds. This method can be used to test compounds that may be used to activate or inhibit IGF-IR. In this method, one sample of cells is treated with a test compound for a period of time while another sample is left untreated. If tyrosine autophosphorylation is to be measured, the cells are lysed and tyrosine phosphorylation of the IGF-IR is measured using an immunoassay described above or as described in Example III, which uses an ELISA. If the total level of IGF-IR is to be measured, the cells are lysed and the total IGF-IR level is measured using one of the immunoassays described above.

A preferred immunoassay for determining IGF-IR tyrosine phosphorylation or for measuring total IGF-IR levels is an ELISA or Western blot. If only the cell surface level of IGF-IR is to be measured, the cells are not lysed, and the cell surface levels of IGF-IR are measured using one of the immunoassays described above. A preferred immunoassay for determining cell surface levels of IGF-IR includes the steps of labeling the cell surface proteins with a detectable label, such as biotin or $^{125}$I, immunoprecipitating the IGF-IR with an anti-IGF-IR antibody and then detecting the labeled IGF-IR. Another preferred immunoassay for determining the localization of IGF-IR, e.g., cell surface levels, is by using immunohistochemistry. Methods such as ELISA, RIA, Western blot, immunohistochemistry, cell surface labeling of integral membrane proteins and immunoprecipitation are well known in the art. See, e.g., Harlow and Lane, supra. In addition, the immunoassays may be scaled up for high throughput screening in order to test a large number of compounds for either activation or inhibition of IGF-IR.

The anti-IGF-IR antibodies of the invention may also be used to determine the levels of IGF-IR in a tissue or in cells derived from the tissue. In a preferred embodiment, the tissue is a diseased tissue. In a more preferred embodiment, the tissue is a tumor or a biopsy thereof. In a preferred embodiment of the method, a tissue or a biopsy thereof is excised from a patient. The tissue or biopsy is then used in an immunoassay to determine, e.g., IGF-IR levels, cell surface levels of IGF-IR, levels of tyrosine phosphorylation of IGF-IR, or localization of IGF-IR by the methods discussed above. The method can be used to determine if a tumor expresses IGF-IR at a high level.

The above-described diagnostic method can be used to determine whether a tumor expresses high levels of IGF-IR, which may be indicative that the tumor will respond well to treatment with anti-IGF-IR antibody. The diagnostic method may also be used to determine whether a tumor is potentially cancerous, if it expresses high levels of IGF-IR, or benign, if it expresses low levels of IGF-IR. Further, the diagnostic method may also be used to determine whether treatment with anti-IGF-IR antibody (see below) is causing a tumor to express lower levels of IGF-IR and/or to express lower levels of tyrosine autophosphorylation, and thus can be used to determine whether the treatment is successful. In general, a method to determine whether an anti-IGF-IR antibody decreases tyrosine phosphorylation comprises the steps of measuring the level of tyrosine phosphorylation in a cell or tissue of interest, incubating the cell or tissue with an anti-IGF-IR antibody or antigen-binding portion thereof, then re-measuring the level of tyrosine phosphorylation in the cell or tissue. The tyrosine phosphorylation of IGF-IR or of another protein(s) may be measured. The diagnostic method may also be used to determine whether a tissue or cell is not expressing high enough levels of IGF-IR or high enough levels of activated IGF-IR, which may be the case for individuals with dwarfism, osteoporosis or diabetes. A diagnosis that levels of IGF-IR or active IGF-IR are too low could be used for treatment with activating anti-IGF-IR antibodies, IGF-I or other therapeutic agents for increasing IGF-IR levels or activity.

The antibodies of the present invention may also be used in vivo to localize tissues and organs that express IGF-IR. In a preferred embodiment, the anti-IGF-IR antibodies can be used localize IGF-IR-expressing tumors. The advantage of the anti-IGF-IR antibodies of the present invention is that they will not generate an immune response upon administration. The method comprises the steps of administering an anti-IGF-IR antibody or a pharmaceutical composition thereof to a patient in need of such a diagnostic test and subjecting the patient to imaging analysis determine the location of the IGF-IR-expressing tissues. Imaging analysis is well known in the medical art, and includes, without limitation, x-ray analysis, magnetic resonance imaging (MRI) or computed tomography (CE). In another embodiment of the method, a biopsy is obtained from the patient to determine whether the tissue of interest expresses IGF-IR rather than subjecting the patient to imaging analysis. In a preferred embodiment, the anti-IGF-IR antibodies may be labeled with a detectable agent that can be imaged in a patient. For example, the antibody may be labeled with a contrast agent, such as barium, which can be used for x-ray analysis, or a magnetic contrast agent, such as a gadolinium chelate, which can be used for MRI or CE. Other labeling agents include, without limitation, radioisotopes, such as $^{99}$Tc. In another embodiment, the anti-IGF-IR antibody will be unlabeled and will be imaged by administering a second antibody or other molecule that is detectable and that can bind the anti-IGF-IR antibody.

Therapeutic Methods of Use

In another embodiment, the invention provides a method for inhibiting IGF-IR activity by administering an anti-IGF-IR antibody to a patient in need thereof. Any of the types of antibodies described herein may be used therapeutically. In a preferred embodiment, the anti-IGF-IR antibody is a human, chimeric or humanized antibody. In another preferred embodiment, the IGF-IR is human and the patient is a human patient. Alternatively, the patient may be a mammal that expresses an IGF-IR that the anti-IGF-IR antibody cross-reacts with. The antibody may be administered to a non-human mammal expressing an IGF-IR with which the antibody cross-reacts (i.e. a primate, or a cynomologous or rhesus monkey) for veterinary purposes or as an animal model of human disease. Such animal models may be useful for evaluating the therapeutic efficacy of antibodies of this invention.

As used herein, the term "a disorder in which IGF-IR activity is detrimental" is intended to include diseases and other disorders in which the presence of high levels of IGF-IR in a subject suffering from the disorder has been shown to be or is suspected of being either responsible for the pathophysiology of the disorder or a factor that contributes to a worsening of the disorder. Accordingly, a disorder in which high levels of IGF-IR activity is detrimental is a disorder in which inhibition of IGF-IR activity is expected to alleviate the symptoms and/or progression of the disorder. Such disorders may be evidenced, for example, by an increase in the levels of IGF-IR on the cell surface or in increased tyrosine autophosphorylation of IGF-IR in the affected cells or tissues of a subject suffering from the disorder. The increase in IGF-IR levels may be detected, for example, using an anti-IGF-IR antibody as described above.

In a preferred embodiment, an anti-IGF-IR antibody may be administered to a patient who has an IGF-IR-expressing tumor. A tumor may be a solid tumor or may be a non-solid tumor, such as a lymphoma. In a more preferred embodiment, an anti-IGF-IR antibody may be administered to a patient who has an IGF-IR-expressing tumor that is cancerous. In an even more preferred embodiment, the anti-IGF-IR antibody is administered to a patient who has a tumor of the lung, breast, prostate or colon. In a highly preferred embodiment, the method causes the tumor not to increase in weight or volume or to decrease in weight or volume. In another embodiment, the method causes the IGF-IR on the tumor to be internalized. In a preferred embodiment, the antibody is selected from 2.12.1, 2.13.2, 2.14.3, 3.1.1, 4.9.2, or 6.1.1, or comprises a heavy chain, light chain or antigen-binding region thereof.

In another preferred embodiment, an anti-IGF-IR antibody may be administered to a patient who expresses inappropriately high levels of IGF-I. It is known in the art that high-level expression of IGF-I can lead to a variety of common cancers. In a more preferred embodiment, the anti-IGF-IR antibody is administered to a patient with prostate cancer, glioma or fibrosarcoma. In an even more preferred embodiment, the method causes the cancer to stop proliferating abnormally, or not to increase in weight or volume or to decrease in weight or volume.

In one embodiment, said method relates to the treatment of cancer such as brain, squamous cell, bladder, gastric, pancreatic, breast, head, neck, esophageal, prostate, colorectal, lung, renal, kidney, ovarian, gynecological or thyroid cancer. Patients that can be treated with a compounds of the invention according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The antibody may be administered once, but more preferably is administered multiple times. The antibody may be administered from three times daily to once every six months. The administering may be on a schedule such as three times daily, twice daily, once daily, once every two days, once every three days, once weekly, once every two weeks, once every month, once every two months, once every three months and once every six months. The antibody may be administered via an oral, mucosal, buccal, intranasal, inhalable, intravenous, subcutaneous, intramuscular, parenteral, intratumor or topical route. The antibody may be administered at a site distant from the site of the tumor. The antibody may also be administered continuously via a minipump. The antibody may be administered once, at least twice or for at least the period of time until the condition is treated, palliated or cured. The antibody generally will be administered for as long as the tumor is present provided that the antibody causes the tumor or cancer to stop growing or to decrease in weight or volume. The antibody will generally be administered as part of a pharmaceutical composition as described supra. The dosage of antibody will generally be in the range of 0.1-100 mg/kg, more preferably 0.5-50 mg/kg, more preferably 1-20 mg/kg, and even more preferably 1-10 mg/kg. The serum concentration of the antibody may be measured by any method known in the art. See, e.g., Example XVII below. The antibody may also be administered prophylactically in order to prevent a cancer or tumor from occurring. This may be especially useful in patients that have a "high normal" level of IGF-I because these patients have been shown to have a higher risk of developing common cancers. See Rosen et al., supra.

In another aspect, the anti-IGF-IR antibody may be co-administered with other therapeutic agents, such as antineoplastic drugs or molecules, to a patient who has a hyperproliferative disorder, such as cancer or a tumor. In one aspect, the invention relates to a method for the treatment of the hyperproliferative disorder in a mammal comprising administering to said mammal a therapeutically effective amount of a compound of the invention in combination with an anti-tumor agent selected from the group consisting of, but not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens. In a more preferred embodiment, the antibody may be administered with an antineoplastic agent, such as adriamycin or taxol. In another preferred embodiment, the antibody or combination therapy is administered along with radiotherapy, chemotherapy, photodynamic therapy, surgery or other immunotherapy. In yet another preferred embodiment, the antibody will be administered with another antibody. For example, the anti-IGF-IR antibody may be administered with an antibody or other agent that is known to inhibit tumor or cancer cell proliferation, e.g., an antibody or agent that inhibits erbB2 receptor, EGF-R, CD20 or VEGF.

Co-administration of the antibody with an additional therapeutic agent (combination therapy) encompasses administering a pharmaceutical composition comprising the anti-IGF-IR antibody and the additional therapeutic agent and administering two or more separate pharmaceutical compositions, one comprising the anti-IGF-IR antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment of the disorder with the additional therapeutic agent. Similarly, administration of the anti-IGF-IR antibody may be administered prior to or subsequent to other therapy, such as radiotherapy, chemotherapy, photodynamic therapy, surgery or other immunotherapy The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months and once every six months, or may be administered continuously via a minipump. The combination therapy may be administered via an oral, mucosal, buccal, intranasal, inhalable, intravenous, subcutaneous, intramuscular, parenteral, intratumor or topical route. The combination therapy may be administered at a site distant from the site of the tumor. The combination therapy generally will be administered for as long as the tumor is present provided that the antibody causes the tumor or cancer to stop growing or to decrease in weight or volume.

In a still further embodiment, the anti-IGF-IR antibody is labeled with a radiolabel, an immunotoxin or a toxin, or is a fusion protein comprising a toxic peptide. The anti-IGF-IR antibody or anti-IGF-IR antibody fusion protein directs the radiolabel, immunotoxin, toxin or toxic peptide to the IGF-IR-expressing tumor or cancer cell. In a preferred embodiment, the radiolabel, immunotoxin, toxin or toxic peptide is internalized after the anti-IGF-IR antibody binds to the IGF-IR on the surface of the tumor or cancer cell.

In another aspect, the anti-IGF-IR antibody may be used therapeutically to induce apoptosis of specific cells in a patient in need thereof. In many cases, the cells targeted for apoptosis are cancerous or tumor cells. Thus, in a preferred embodiment, the invention provides a method of inducing apoptosis by administering a therapeutically effective amount of an anti-IGF-IR antibody to a patient in need thereof. In a preferred embodiment, the antibody is selected from 2.12.1, 2.13.2, 2.14.3, 3.1.1, 4.9.2, or 6.1.1, or comprises a heavy chain, light chain or antigen-binding region thereof.

In another aspect, the anti-IGF-IR antibody may be used to treat noncancerous states in which high levels of IGF-I and/or IGF-IR have been associated with the noncancerous state or disease. In one embodiment, the method comprises the step of administering an anti-IGF-IR antibody to a patient who has a noncancerous pathological state caused or exacerbated by high levels of IGF-I and/or IGF-IR levels or activity. In a preferred embodiment, the noncancerous pathological state is acromegaly, gigantism, psoriasis, atherosclerosis, smooth muscle restenosis of blood vessels or inappropriate microvascular proliferation, such as that found as a complication of diabetes, especially of the eye. In a more preferred embodiment, the anti-IGF-IR antibody slows the progress of the noncancerous pathological state. In a more preferred embodiment, the anti-IGF-IR antibody stops or reverses, at least in part, the noncancerous pathological state.

In another aspect, the invention provides a method of administering an activating anti-IGF-IR antibody to a patient in need thereof. In one embodiment, the activating antibody or pharmaceutical composition is administered to a patient in need thereof in an amount effective to increase IGF-IR activity. In a more preferred embodiment, the activating antibody is able to restore normal IGF-IR activity. In another preferred embodiment, the activating antibody may be administered to a patient who has small stature, neuropathy, a decrease in muscle mass or osteoporosis. In another preferred embodiment, the activating antibody may be administered with one or more other factors that increase cell proliferation, prevent apoptosis or increase IGF-IR activity. Such factors include growth factors such as IGF-I, and/or analogues of IGF-I that activate IGF-IR. In a preferred embodiment, the antibody is selected from 4.17.3, or comprises a heavy chain, light chain or antigen-binding portion thereof.

Gene Therapy

The nucleic acid molecules of the instant invention may be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into the chromosome of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids, or viral vectors, such as retroviruses, adenoviruses and adeno-associated viruses. After infection either in vivo or ex vivo, levels of antibody expression may be monitored by taking a sample from the treated patient and using any immunoassay known in the art and discussed herein.

In a preferred embodiment, the gene therapy method comprises the steps of administering an effective amount of an isolated nucleic acid molecule encoding the heavy chain or the antigen-binding portion thereof of the human antibody or portion thereof and expressing the nucleic acid molecule. In another embodiment, the gene therapy method comprises the steps of administering an effective amount of an isolated nucleic acid molecule encoding the light chain or the antigen-binding portion thereof of the human antibody or portion thereof and expressing the nucleic acid molecule. In a more preferred method, the gene therapy method comprises the steps of administering an effective amount of an isolated nucleic acid molecule encoding the heavy chain or the antigen-binding portion thereof of the human antibody or portion thereof and an effective amount of an isolated nucleic acid molecule encoding the light chain or the antigen-binding portion thereof of the human antibody or portion thereof and expressing the nucleic acid molecules. The gene therapy method may also comprise the step of administering another anti-cancer agent, such as taxol, tamoxifen, 5-FU, adriamycin or CP-358,774.

In order that this invention may be better understood, the following examples are set forth. These examples are for purposes of illustration only and are not to be construed as limiting the scope of the invention in any manner.

EXAMPLE I

Generation of Hybridomas Producing Anti-IGF-IR Antibody

Antibodies of the invention were prepared, selected, and assayed as follows:

Immunization and Hybridoma Generation

Eight to ten week old XENOMICE™ were immunized intraperitoneally or in their hind footpads with either the extracellular domain of human IGF-IR (10 μg/dose/mouse), or with 3T3-IGF-IR or 300.19-IGF-IR cells, which are two transfected cell lines that express human IGF-IR on their plasma membranes ($10 \times 10^6$ cells/dose/mouse). This dose was repeated five to seven times over a three to eight week period. Four days before fusion, the mice received a final injection of the extracellular domain of human IGF-IR in PBS. Spleen and lymph node lymphocytes from immunized mice were fused with the non-secretory myeloma P3-X63-Ag8.653 cell line and were subjected to HAT selection as previously described (Galfre and Milstein, *Methods Enzymol.* 73:3-46, 1981). A panel of hybridomas all secreting IGF-IR specific human IgG2a antibodies were recovered. Seven hybridomas producing monoclonal antibodies specific for IGF-IR were selected for further study and were designated 2.12.1, 2.13.2, 2.14.3, 3.1.1, 4.9.2, 4.17.3 and 6.1.1.

Hybridomas 2.12.1, 2.13.2, 2.14.3, 3.1.1, 4.9.2 and 4.17.3 were deposited in the American Type Culture Collection (ATCC), 10801 University Boulevard, Manassas, Va. 20110-2209, on Dec. 12, 2000 with the following deposit numbers:

| Hybridoma | Deposit No. |
|---|---|
| 2.12.1 | PTA-2792 |
| 2.13.2 | PTA-2788 |
| 2.14.3 | PTA-2790 |
| 3.1.1 | PTA-2791 |
| 4.9.2 | PTA-2789 |
| 4.17.3 | PTA-2793 |

EXAMPLE II

Determination of Affinity Constants ($K_d$) of Fully Human Anti-IGF-IR Monoclonal Antibodies by BIAcore We performed affinity measures of purified antibodies by surface plasmon resonance using the BIAcore 3000 instrument, following the manufacturer's protocols.

Protocol 1

To perform kinetic analyses, protein-A was immobilized on the sensorchip surfaces of the BIAcore. The sensorchip was then used to capture the anti-IGF-IR antibodies of the present invention. Different concentrations of the extracellular domain of IGF-IR were injected on the sensorchip and the binding and dissociation kinetics of the interactions between the anti-IGF-IR antibodies and the extracellular domain of IGF-IR were analyzed. The data were evaluated with global fit Langmuir 1:1, using baseline drift models available on the BIAevaluation software provided by BIAcore.

Protocol 2

BIAcore measurements were performed essentially as described by Fagerstam et al. "Detection of antigen-antibody interactions by surface plasmon resonance. Applications to epitope mapping." J. Mol. Recog. 3: 208-214. (1990).

Table I lists affinity measurements for representative anti-IGF-IR antibodies of the present invention:

TABLE I

| Monoclonal Antibody | $K_d$ (M) Protocol 1 | $K_d$ (M) Protocol 2 |
|---|---|---|
| 2.12.1 | $7.37 \times 10^{-9}$ | |
| 2.13.2 | $3.5 \times 10^{-9}$ | $1.53 \times 10^{-9}$ |
| 2.14.3 | $6.41 \times 10^{-10}$ | |
| 3.1.1 | $1.15 \times 10^{-9}$ | |
| 4.9.2 | $6.84 \times 10^{-10}$ | $4.27 \times 10^{-10}$ |
| 4.17.3 | $1.3 \times 10^{-8}$ | |
| 6.1.1 | $5.65 \times 10^{-10}$ | |

The kinetic analyses indicates that the antibodies prepared in accordance with the invention possess high affinities and strong binding constants for the extracellular domain of IGF-IR.

EXAMPLE III

Antibody-Mediated Inhibition of IGF-I-Induced Phosphorylation of IGF-IR

We performed ELISA experiments in order to determine whether the antibodies of this invention were able to block IGF-I-mediated activation of IGF-IR. IGF-I-mediated activation of IGF-IR was detected by increased receptor-associated tyrosine phosphorylation.

ELISA Plate Preparation

We prepared ELISA capture plates by adding 100 μl blocking buffer (3% bovine serum albumin [BSA] in Tris-buffered saline [TBS]) to each well of a ReactiBind Protein G-coated 96-well plates (Pierce) and incubated the plates with shaking for 30 minutes at room temperature. We diluted rabbit pan-specific SC-713 anti-IGF-IR antibody (Santa Cruz) in blocking buffer to a concentration of 5 μg/ml and added 100 μl diluted antibody to each well. We incubated the plates with shaking for 60-90 minutes at room temperature. We then washed the plates five times with wash buffer (TBS+0.1% Tween 20) and gently blotted the remaining buffer out onto paper towels. These plates were not allowed to dry out prior to the addition of lysate.

Preparation of Lysate from IGF-IR-Expressing Cells

We placed IGF-IR-transfected NIH-3T3 cells ($5 \times 10^4$/ml) in 100 μl of growth media (DMEM high glucose media supplemented with L-glutamine (0.29 mg/ml), 10% heat-inactivated FBS, and 500 μg/ml each of geneticin, penicillin and streptomycin) in 96-well U-bottom plates. We incubated the plates at 37° C., 5% $CO_2$ overnight to allow the cells to attach. We decanted the media from the plates and replaced it with 100 μl fresh growth media per well. For testing, we diluted the potential anti-IGF-IR antibodies to five times the desired final concentration in growth media and added 25 μl per well. All samples were performed in triplicate. We then incubated the plates at 37° C. for one hour. We stimulated the cells with 25 μl/well of 600 μg/ml IGF-1 (prepared in growth media) and incubate the plates at room temperature for 10 minutes. We then decanted the media by inverting the plates and blotting gently onto paper towels and lysed the adherent cells by adding 50 μl of lysis buffer (50 mM HEPES, pH 7.4, 10 mM EDTA, 150 mM NaCl, 1.5 mM $MgCl_2$, 1.6 mM $NaVO_4$, 1% Triton X-100, 1% glycerol supplemented immediately before use with one EDTA-free protease inhibitor tablet [Roche Molecular Sciences] per 50 ml) and shaking for 5 minutes at room temperature. We added 200 μl dilution buffer (50 mM HEPES, pH 7.4, 1.6 mM $NaVO_4$) to each well and mixed by pipetting up and down. We transferred 100 μl of lysate from each well to each well of the ELISA capture plate prepared as described above and incubated with gentle shaking for two hours at room temperature.

ELISA with Anti-Tyrosine-Phosphate (pTYR) Antibodies

We removed the cell lysate by inverting the plates, washed the plates five times with wash buffer and blotted on paper towels. We added 100 μl per well pTYR-specific antibody (HRP-PY54) diluted in blocking buffer to a concentration of 0.2 μg/ml and incubated the plates with shaking for 30 minutes at room temperature. We then washed these plates five times with wash buffer and blotted on paper towels.

We detected binding of the HRP-PY54 antibody by adding 100 μl per well of TMB peroxidase substrate solution (Kirkegaard & Perry) and incubating with shaking as the color developed (approximately 2-10 minutes). We stopped the color development reaction by adding 100 μl per well of TMB stop solution (Kirkegaard & Perry). We then shook the plates for 10 seconds at room temperature to mix the solution and quantitated by measurement at $OD_{450nm}$.

Figure 4:
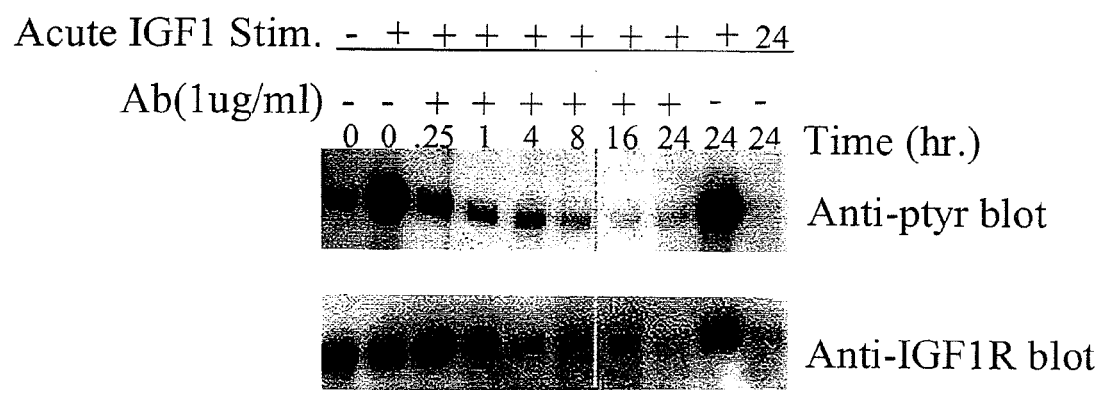
FIG. 4 shows that anti-IGF-IR antibody 4.9.2 inhibits IGF-I-induced receptor tyrosine phosphorylation (upper panel) and induces IGF-IR downregulation at the cell surface (lower panel).

Table II and FIG. 4 show the results of this experiment performed with several antibodies of the invention. The results of this experiment demonstrate the ability of the antibodies of this invention to block IGF-I-mediated activation of IGF-IR as shown by increased receptor-associated tyrosine phosphorylation. Furthermore, these results can be used to quantify the relative potency of the antibodies of this invention.

TABLE II

| Monoclonal Antibody | $IC_{50}$ (μg/ml) |
|---|---|
| 2.12.1 | 0.172 |
| 2.13.2 | 0.0812 |
| 2.14.3 | 0.325 |
| 4.9.2 | 0.0324 |

EXAMPLE IV

Antibody-Mediated Blocking of IGF-I/IGF-IR Binding antibodies of the invention to inhibit IGF-I binding to IGF-IR in a cell-based assay. We plated IGF-IR-transfected NIH-3T3 cells ($5 \times 10^4$/ml) in 100 μl of DMEM high glucose media supplemented with L-glutamine (0.29 mg/ml), 10% heat-inactivated FBS, and 500 μg/ml each of geneticin, penicillin and streptomycin in 96-well U-bottom plates. We then incubated the plates at 37° C., 5% $CO_2$ overnight to allow cells to attach. We then decanted the media from the plates and replaced it with 100 μl fresh media per well. For testing, we diluted antibodies in assay media (DMEM high glucose media supplemented with L-glutamine, 10% heat-inactivated FBS, 200 μg/ml BSA and 500 μg/ml each of geneticin, penicillin and streptomycin) to the desired final concentration and added 50 μl per well. All samples were performed in triplicate. We then incubated the plates at 37° C. for ten minutes. We diluted [$^{125}$I]-IGF-I to a concentration of 1 μCi/ml is assay media and added 50 μl per well of the plate. As a control for background radioactivity, we added cold IGF-I to a final concentration of 100 ng/ml. We incubated the plates for 10 minutes at 37° C., decanted the media by blotting gently onto paper towels and washed twice with assay media. We then lysed the cells by adding 50 μl 0.1 N NaOH, 0.1% SDS and shaking the plates for five minutes at room temperature. We then transferred the samples to a scintillation plate, added 150 μl OptiPhase Supermix and read the signal on a Wallac Micro-Beta counter.

Table III and FIG. 3 show the results of this experiment performed with three representative antibodies of the invention. This experiment demonstrated that antibodies of the invention specifically inhibit binding of [$^{125}$I]-IGF-I to cells overexpressing IGF-IR.

TABLE III

| Monoclonal Antibody | $IC_{50}$ |
|---|---|
| 2.12.1 | 0.45 μg/ml |
| 2.13.2 | 0.18 μg/ml |
| 4.9.2 | 0.1 μg/ml |

EXAMPLE V

Epitope Mapping Studies

Having demonstrated that the antibodies of the invention recognize IGF-IR, we performed epitope mapping studies with several antibodies of the invention. We focused these experiments particularly on the 2.12.1, 2.13.2, 2.14.3, and 4.9.2 antibodies.

We conducted BIAcore competition studies to determine whether the antibodies of this invention bind to the same or distinct site on the IGF-IR molecule. We bound the extracellular domain (ECD) of IGF-IR to a BIAcore sensorchip as described above in Example II. We bound a first antibody of the invention to this sensorchip-bound IGF-IR under saturating conditions. We then measured the ability of subsequent secondary antibodies of the invention to compete with the primary antibody for binding to IGF-IR. This technique enabled us to assign the antibodies of this invention to different binding groups.

We performed this experiment with antibodies 2.12.1, 2.13.2, 2.14.3, and 4.9.2. We observed that 2.13.2 and 4.9.2 compete for the same site on the extracellular domain of IGF-IR. The other antibodies, 2.12.1 and 2.14.3, bind to sites on IGF-IR that are different from both each other and from the site bound by 2.13.2 and 4.9.2.

EXAMPLE VI

Species Crossreactivity of the Antibodies of the Invention

In order to determine the species crossreactivity of the antibodies of the invention, we performed several experiments including immunoprecipitation, antibody-mediating blocking of IGF-I-induced receptor phosphorylation and FACS analysis.

To perform immunoprecipitation experiments, we plated cells in DMEM high glucose media supplemented with L-glutamine (0.29 mg/ml), 10% heat-inactivated FBS, and 500 µg/ml each of geneticin, penicillin and streptomycin to 50% confluence in T25 flasks. We then added 100 µl of an antibody of the invention in Hank's buffered saline solution (HBSS; Gibco BRL) at a concentration of 1 mg/ml. We incubated the plates for 30 minutes at 37° C. in an incubator and then stimulated the cells with IGF-I at 100 ng/ml for 10 minutes at room temperature. We lysed the cells in RIPA buffer (Harlow and Lane, supra) and immunoprecipitated IGF-IR with 2 µg of pan-specific SC-713 anti-IGF-IR antibody (Santa Cruz) plus protein A agarose beads for 1 hour at 4° C. We pelleted the beads and wash three times with PBS/T (PBS+0.1% Tween-20) and then boiled the beads in 40 µl Laemmli buffer containing 5% βME.

The samples prepared as described above were then analyzed by Western blot. We loaded 12 µl of each sample per lane on 4-10% gradient Novex™ gels run with 1×MES buffer (Novex™). Gels were run at 150V for 1 hour or at 200V for approximately 30 minutes. We then transferred the gel to a membrane in Novex™ transfer buffer with 10% methanol either overnight at 100 mA or for 1-1.5 hours at 250 mA. We then allowed the membrane to dry completely and blocked at room temperature with TBS (Tris-buffered saline pH 8.0) containing Superblock (Pierce Chemical Co.). We added the IGF-IR blotting antibody SC713 (Santa Cruz) to detect immunoprecipitated IGF-IR.

This experiment was performed with antibodies of the invention, particularly 2.12.1, 2.13.2, 4.17.3 and 4.9.2, on cells from a variety of animals. We found that antibodies 2.12.1, 2.13.2 and 4.9.2 were able to bind human, but not canine, guinea pig, rabbit or IGF-IR. Further, these antibodies were able to bind COS7 and Rhesus IGF-IR, both derived from old world monkeys, but not IGF-IR from the marmoset, which is a new world monkey. These experiments indicate that the antibodies are highly specific.

Antibody-Mediated Blocking of IGF-I/IGF-IR Binding in Non-Human Primates

Following our observation that the antibodies of the invention recognize IGF-IR from old world monkeys, we also tested their ability to block IGF-I/IGF-IR binding in cells derived from these old world monkeys. We plated cells in DMEM high glucose media supplemented with L-glutamine, 10% heat-inactivated FBS, and 500 µg/ml each of geneticin, penicillin and streptomycin to 50% confluence in T25 flasks. We then added an antibody of the invention, or media without antibody as a control, and stimulated the cells with IGF-I at 100 ng/ml for 10 minutes at room temperature. After stimulation, we lysed the cells and immunoprecipitated IGF-IR with pan-specific IGF-IR antibody SC713 as described above. We then performed Western blot analysis as described above using HRP-PY54 antibody to detect phosphorylated tyrosine in the activated IGF-IR.

We observed that antibodies of this invention, in particular 2.13.2 and 4.9.2 could block IGF-I-induced phosphorylation of IGF-IR in both COS7 and Rhesus cells. The $IC_{50}$ for the observed inhibition was 0.02 µg/ml and 0.005 µg/ml for COS7 and Rhesus IGF-IR, respectively.

Determination of Cross-species Affinity of Antibodies of the Invention

We performed FACS analysis to determine the affinity of the antibodies of the invention for IGF-IR from other animals, particularly the old world monkeys described above. We incubated aliquots of human and monkey cells ($5 \times 10^5$) for 1 hour on ice with increasing concentrations of biotinylated anti-IGF-IR antibodies of the invention or with a biotinylated anti-keyhole limpet hemocyanin (KLH) antibody (Abgenix) as a negative control. We then incubated the samples for 30 minutes on ice with steptavidin-conjugated RPE (phycoerythrin). We measured binding by flow cytometry and analyzed the histograms of fluorescence intensity (Fl2-H) versus cell number (Counts) using CellQuest software. We calculated binding ($K_d$) for each antibody from graphs of mean fluorescence intensity versus antibody concentration. In most experiments, we measured binding in cultured human MCF-7 cells and either rhesus or cynomologous tissue culture cells. We controlled for depletion of the antibody by measuring binding over a range of cell concentrations.

We performed the aforementioned FACS analysis to test the ability of antibodies of the invention, particularly 2.13.2 and 4.9.2, to bind human, rhesus and cynomologous cells. We observed a half maximal binding ($K_a$) of 0.1 µg/ml for all cell lines tested.

EXAMPLE VII

IGF-I Receptor Downregulation

We performed blocking experiments essentially as described above in Example IV up to the addition of [$^{125}$I]-labeled IGF-I. At this point, we boiled the cells in 40 µl Laemmli buffer containing 50% βme. We then analyzed the samples by western blot analysis as described above in Example VI and probed the blots with both pan-specific IGF-IR antibody SC713 to quantify the levels of IGF-IR and HRP-PY54 antibody to monitor the levels of phosphorylated tyrosine in the activated IGF-IR.

As observed previously (Example III), we observed blockage of IGF-1-induced phosphorylation of IGF-IR following the treatment of cells with an antibody of this invention (FIG. 4). Further, we observed that this blockage of IGF-I-induced phosphorylation was followed by downregulation of the IGF-IR in these cells. See, e.g., FIG. 4. IGF-IR levels were maximally reduced 16 hours after stimulation with IGF-I in the presence of an antibody of the invention.

EXAMPLE VIII

Effects of the Antibodies of the Invention on IGF-IR In Vivo

We determined whether the effects of the antibodies of the invention on IGF-IR as described in the previous examples would occur in vivo. We induced tumors in athymic mice according to published methods (V. A. Pollack et al., "Inhibition of epidermal growth factor receptor-associated tyrosine phosphorylation in human carcinomas with CP-358,774: Dynamics of receptor inhibition in situ and antitumor effects in athymic mice," *J. Pharmacol. Exp. Ther.* 291:739-748 (1999). Briefly, we injected IGF-IR-transfected NIH-3T3 cells ($5 \times 10^6$) subcutaneously into 3-4 week-old athymic (nu/nu) mice with 0.2 ml of Matrigel preparation. We then injected mice with an antibody of the invention intraperitoneally after established (i.e. approximately 400 mm$^3$) tumors formed.

After 24 hours, we extracted the tumors, homogenized them and determined the level of IGF-IR. To determine IGF-IR levels, we diluted the SC-713 antibody in Blocking buffer to a final concentration of μg/ml and added 100 μl to each well of a Reacti-Bind Goat anti-rabbit (GAR) coated plate (Pierce). We incubated the plates at room temperature for 1 hour with shaking and then washed the plates five times with wash buffer. We then weighed tumor samples that had been prepared as described above and homogenized them in lysis buffer (1 ml/100 mg). We diluted 12.5 μl of tumor extract with lysis buffer to a final volume of 100 μl and added this to each well of a 96-well plate. We incubated the plates at room temperature with shaking for 1-2 hours and then washed the plates five times with Wash buffer. We then added 100 μl HRP-PY54 or biotinylated anti-IGF-IR antibody in Blocking buffer to each well and incubated at room temperature with shaking for 30 minutes. We then washed the plates five times with wash buffer and developed the plates. We developed the plates probed with HRP-PY54 by adding 100 μl of the TMB microwell substrate per well and stopped color development with the addition 100 μl 0.9 M H$_2$SO$_4$. We then quantitated the signal by shaking for 10 seconds and measuring OD$_{450nm}$. The signal was normalized to total protein. We developed plates probed with anti-IGF-IR antibody by adding 100 μl of streptavidin-HRP diluted in Blocking buffer to each well, incubating at room temperature with shaking for 30 minutes and then continuing as described for HRP-PY54.

Figure 5:
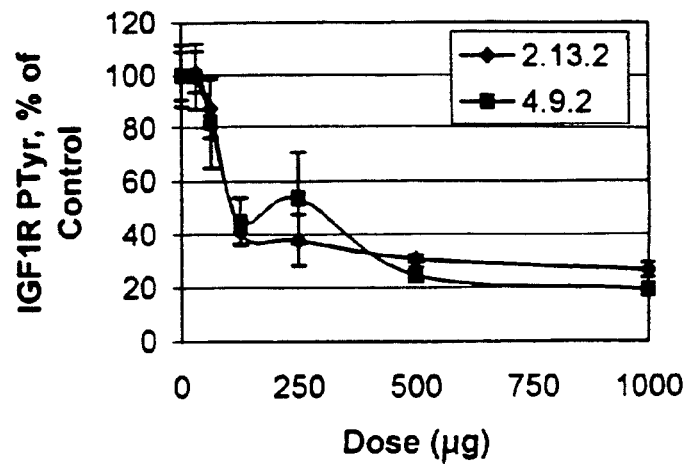
FIG. 5 shows that anti-IGF-IR antibodies 2.13.2 and 4.9.2 reduce IGF-IR phosphotyrosine signal in 3T3-IGF-IR tumors.
Figure 6:
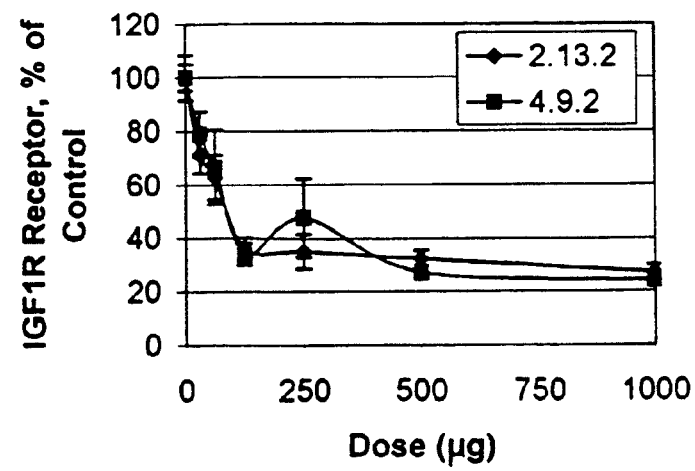
FIG. 6 shows that anti-IGF-IR antibodies 2.13.2 and 4.9.2 reduce IGF-IR in 3T3-IGF-IR tumors.

We observed that intraperitoneal injection of an antibody of this invention, particularly 2.13.2 and 4.9.2, resulted in inhibition of IGF-IR activity as measured by a decrease of both IGF-IR phosphotyrosine (phosphorylated IGF-IR) and total IGF-IR protein (FIG. 6). In addition, we also observed a decrease in IGF-IR phosphotyrosine (phosphorylated IGF-IR) (FIG. 5). Without wishing to be bound by any theory, the decreased levels of IGF-IR phosphotyrosine may be due to the decreased levels of IGF-IR protein in vivo after treatment with the antibody or may be due to a combination of decreased levels of IGF-IR protein and a decrease in tyrosine phosphorylation on the IGF-IR that is present due to blocking of activation by ligand (e.g., IGF-I or IGF-II). Furthermore, this inhibition was responsive to the dose of antibody injected (FIG. 6). These data demonstrate that the antibodies of the invention are able to target the IGF-IR in vivo in a manner analogous to what we observed in vitro.

EXAMPLE IX

Growth Inhibition (TGI) of 3T3/IGF-IR Cell Tumors

We tested whether anti-IGF-IR antibodies of the invention would function to inhibit tumor growth. We induced tumors as described above (Example VIII) and when established, palpable tumors formed (i.e. 250 mm$^3$, within 6-9 days), we treated the mice with a single, 0.20 ml dose of antibody by intraperitoneal injection. We measured tumor size by Vernier calipers across two diameters every third day and calculated the volume using the formula (length×[width]$^2$)/2 using methods established by Geran, et al., "Protocols for screening chemical agents and natural products against animal tumors and other biological systems," *Cancer Chemother. Rep.* 3:1-104.

Figure 7:
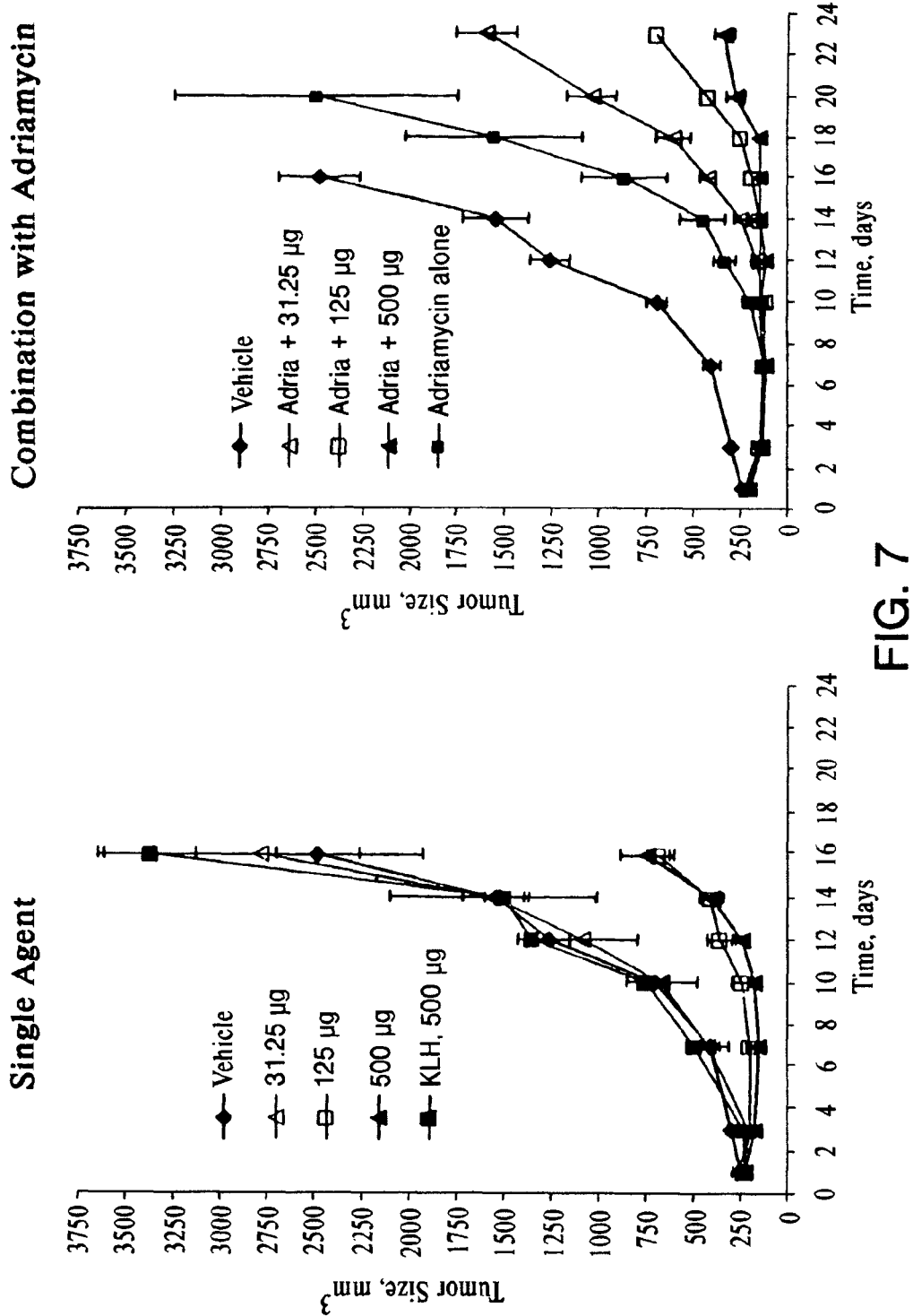
FIG. 7 shows that anti-IGF-IR antibody 2.13.2 inhibits 3T3-IGF-IR tumor growth in vivo alone (left panel) or in combination with adriamycin (right panel).

When we performed this analysis with an antibody of the invention, we found that a single treatment with antibody 2.13.2 alone inhibited the growth of IGF-IR-transfected NIH-3T3 cell-induced tumors (FIG. 7, left panel). Furthermore, in combination studies with a single dose of 7.5 mg/kg intravenously-supplied adriamycin, we observed that administration of a single dose of 2.13.2 enhanced the effectiveness of adriamycin, a known inhibitor of tumor growth. The combination of adriamycin with an antibody of the invention, 2.13.2, demonstrated a growth delay of 7 days versus treatment with the antibody or adriamycin alone (FIG. 7, right panel).

EXAMPLE X

Relationship of Antibody Levels to IGF-IR Downregulation

Figure 8:
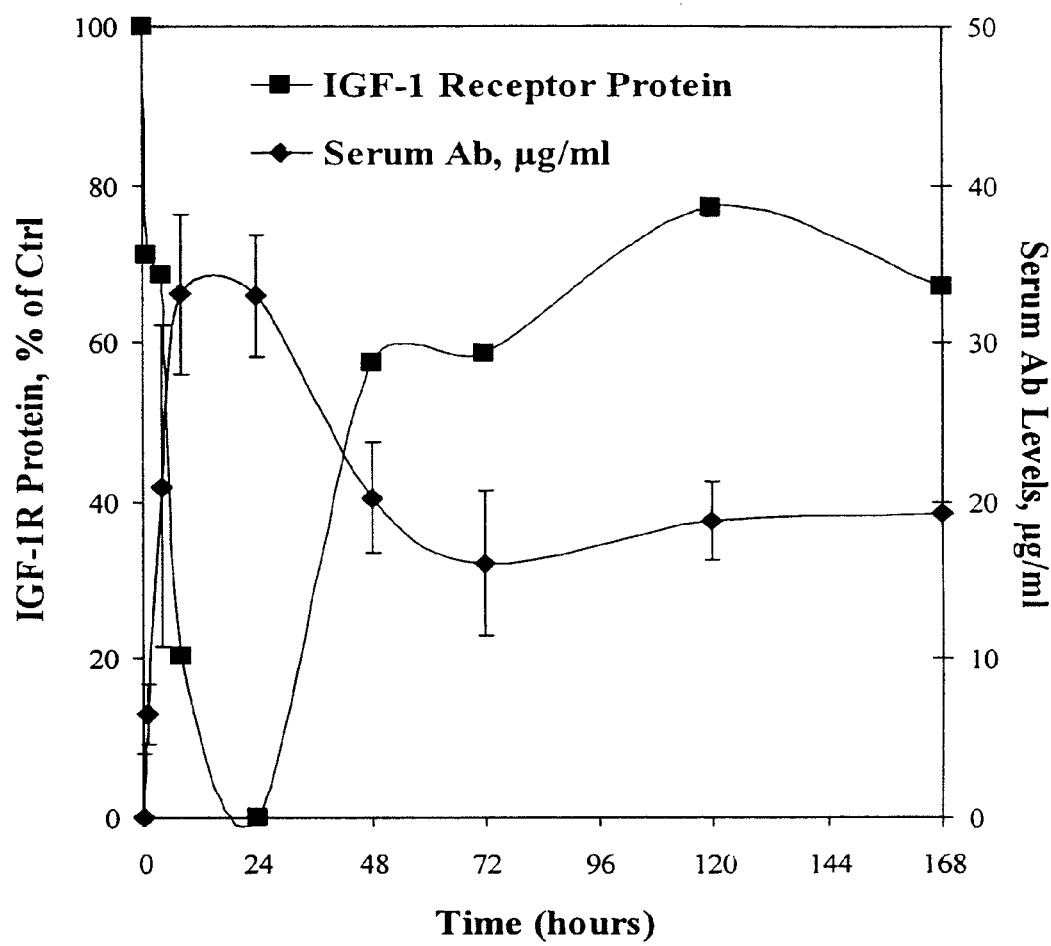
FIG. 8 shows the relationship between anti-IGF-IR antibody 2.13.2 serum levels and IGF-IR downregulation in 3T3-IGF-IR tumors.

Tumors were induced in nude mice as described in Example VIII. The mice were then treated with 125 μg of 2.13.2 by intraperitoneal injuction, as described in Example VIII. Tumors were extracted and IGF-IR levels were measured by ELISA as described in Example VIII. FIG. 8 shows the serum 2.13.2 antibody levels and IGF-IR receptor levels over time. The experiment demonstrates that the IGF-IR is down-regulated by the antibody and that the degree of IGF-IR inhibition is dose proportional to the serum concentration of the antibody.

EXAMPLE XI

Figure 9:
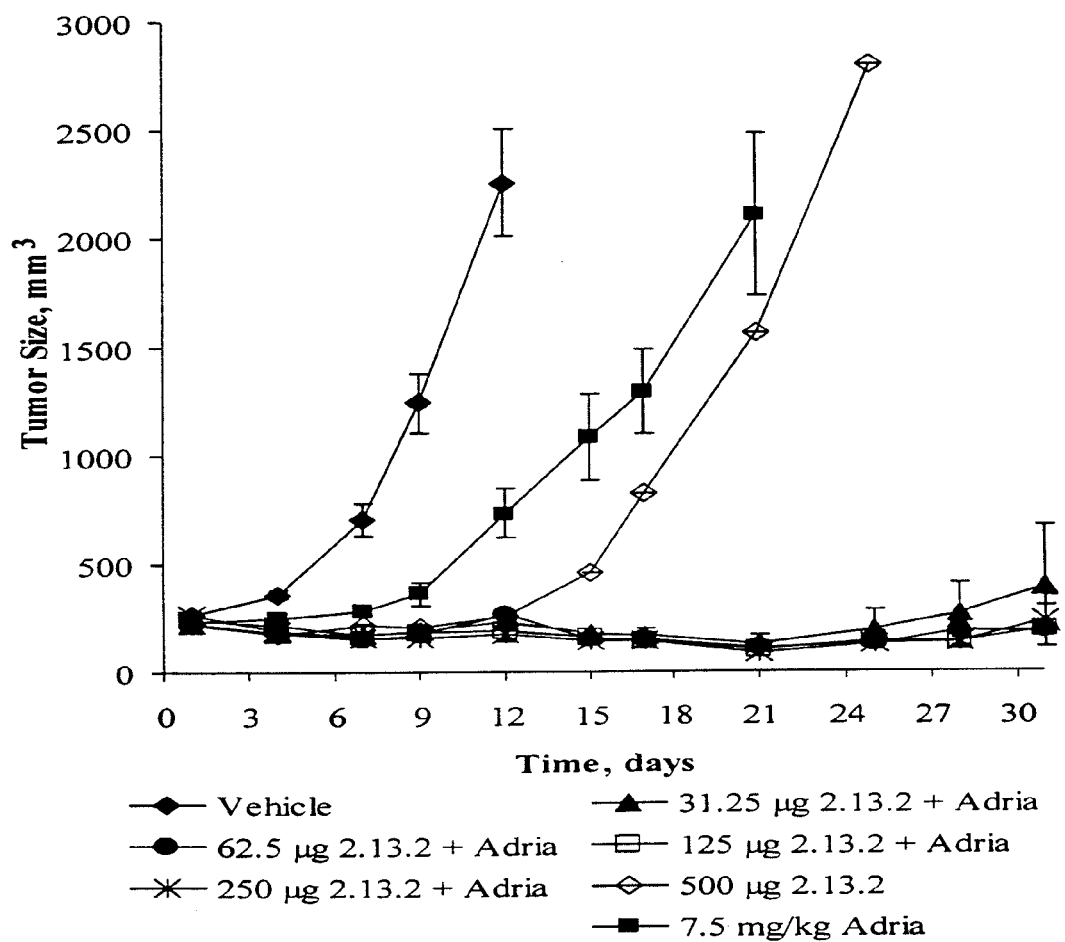
FIG. 9 shows that multiple doses of anti-IGF-IR antibody 2.13.2 inhibit 3T3-IGF-IR tumor growth in vivo alone or in combination with adriamycin.

Growth Inhibition of 3T3/IGF-IR Tumors with Multiple Dosing of Antibody in Combination with Adriamycin Tumors were induced in nude mice as described in Example IX. Mice with established subcutaneous tumors of approximately 250 mm$^3$ were treated on days 1, 8, 15 and 22 with various amounts of 2.13.2 antibody (i.p.) or 7.5 mg/kg adriamycin (i.v.), either as single agents or in combination, as described in Example IX. FIG. 9 shows the tumor size in relation to the various treatments over time. The experiment demonstrates that treatment with an anti-IGF-IR antibody given once every seven days inhibits tumor cell growth and enhances inhibition of tumor cell growth in combination with adriamycin, a known tumor inhibitor.

EXAMPLE XII

Growth Inhibition of Large Tumors

Figure 10:
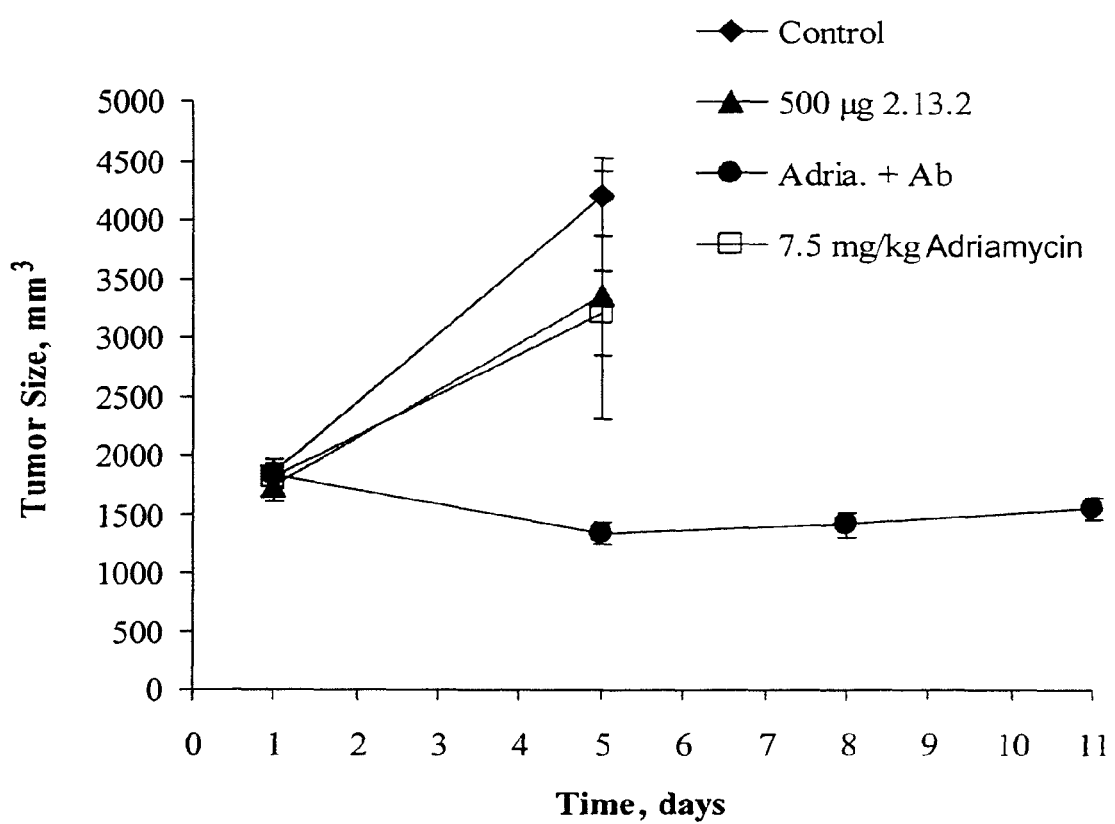
FIG. 10 shows that anti-IGF-IR antibody 2.13.2 inhibits large tumor growth in vivo in combination with adriamycin.

Tumors were induced in nude mice as described in Example IX. Mice with large established subcutaneous tumors of slightly less than 2000 mm$^3$ were treated on days 1 and 8 with various amounts of 2.13.2 antibody (i.p.) or 7.5 mg/kg adriamycin (i.v.), either as single agents or in combination, as described in Example IX. FIG. 10 shows the tumor size in relation to the various treatments over time. Control, antibody alone and adriamycin alone animal groups were terminated at day 5, when the tumor size exceeded 2000 mm$^3$. The experiment demonstrates that treatment with an anti-IGF-IR antibody in combination with adriamycin is highly efficacious against large tumors when multiple doses are given.

EXAMPLE XIII

Growth Inhibition of Colorectal Cell Tumors

Figure 12:
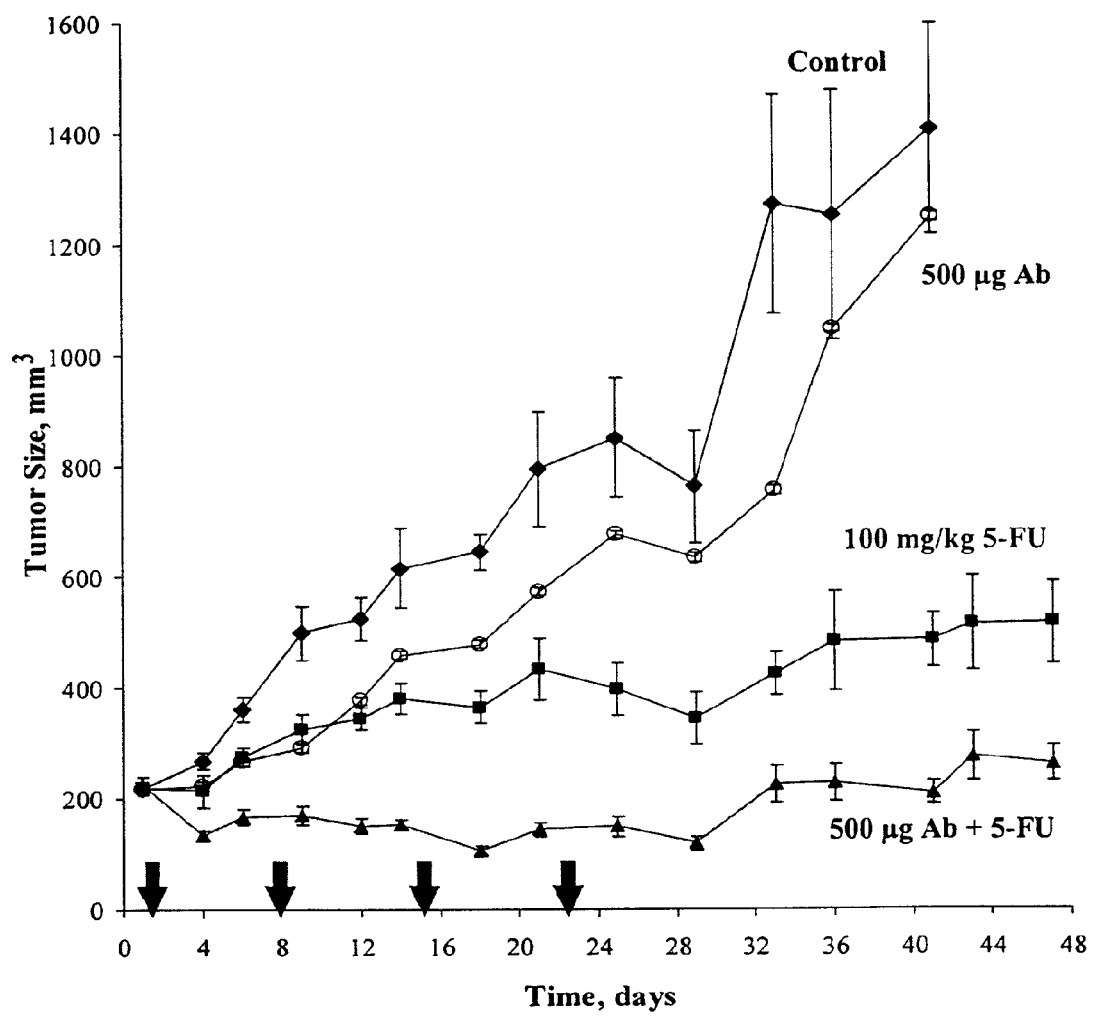
FIG. 12 shows that multiple doses of anti-IGF-IR antibody 2.13.2 inhibit Colo 205 tumor growth in vivo alone or in combination with 5-FU.

Tumors were induced in nude mice as described in Example IX except that Colo 205 cells (ATCC CCL 222) were used. Colo 205 cells are human colorectal adenocarcinoma cells. Mice with established subcutaneous tumors of approximately 250 mm$^3$ were treated with various amounts of 2.13.2 antibody (i.p.) or with 100 mg/kg 5-fluorodeoxyuridine (5-FU, i.v.), either as single agents or in combination, as described in Example IX. FIG. 11 shows the tumor size in relation to the various treatments over time. The experiment demonstrates that treatment with an anti-IGF-IR antibody given once inhibits human colorectal cancer cell growth when provided as a single agent and enhances the effectiveness of 5-FU, a known tumor inhibitor. Mice with established Colo 205 tumors were treated on days 1, 8, 15 and 22 with 500 μg 2.13.2 (i.p.), 100 mg/kg 5-FU (i.v.) or a combination thereof. FIG. 12 shows the tumor size in relation to the various treatments over time. The experiment demonstrates that treatment with an anti-IGF-IR antibody given once every seven days inhibits human colorectal cancer cell growth and enhances the effectiveness of 5-FU.

EXAMPLE XIV

Growth Inhibition of Breast Cancer Cell Tumors

Figure 13:
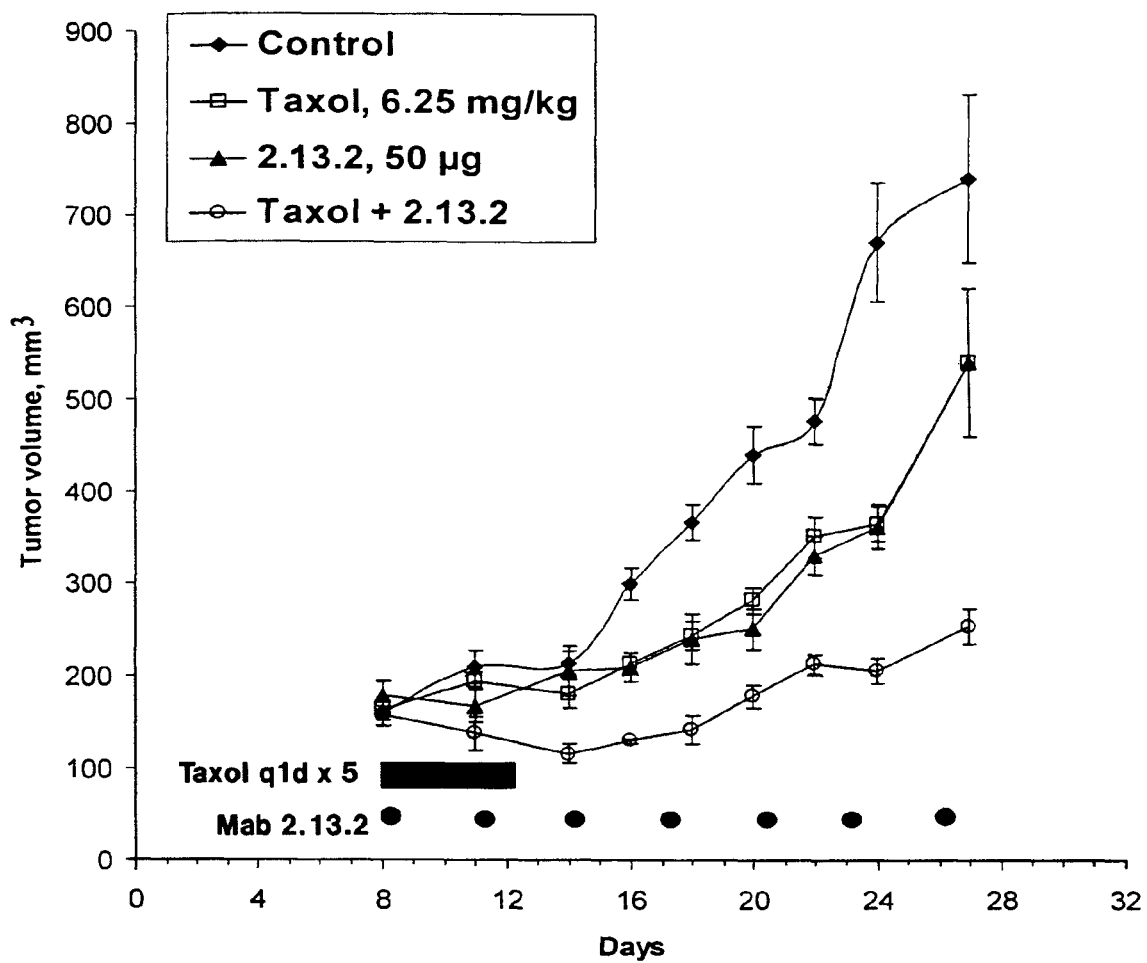
FIG. 13 shows that multiple doses of anti-IGF-IR antibody 2.13.2 inhibit MCF-7 tumor growth in vivo alone or in combination with taxol.

Nude mice as described in Example VIII were implanted with biodegradable estrogen pellets (0.72 mg 17-∃-estradiol/pellet, 60 day release; Innovative Research of America). After 48 hours, tumors were induced in nude mice essentially as described in Example IX except that MCF-7 cells (ATCC HTB-22) were used. MCF-7 cells are estrogen-dependent human breast carcinoma cells. Mice with established subcutaneous tumors of approximately 250 mm$^3$ were treated with 50:g 2.13.2 antibody (i.p.) on days 1, 4, 7, 10, 13, 16, 19 and 22 (q3dx7) or with 6.25 mg/kg taxol (i.p.) on days 1, 2, 3, 4, 5 (q1dx5), either as single agents or in combination, essentially as described in Example IX. FIG. 13 shows the tumor size in relation to the various treatments over time. The experiment demonstrates that treatment with an anti-IGF-IR antibody by itself inhibits human breast cancer cell growth when administered once every three days and also enhances the effectiveness of taxol, a known breast cancer inhibitor, when given in combination.

Figure 14:
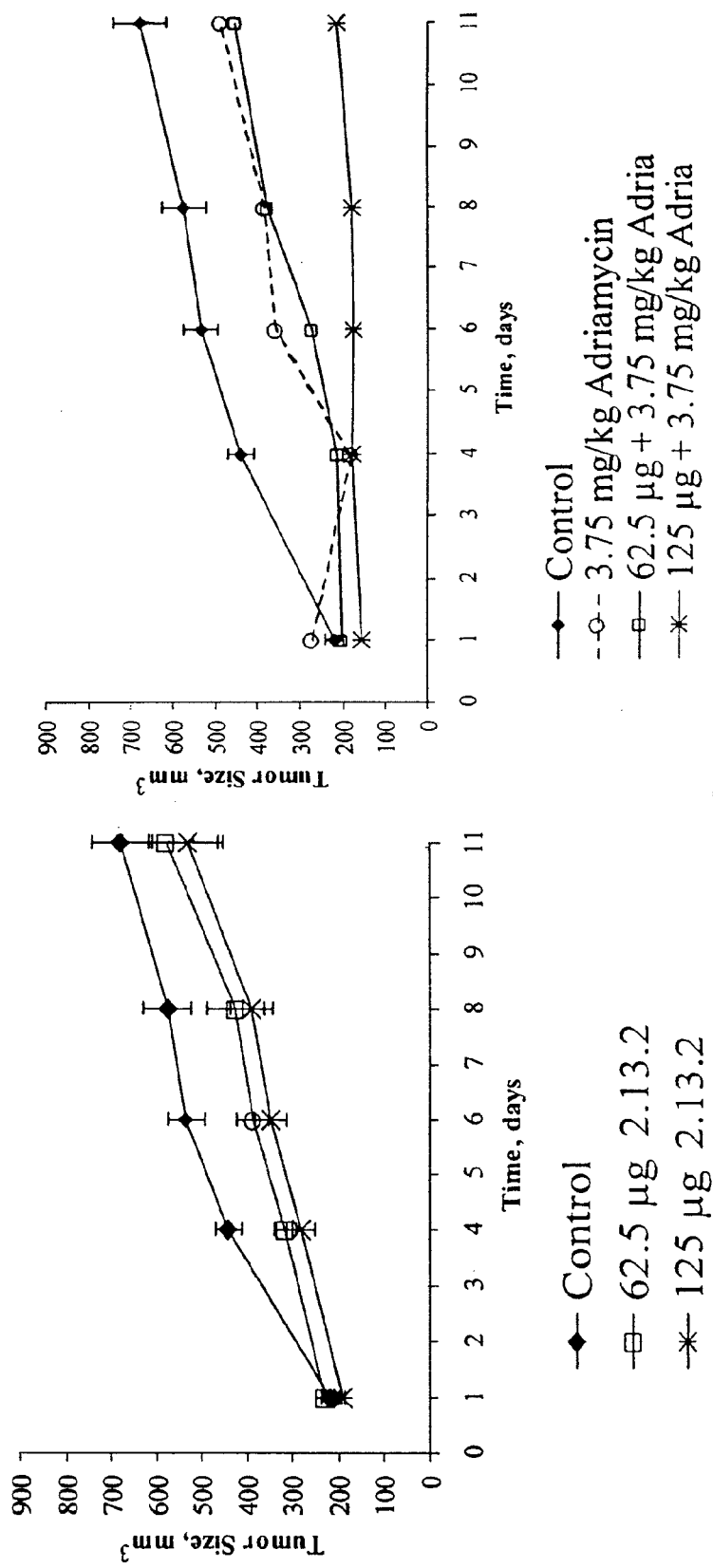
FIG. 14 shows that anti-IGF-IR antibody 2.13.2 inhibits MCF-7 tumor growth in vivo alone (left panel) or in combination with adriamycin (right panel).

Mice having established tumors from MCF-7 cells as described immediately above were treated on day 1 with various amounts of 2.13.2 antibody (i.p.) alone or with 3.75 mg/kg adriamycin (i.v.), essentially as described in Example IX. FIG. 14 shows the tumor size in relation to the various treatments over time. The experiment demonstrates that a single treatment with an anti-IGF-IR antibody by itself inhibits human breast cancer cell growth and enhances the effectiveness of adriamycin, a known tumor inhibitor.

Figure 15:
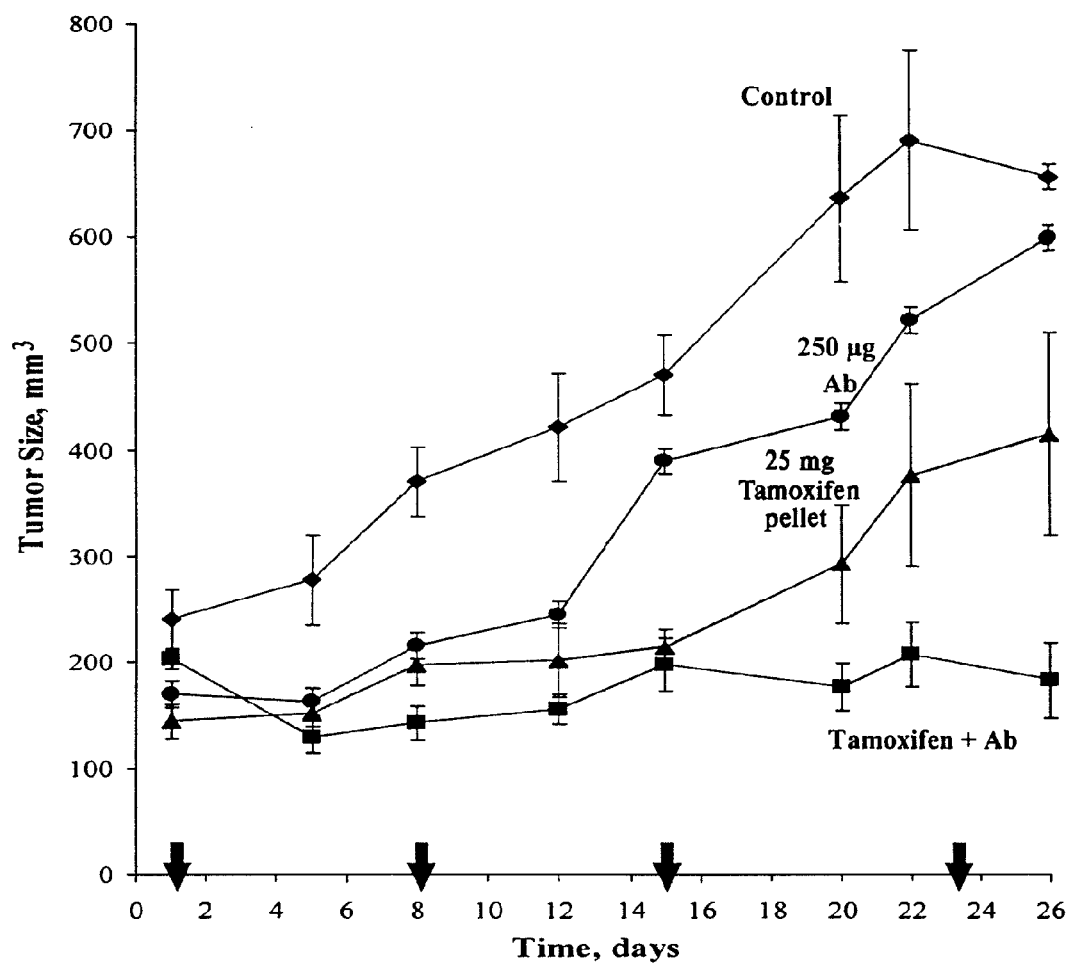
FIG. 15 shows that multiple doses of anti-IGF-IR antibody 2.13.2 inhibit MCF-7 tumor growth in vivo alone or in combination with tamoxifen.

Mice having established tumors from MCF-7 cells as described immediately above were treated with 250:g 2.13.2 antibody (i.p.) on days 1, 8, 15 and 23 or with a biodegradable tamoxifen pellet (25 mg/pellet, free base, 60 day release, Innovative Research of America), either as single agents or in combination, essentially as described in Example IX. The tamoxifen pellet was implanted on day 1 after the tumor was established. FIG. 15 shows the tumor size in relation to the various treatments over time. The experiment demonstrates that treatment with an anti-IGF-IR antibody administered once every seven days inhibits human breast cancer growth by itself and enhances the effectiveness of tamoxifen, a known tumor inhibitor.

EXAMPLE XVI

Growth Inhibition of Epidermoid Carcinoma Cell Tumors

Figure 16:
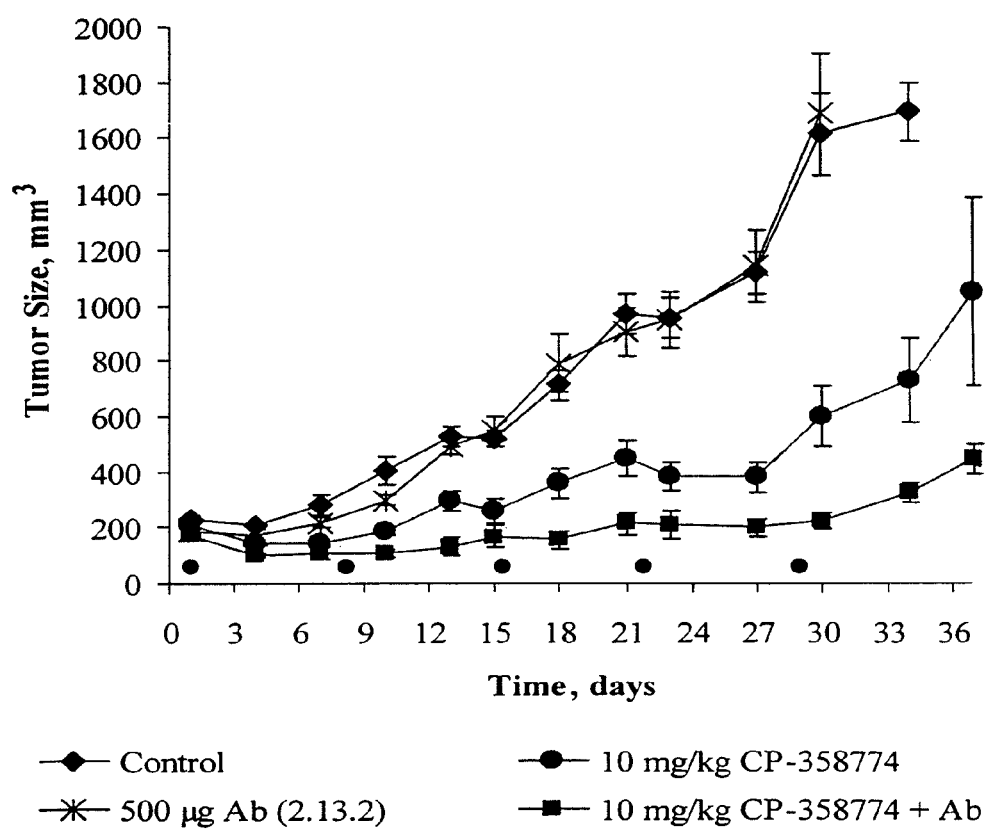
FIG. 16 shows that multiple doses of anti-IGF-IR antibody 2.13.2 inhibit A431 tumor growth in vivo alone or in combination with the epidermal growth factor receptor (EGF-R) tyrosine kinase inhibitor CP-358,774.

Tumors were induced in nude mice essentially as described in Example IX except that A431 cells (ATCC CRL 1555) were used. A431 cells are human epidermoid carcinoma cells that overexpress EGFR. Mice with established subcutaneous tumors of approximately 250 mm$^3$ were treated on days 1, 8, 15, 22 and 29 with 500:g 2.13.2 antibody (i.p.) or were treated once daily for 27 days with 10 mg/kg CP-358,774 given orally (p.o.), either as single agents or in combination, as described in Example IX. CP-358,774 is described in U.S. Pat. No. 5,747,498 and Moyer et al., Cancer Research 57: 4838-4848 (1997), herein incorporated by reference. FIG. 16 shows the tumor size in relation to the various treatments over time. The experiment demonstrates that treatment with an anti-IGF-IR antibody enhances the effectiveness of CP-358,774, a known EGF-R tyrosine kinase inhibitor, for inhibiting the growth of a human epidermoid carcinoma tumor.

EXAMPLE XVII

Pharmacokinetics of Anti-IGF-IR Antibodies in vivo

Figure 17:
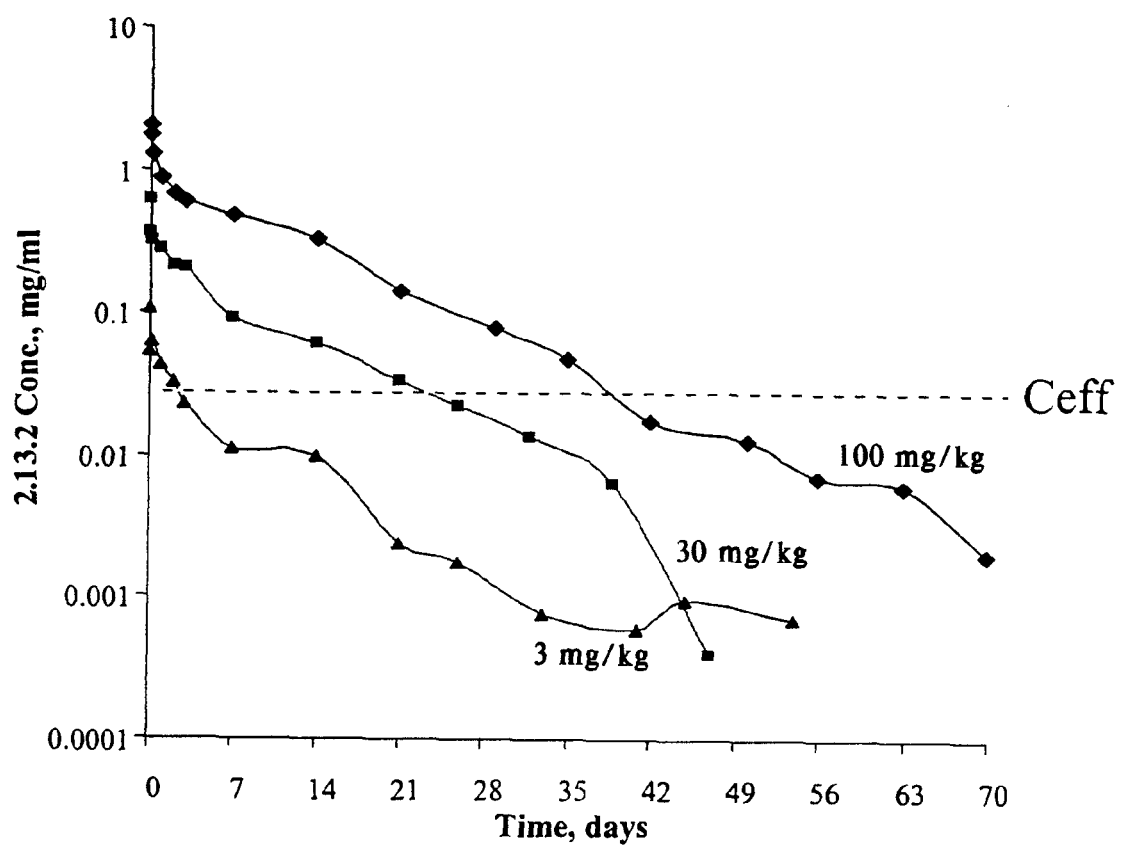
FIG. 17 shows a pharmacokinetic evaluation of a single intravenous injection of anti-IGF-IR antibody 2.13.2 in Cynomologus monkeys.

To evaluate the pharmacokinetics of the anti-IGF-IR antibodies, cynomolgus monkeys were injected intravenously with 3, 30 or 100 mg/kg of 2.13.2 antibody in an acetate buffer. Serum was collected from the monkeys at various time points and anti-IGF-IR antibody concentrations in the monkeys were determined for a period of up to ten weeks levels. To quantitate functional serum antibody levels, the extracellular domain of the human IGF-IR (IGF-I-sR, R&D Systems, Catalog #391GR) was bound to 96-well plates. Monkey serum (diluted between 1:100 and 1:15,000) was added to the assay plates so that each sample would be within the linear range of the standard curve and incubated under conditions in which any anti-IGF-IR antibody would bind to IGF-I-sR. After washing the plates, a labeled anti-human IgG antibody was added to the plates and incubated under conditions in which the anti-human IgG antibody would bind to the anti-IGF-IR antibody. The plates were then washed and developed, and a control standard curve and linear regression fits used to quantitate the amount of anti-IGF-IR antibodies. FIG. 17 shows the concentration of 2.13.2 in serum over time. The experiment demonstrates that the half-life of the anti-IGF-IR antibody is 4.6 to 7.7 days and has a volume distribution of 74-105 mL/kg. Further, the experiment demonstrates that the amounts given are dose-proportional in the monkey, which indicates that the anti-IGF-IR antibody has saturated any available IGF-IR binding sites in the body even at the lowest dose of 3 mg/kg.

EXAMPLE XVIII

Figure 18:
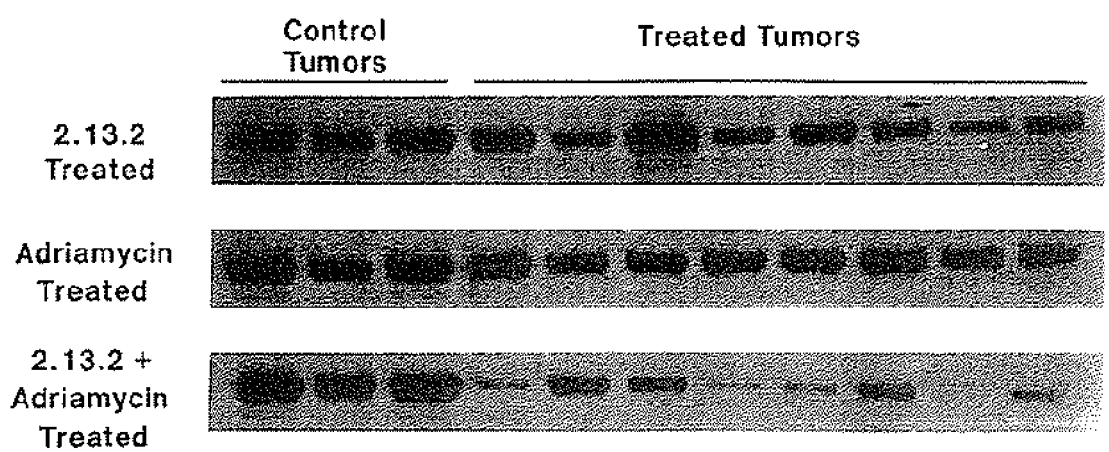
FIG. 18 shows that the combination of anti-IGF-IR antibody 2.13.2 and adriamycin increases the downregulation of IGF-IR on 3T3-IGF-IR tumors in vivo.

Combination Therapy of Anti-IGF-IR Antibody and Adriamycin Downregulates IGF-IR In Vivo Tumors were induced in nude mice as described in Example IX. Mice with established subcutaneous tumors of approximately 400 mm³ were treated with a single injection of 250:g 2.13.2 antibody (i.p.) or with 7.5 mg/kg adriamycin (i.v.), either as single agents or in combination, as described in Example IX. 72 hours after administration of the agents, tumors were extracted as described in Example VIII, and equal amounts of the tumor extracts were subjected to sodium dodecyl phosphate polyacrylamide gel electrophoresis (SDS PAGE) and western blot analysis using the anti-IGF-IR antibody SC-713 (Santa Cruz). FIG. 18 shows the amounts of IGF-IR in tumor cells in control animals (first three lanes of each panel), in animals treated with antibody alone (top panel), in animals treated with adriamycin alone (middle panel) and in animals treated with antibody and adriamycin (lower panel). Each lane represents equal amounts of protein from individual tumors from individual mice. The experiment demonstrates that treatment with adriamycin alone has little effect on IGF-IR levels and that treatment with antibody alone shows some decrease in IGF-IR levels. Surprisingly, treatment with adriamycin and antibody together shows a dramatic decrease in IGF-IR levels, demonstrating that adriamycin and antibody greatly downregulate IGF-IR levels.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Applicants also incorporate by reference herein the document "0006590032106.txt," which was created on Dec. 17, 2013 and has a size of 65,861 bytes, and which is electronically submitted concurrently with this application.

We claim:

1. A method of treating cancer cells in a patient in need thereof, wherein said cancer cells express IGF-I or IGF-IR, comprising:
   providing a monoclonal antibody, or an antigen-binding portion thereof, that specifically binds to human insulin-like growth factor I receptor (IGF-IR) and comprises a heavy chain CDR1, CDR2, and CDR3 amino acid sequence of antibody 4.9.2 and a light chain CDR1, CDR2, and CDR3 amino acid sequence of antibody 4.9.2, and wherein antibody 4.9.2 is the antibody produced by the hybridoma deposited under ATCC Accession Number PTA-2789; and
   administering a pharmaceutical composition comprising the monoclonal antibody or antigen-binding portion thereof to the patient.

2. The method of treating cancer according to claim 1, wherein the monoclonal antibody or antigen-binding portion thereof comprises a CDR1, CDR2, or CDR3 amino acid sequence within the heavy chain sequence of SEQ ID NO: 16.

3. The method of treating cancer according to claim 1, wherein the monoclonal antibody or antigen-binding portion thereof comprises a CDR1, CDR2, and CDR3 amino acid sequence within the light chain sequence of SEQ ID NO: 14.

4. The method of treating cancer according to claim 1, wherein the monoclonal antibody or antigen-binding portion thereof comprises a variable domain of the heavy chain amino acid sequence of SEQ ID NO: 16.

5. The method of treating cancer according to claim 1, wherein the monoclonal antibody or antigen-binding portion thereof comprises a variable domain of the light chain amino acid sequence of SEQ ID NO: 14.

6. The method of treating cancer according to claim 1, wherein the monoclonal antibody or antigen-binding portion thereof has an isotype selected from the group consisting of: an immunoglobulin G (IgG), an IgM, an IgE, an IgA, or an IgD isotype.

7. The method of treating cancer according to claim 1, wherein the monoclonal antibody or antigen-binding portion thereof is selected from the group consisting of: a Fab fragment, an F(ab')$_2$ fragment, and an Fv fragment.

8. The method of treating cancer cells according to claim 1, wherein the cancer cells are selected from the group consisting of colorectal cancer, breast cancer, and squamous cell cancer cells.

9. The method of treating cancer according to claim 1, further comprising administering an anti-neoplastic, anti-tumor, anti-angiogenic, or chemotherapeutic agent to the patient.

10. The method of treating cancer cells according to claim 1, wherein said cancer cells overexpresses IGF-I or IGF-IR.

11. A method of treating a tumor expressing IGF-I or IGF-IR in a patient, comprising:
    providing a monoclonal antibody, or an antigen-binding portion thereof, that specifically binds to human insulin-like growth factor I receptor (IGF-IR) and comprises a heavy chain CDR1, CDR2, and CDR3 amino acid sequence of antibody 4.9.2 and a light chain CDR1, CDR2, and CDR3 amino acid sequence of antibody 4.9.2, and wherein antibody 4.9.2 is the antibody produced by the hybridoma deposited under ATCC Accession Number PTA-2789; and
    administering a pharmaceutical composition comprising the monoclonal antibody or antigen-binding portion thereof to the patient.

12. The method of treating a tumor according to claim 11, wherein the monoclonal antibody or antigen-binding portion thereof comprises a CDR1, CDR2, or CDR3 amino acid sequence within the heavy chain sequence of SEQ ID NO: 16.

13. The method of treating a tumor according to claim 11, wherein the monoclonal antibody or antigen-binding portion thereof comprises a CDR1, CDR2, and CDR3 amino acid sequence within the light chain sequence of SEQ ID NO: 14.

14. The method of treating a tumor according to claim 11, wherein the monoclonal antibody or antigen-binding portion thereof comprises a variable domain of the heavy chain amino acid sequence of SEQ ID NO: 16.

15. The method of treating a tumor according to claim 11, wherein the monoclonal antibody or antigen-binding portion thereof comprises a variable domain of the light chain amino acid sequence of SEQ ID NO: 14.

16. A method of treating cancer in a patient, wherein said patient overexpresses IFG-I or IGF-IR, comprising:
    selecting a patient in need of treatment for cancer; and
    administering to the patient a therapeutically effective amount of a pharmaceutical composition, wherein the pharmaceutical composition comprises a monoclonal antibody or an antigen-binding portion thereof that specifically binds to human IGF-IR, wherein the antibody is antibody 4.9.2 produced by the hybridoma deposited under ATCC Accession Number PTA-2789.

17. The method of treating cancer according to claim 16, wherein the monoclonal antibody or antigen-binding portion thereof comprises a CDR1, CDR2, or CDR3 amino acid sequence within the heavy chain sequence of SEQ ID NO: 16.

18. The method of treating cancer according to claim 16, wherein the monoclonal antibody or antigen-binding portion thereof comprises a CDR1, CDR2, and CDR3 amino acid sequence within the light chain sequence of SEQ ID NO: 14.

19. The method of treating cancer according to claim 16, wherein the monoclonal antibody or antigen-binding portion thereof comprises a variable domain of the heavy chain amino acid sequence of SEQ ID NO: 16.

20. The method of treating cancer according to claim 16, wherein the monoclonal antibody or antigen-binding portion thereof comprises a variable domain of the light chain amino acid sequence of SEQ ID NO: 14.

* * * * *